US012564611B2

(12) United States Patent
Zeng et al.

(10) Patent No.: US 12,564,611 B2
(45) Date of Patent: Mar. 3, 2026

(54) PANCREATIC ENDOCRINE PROGENITOR CELLS AND USE THEREOF

(71) Applicant: CENTER FOR EXCELLENCE IN MOLECULAR CELL SCIENCE, CHINESE ACADEMY OF SCIENCES, Shanghai (CN)

(72) Inventors: Yi Zeng, Shanghai (CN); Daisong Wang, Shanghai (CN)

(73) Assignee: Center for Excellence in Molecular Cell Science, Chinese Academy of Sciences

(*) Notice: Subject to any disclaimer, the term of this patent is extended or adjusted under 35 U.S.C. 154(b) by 1007 days.

(21) Appl. No.: 17/761,445

(22) PCT Filed: Sep. 17, 2020

(86) PCT No.: PCT/CN2020/115794
§ 371 (c)(1),
(2) Date: Mar. 17, 2022

(87) PCT Pub. No.: WO2021/052401
PCT Pub. Date: Mar. 25, 2021

(65) Prior Publication Data
US 2022/0347226 A1 Nov. 3, 2022

(30) Foreign Application Priority Data
Sep. 17, 2019 (WO) ................ PCT/CN2019/106093

(51) Int. Cl.
*A61K 35/39* (2015.01)
*A61P 3/10* (2006.01)
*C12N 5/071* (2010.01)
(52) U.S. Cl.
CPC ................ *A61K 35/39* (2013.01); *A61P 3/10* (2018.01); *C12N 5/0677* (2013.01); *C12N 2500/25* (2013.01); *C12N 2501/115* (2013.01); *C12N 2501/15* (2013.01); *C12N 2501/155* (2013.01); *C12N 2513/00* (2013.01); *C12N 2533/90* (2013.01)
(58) Field of Classification Search
None
See application file for complete search history.

(56) References Cited

U.S. PATENT DOCUMENTS

| | | | |
|---|---|---|---|
| 2010/0061964 A1 | 3/2010 | Heimberg et al. | |
| 2014/0037590 A1 | 2/2014 | Weissman et al. | |
| 2014/0193373 A1 | 7/2014 | Ku | |
| 2015/0017140 A1 | 1/2015 | Bhatia et al. | |
| 2015/0265656 A1* | 9/2015 | Shamblott ........ | G01N 33/56966 435/325 |
| 2016/0175363 A1 | 6/2016 | Melton et al. | |
| 2018/0282699 A1 | 10/2018 | Jin et al. | |

FOREIGN PATENT DOCUMENTS

| | | | | |
|---|---|---|---|---|
| AU | 2005203060 | 8/2005 | | |
| CN | 102803475 | 11/2012 | | |
| CN | 104411815 | 3/2015 | | |
| CN | 106916783 | 7/2017 | | |
| CN | 107787363 | 3/2018 | | |
| JP | 2005511046 A | * 4/2005 | .............. | C12N 5/00 |
| WO | WO 2014059402 | 4/2014 | | |
| WO | WO 2017177163 | 10/2017 | | |
| WO | WO 2017201436 | 11/2017 | | |

OTHER PUBLICATIONS

Loomans, Cindy JM, et al. "Expansion of adult human pancreatic tissue yields organoids harboring progenitor cells with endocrine differentiation potential." Stem Cell Reports 10.3 (2018): 712-724. (Year: 2018).*
Seaberg, Raewyn M., et al. "Clonal identification of multipotent precursors from adult mouse pancreas that generate neural and pancreatic lineages." Nature biotechnology 22.9 (2004): 1115-1124. (Year: 2004).*
Abed et al., "Directed differentiation of progenitor cells towards an islet-cell phenotype," Am J Stem Cells, 2012, available online Nov. 30, 2012, 1(3):196-204.
Al-Hasani et al., "Adult Duct-Lining Cells Can Reprogram into b-like Cells Able to Counter Repeated Cycles of Toxin-Induced Diabetes, " Dev Cell, Jul. 2023, available online Jun. 27, 2013, 26(1):86-100.
Balazs, "Endothelial protein C receptor (CD201) explicitly identifies hematopoietic stem cells in murine bone marrow," Blood, Mar. 2006, available online Nov. 22, 2005, 107(6):2317-2321.
Baron et al., "A Single-Cell Transcriptomic Map of the Human and Mouse Pancreas Reveals Inter- and Intra-cell Population Structure," Cell Syst, Oct. 2016, available online Sep. 22, 2016, 3(4):346-360 (20 pages including the supplemental material).
Bonner-Weir et al., "In vitro cultivation of human islets from expanded ductal tissue," Proc Natl Acad Sci U S A, Jul. 2000, 97(14):7999-8004.
Broutier et al., "Culture and establishment of self-renewing human and mouse adult liver and pancreas 3D organoids and their genetic manipulation," Nature Protocols, Sep. 2016, available online Aug. 25, 2016, 11(9):1724-1743, (Author Manuscript 42 pages).
Butler et al., "Integrating single-cell transcriptomic data across different conditions, technologies, and species," Nat Biotechnol, Jun. 2018, available online Apr. 2, 2018, 36(5):411-420 (17 pages including the supplemental material).

(Continued)

*Primary Examiner* — Tracy Vivlemore
*Assistant Examiner* — Fatimah Khalaf Matalkah
(74) *Attorney, Agent, or Firm* — Fish & Richardson P.C.

(57) ABSTRACT

Provided herein are endocrine progenitor cells and organoids derived from adult islets in vitro, as well as methods for making and using the same. The compositions are useful for treating or preventing diabetes, other diseases or disorders characterized by impaired islet function, and symptoms thereof.

20 Claims, 47 Drawing Sheets
Specification includes a Sequence Listing.

(56) References Cited

OTHER PUBLICATIONS

Byrnes et al., "Lineage dynamics of murine pancreatic development at single-cell resolution," Nat Commun, Sep. 2018, 9(1), 3922, 17 pages.

Cheng et al., "Self-Renewing Endodermal Progenitor Lines Generated from Human Pluripotent Stem Cells," Cell Stem Cell, Apr. 2012, 10(4):371-384.

Criscimanna et al., "Duct Cells Contribute to Regeneration of Endocrine and Acinar Cells Following Pancreatic Damage in Adult Mice," Gastroenterology, Oct. 2011, available online Jul. 18, 2011, 141(4):1451-1462 (18 pages including the supplemental material).

Enge et al., "Single-Cell Analysis of Human Pancreas Reveals Transcriptional Signatures of Aging and Somatic Mutation Patterns," Cell, Oct. 2017, available online Sep. 28, 2017, 171(2):321-330 (25 pages including the supplemental material).

Extended European Search Report in the European Appln. No. 20866094.4, mailed on Sep. 21, 2023, 18 pages.

Fares et al., "EPCR expression marks UM171-expanded CD341 cord blood stem cells," Blood, Jun. 2017, available online Apr. 13, 2017, 129(25):3344-3351.

Furuyama et al., "Continuous cell supply from a Sox9-expressing progenitor zone in adult liver, exocrine pancreas and intestine," Nat Genet, Jan. 2011, available online Nov. 28, 2010, 43(1):34-41 (10 pages including the supplemental material).

Gao et al., "In vitro neogenesis of human islets reflects the plasticity of differentiated human pancreatic cells," Diabetologia, Nov. 2005, available online Sep. 29, 2005, 48(11):2296-2304.

Gehart et al., "Identification of Enteroendocrine Regulators by Real-Time Single-Cell Differentiation Mapping," Cell, Feb. 2019, 176(5):1158-1173 (33 pages including the supplemental material).

Gershengorn et al., "Epithelial-to-Mesenchymal Transition Generates Proliferative Human Islet Precursor Cells," Science, Dec. 2004, available online Nov. 25, 2004, 306(5705):2261-2264.

Grapin-Botton, "Three-dimensional pancreas organogenesis models," Diabetes Obes Metab, Sep. 2016, 18(Suppl 1):33-40.

Greggio et al., "Artificial three-dimensional niches deconstruct pancreas development in vitro," Development, Nov. 2013, 140(21):4452-4462 (24 pages including the supplemental material).

Grun et al., "De Novo Prediction of Stem Cell Identity using Single-Cell Transcriptome Data," Cell Stem Cell, Aug. 2016, available online Jun. 23, 2016, 19(2):266-277.

Gu et al., "Direct evidence for the pancreative lineage: NGN3+ cells are islet progenitors and are distinct from duct progenitors," Development, May 2002, 129(10):2447-2457.

Hohwieler et al., "Pancreatic Progenitors and Organoids as a Prerequisite to Model Pancreatic Diseases and Cancer," Stem Cells International, Feb. 2019, available online Feb. 25, 2019, vol. 2019, pp. 1-11.

Horton et al., "Zinc-Chelating Small Molecules Preferentially Accumulate and Function within Pancreatic ß Cells," Cell Chemical Biology, Feb. 2019, 26(2):213-222 (25 pages including the supplemental material).

Huch et al., "Unlimited in vitro expansion of adult bi-potent pancreas progenitors through the Lgr5/R-spondin axis," EMBO J, Oct. 2013, Sep. 17, 2013, 32(20):2708-2721.

Inada et al., "Carbonic anhydrase II-positive pancreatic cells are progenitors for both endocrine and exocrine pancreas after birth," Proc Natl Acad Sci U S A, Dec. 2008, 105(50):19915-19919.

International Preliminary Report on Patentability in International Appln. No. PCT/CN2019/106093, mailed on Mar. 31, 2022, 9 pages.

International Preliminary Report on Patentability in International Appln. No. PCT/CN2020/115794, mailed on Mar. 31, 2022, 7 pages.

International Search Report and Written Opinion in International Appln. No. PCT/CN2019/106093, mailed on Apr. 20, 2020, 14 pages.

International Search Report and Written Opinion in International Appln. No. PCT/CN2020/115794, mailed on Dec. 16, 2020, 11 pages.

Iwasaki et al., "Endothelial protein C receptor-expressing hematopoietic stem cells reside in the perisinusoidal niche in fetal liver," Blood, Jul. 2010, available online May 4, 2010, 116(4):544-553.

Jin et al., "Colony-forming cells in the adult mouse pancreas are expandable in Matrigel and form endocrine/acinar colonies in laminin hydrogel," Proc Natl Acad Sci U S A, Mar. 2013, available online Feb. 19, 2013, 110(10):3907-3912.

Kao et al., "Endothelial Cells Control Pancreatic Cell Fate at Defined Stages through EGFL7 Signaling," Stem Cell Reports, Feb. 2015, 4(2):181-189.

Kopp et al., "Sox9+ ductal cells are multipotent progenitors throughout development but do not produce new endocrine cells in the normal or injured adult pancreas," Development, Feb. 2011, 138(4):653-665 (14 pages including the supplemental material).

Lammert et al., "Induction of Pancreatic Differentiation by Signals from Blood Vessels," Science, Oct. 2001, avaiable online Sep. 27, 2001, 294(5542):564-567.

Lawlor et al., "Single-cell transcriptomes identify human islet cell signatures and reveal cell-type-specific expression changes in type 2 diabetes," Genome Res, Feb. 2017, available online Nov. 18, 2016, 27(2):208-222.

Loomans et al., "Expansion of Adult Human Pancreatic Tissue Yields Organoids Harboring Progenitor Cells with Endocrine Differentiation Potential," Stem Cell Reports, Mar. 2018, 10(3):712-724 (32 pages including the supplemental material).

Lysy et al., "Making ß cells from Adult Cells within the Pancreas," Curr Diab Rep, Oct. 2013, 13(5):695-703 (Author Manuscript, 14 pages).

Minami et al., "Lineage tracing and characterization of insulin-screting cells generated from adult pancreatic acinar cells," Proc Natl Acad Sci U S A, Oct. 2005, available online Oct. 6, 2005, 102(42):15116-15121.

Mohammed et al., "Microfluidic Device for Multimodal Characterization of Pancreatic Islets," Lab Chip, Jan. 2009, 9(1):97-106 (Author Manuscript, 23 pages).

Muraro et al., "A Single-Cell Transcriptome Atlas of the Human Pancreas," Cell Syst, Oct. 2016, available online Sep. 29, 2016, 3(4):385-394 (14 pages including the supplemental material).

Ouziel-Yahalom et al., "Expansion and redifferentiation of adult human pancreatic islet cells," Biochem Biophys Res Commun, Mar. 2006, available online Jan. 19, 2006, 341(2):291-298.

Pagliuca et al., "Generation of Functional Human Pancreatic ß Cells In Vitro," Cell, Oct. 2014, 159(2):428-439.

Pan et al. "Pancreas Organogenesis: From Bud to Plexus to Gland," Dev Dyn, Mar. 2011, 240(3):530-565.

Pan et al., "Spatiotemporal patterns of multipotentiality in Ptflaexpressing cells during pancreas organogenesis and injuryinduced facultative restoration," Development, Feb. 2013, available online Jan. 16, 2013, 140(4):751-764.

Pancreatic Islet Biology (Stem Cell Biology and Regenerative Medicine), 1st ed., Hardikar (ed), 2016.

Qing et al., "Research Progress in Organoid Culture," Guangdong Medical Journal, Sep. 2016, 37(18):2827-2828 (with English abstract).

Qiu et al., "Reversed graph embedding resolves complex single-cell trajectories," Nat Methods, Oct. 2017, 14(10):979-982 (Author Manuscript, 17 pages).

Ramiya et al., "Reversal of insulin-dependent diabetes using islets generated in vitro from pancreatic stem cells, " Nat Med, Mar. 2000, 6(3):278-282.

Rezania et al., "Reversal of diabetes with insulin-producing cells derived in vitro from human pluripotent stem cells," Nat Biotechnol, Nov. 2014, available online Sep. 11, 2014, 32(11):1121-1133 (14 pages including the supplemental material).

Rovira et al., "Isolation and characterization of centroacinar/terminal ductal progenitor cells in adult mouse pancreas," Proc Natl Acad Sci U S A, Jan. 2010, available online Dec. 15, 2009, 107(1):75-80.

(56) References Cited

OTHER PUBLICATIONS

Rukstalis et al., "Snail2, a mediator of epithelial-mesenchymal transitions, expressed in progenitor cells of the developing endocrine pancreas," Gene Expr Patterns, Feb. 2007, available online Nov. 11, 2006, 7(4):471-479.

Russ et al., "In Vitro Proliferation of Cells Derived From Adult Human-Cells Revealed by Cell-Lineage Tracing," Diabetes, Jun. 2008, available online Mar. 3, 2008, 57(6):1575-1583.

Scavuzzo et al., "Endocrine lineage biases arise in temporally distinct endocrine progenitors during pancreatic morphogenesis," Nat Commun, Aug. 2018, 9(1), 3356, 21 pages.

Seaberg et al., "Clonal identification of multipotent precursors from adult mouse pancreas that generate neural and pancreatic lineages, " Nat Biotechnol, Sep. 2004, available online Aug. 22, 2004, 22(9):1115-1124.

Segerstolpe et al., "Single-Cell Transcriptome Profiling of Human Pancreatic Islets in Health and Type 2 Diabetes," Cell Metab, Oct. 2016, available online Sep. 22, 2016, 24(4):593-607.

Shen et al., "Progress in the Differentiation of Stem Cells into Pancreatic ß Cells," China Biotechnology, Dec. 2011, 31(1):70-74 (with English abstract).

Smukler et al., "Supplemental Information: The Adult Mouse and Human Pancreas Contain Rare Multipotent Stem Cells that Express Insulin," Cell Stem Cell, Mar. 2011, vol. 8, 17 pages.

Smukler et al., "The Adult Mouse and Human Pancreas Contain Rare Multipotent Stem Cells that Express Insulin," Cell Stem Cell, Mar. 2011, 8(3):281-293.

Sneddon et al., "Self-renewal of embryonic-stem-cell-derived progenitors by organ-matched mesenchyme," Nature, Nov. 2012, avaialble online Oct. 7, 2012, 491(7426):765-768 (6 pages including the supplemental material).

Sugiyama et al., "Reconstituting pancreas development from purified progenitor cells reveals genes essential for islet differentiation," Proc Natl Acad Sci U S A, Jul. 2013, available online Jul. 12, 2013, 110(31):12691-12696.

Van de Casteele et al., "Neurogenin 3+ cells contribute to b-cell neogenesis and proliferation in injured adult mouse pancreas," Cell Death Dis, Mar. 2013, 4(3), e523, 11 pages.

Wang et al., "Identification of multipotent mammary stem cells by protein C receptor expression," Nature, Jan. 2015, available online Oct. 19, 2014, 517(7532):81-84 (16 pages including the supplemental material).

Wang et al., "Isolation of mouse pancreatic islet Procr+ progenitors and long-term expansion of islet organoids in vitro," Nature Protocols, May 2022, available online Apr. 8, 2022, 17(5):1359-1384.

Wang et al., "Long-term Expansion of Pancreatic Islet Organoids from Resident Procr+ Progenitors," and Supplemental Information, Cell, Mar. 2020, 180(6):1198-1211 (36 pages including the supplemental material).

Wedeken et al., "Adult Murine Pancreatic Progenitors Require Epidermal Growth Factor and Nicotinamide for Self-Renewal and Differentiation in a Serum- and Conditioned Medium-Free Culture," Stem Cells and Development, Apr. 2017, 26(8):599-607.

Wedeken et al., "Adult Murine Pancreatic Progenitors Require Epidermal Growth Factor and Nicotinamide for Self-Renewal and Differentiation in a Serum- and Conditioned Medium-Free Culture—Supplementary Data," Stem Cells and Development, Apr. 2017, 7 pages.

Wells, "Genes expressed in the developing endocrine pancreas and their importance for stem cell and diabetes research," Diabetes/Metabolism Research and Reviews, May 2003, 19(3):191-201.

Xu et al., "β Cells Can Be Generated from Endogenous Progenitors in Injured Adult Mouse Pancreas," Cell, Jan. 2008, 132(2):197-207.

Yatoh et al., "Differentiation of Affinity-Purified Human Pancreatic Duct Cells to β-Cells," Diabetes, Jul. 2007, available online May 1, 2007, 56(7):1802-1809.

Yu et al., "Identification of blood vascular endothelial stem cells by the expression of protein C receptor," Cell Res, Oct. 2016, available online Jul. 1, 2016, 26(10):1079-1098.

Zhou et al., "Tracing haematopoietic stem cell formation at single-cell resolution," Nature, May 2016, available online May 18, 2016, 533(7604):487-492 (17 pages including the supplemental material).

* cited by examiner

GO analysis of the new population
(1536 signature genes)

*Procr* mGFP-2A-LacZ
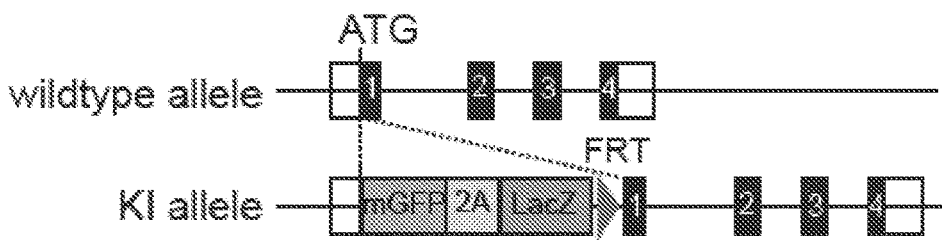
FIG. 3F
*Procr* mGFP-2A-LacZ
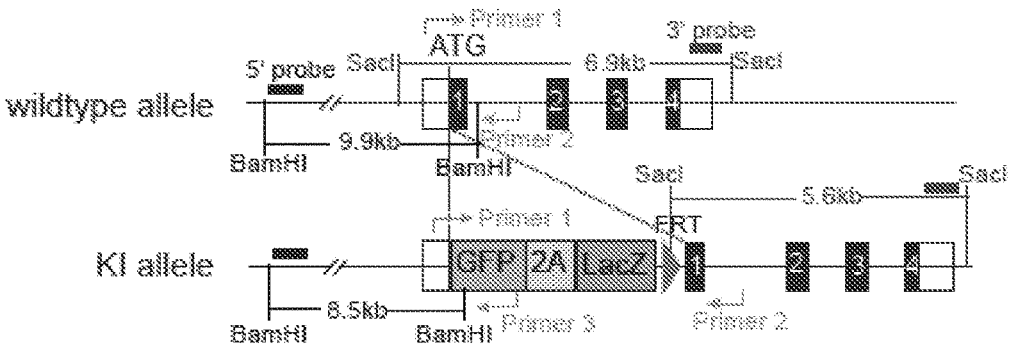
FIG. 3G
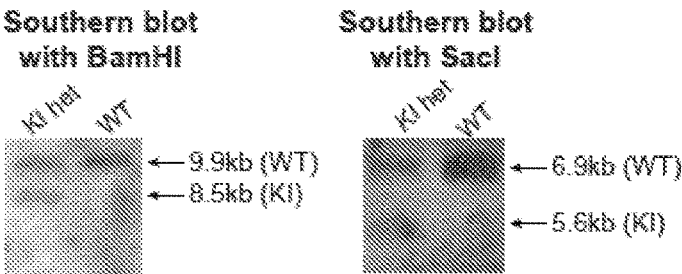
FIG. 3H
Genotyping PCR with primers 1, 2 & 3
FIG. 3I

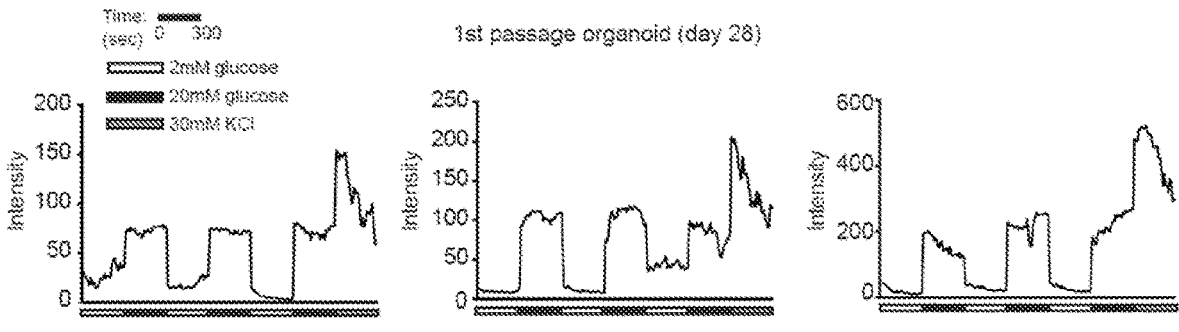
FIG. 5G
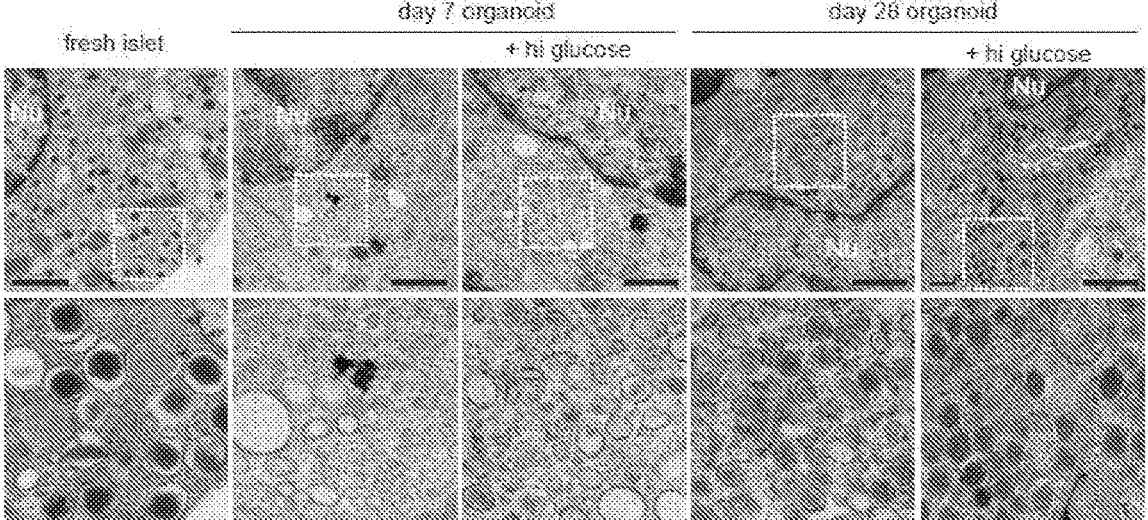
FIG. 5H
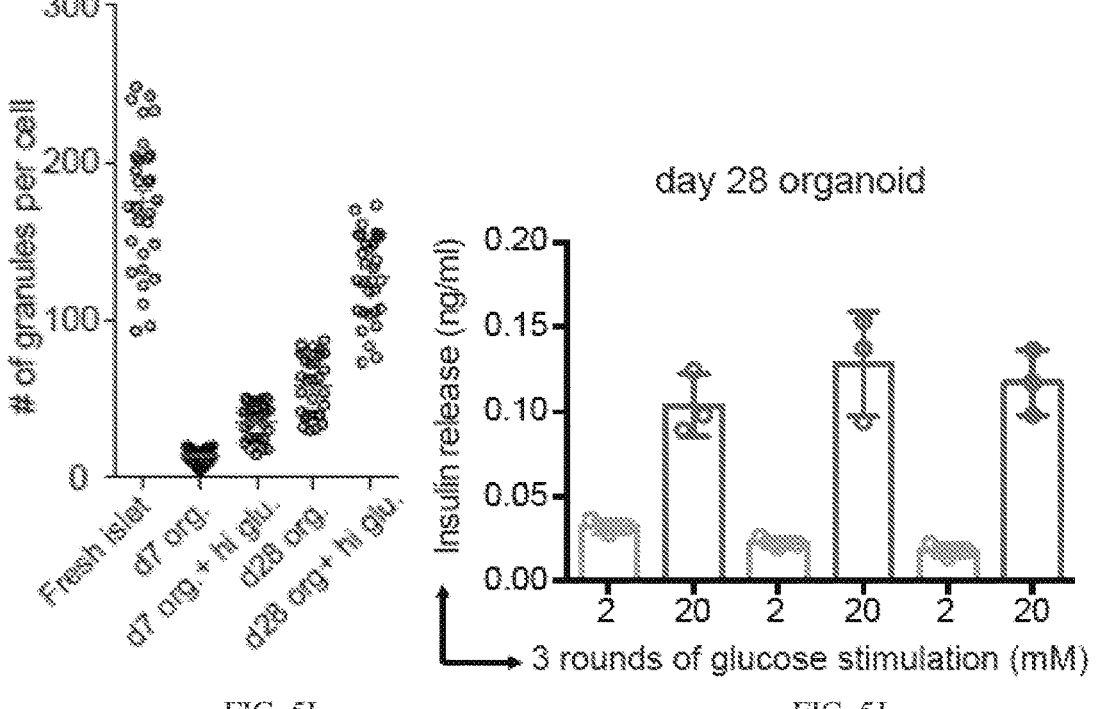
FIG. 5I
FIG. 5J fresh islet

Gcg DAPI    Sst DAPI    Ppy DAPI fresh islet day 28 organoid

Gcg DAPI    Sst DAPI    Ppy DAPI day 28 organoid

1st passage    3rd passage    9th passage    16th passage (day 7)

7th organoid (day 30 +hi glucose)

15th passage (day 30+hi glucose)

7th organoid (day 30 +hi glucose)

7th organoid (day 30)
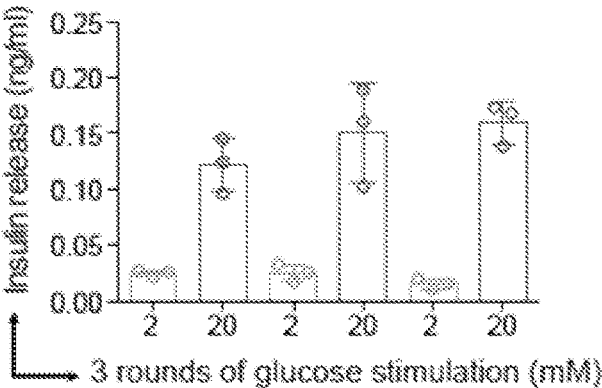
FIG. 6M
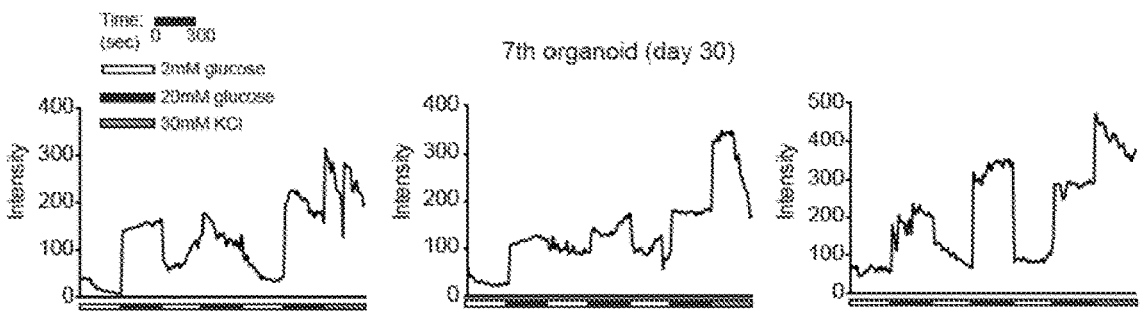
FIG. 6N
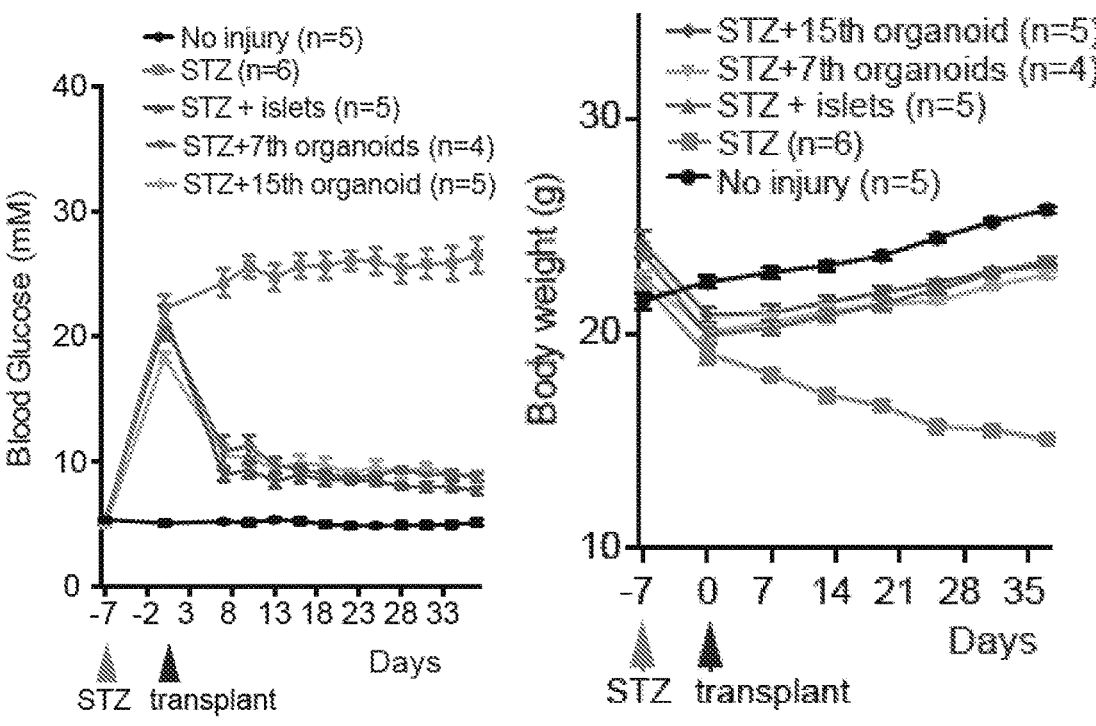
FIG. 7A                                    FIG. 7B

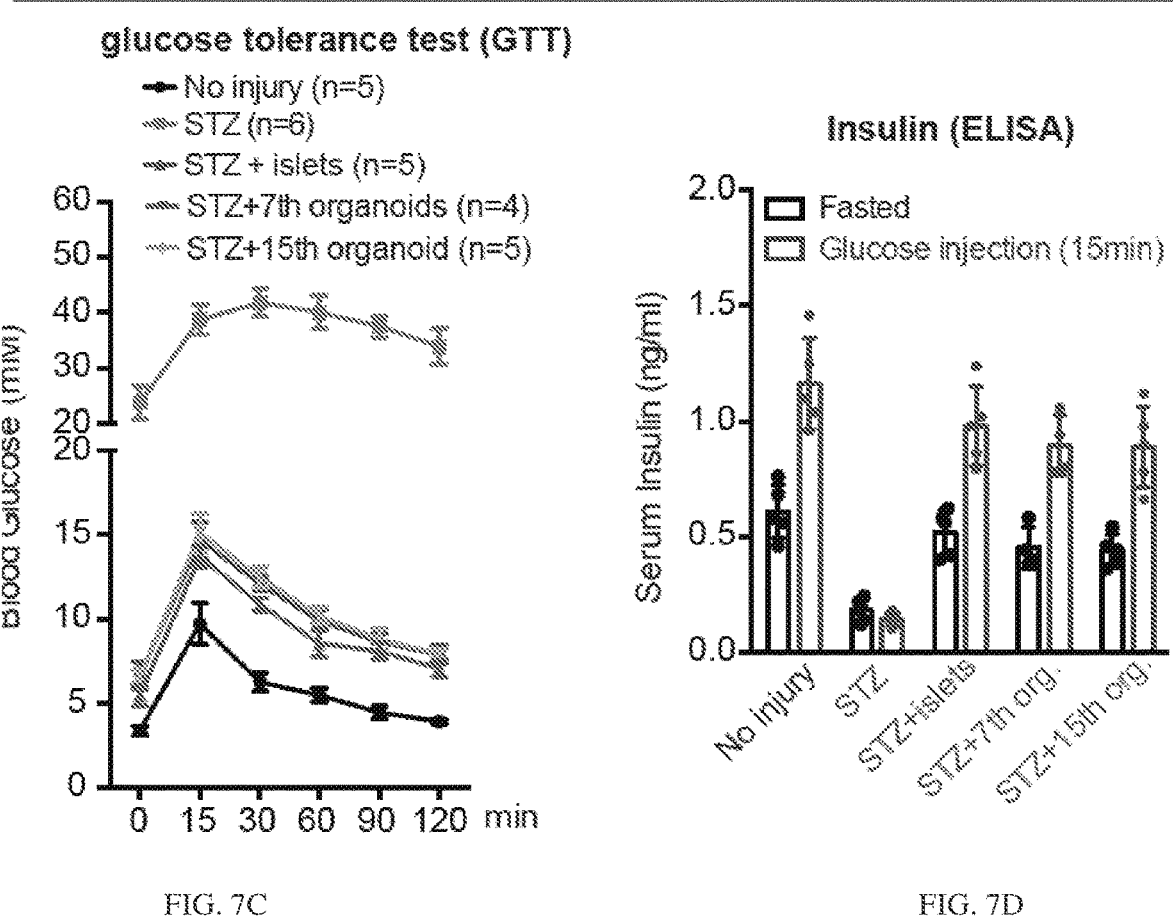
FIG. 7C                                                    FIG. 7D 1 month after transplantation 1 month after organoid transplantaiton

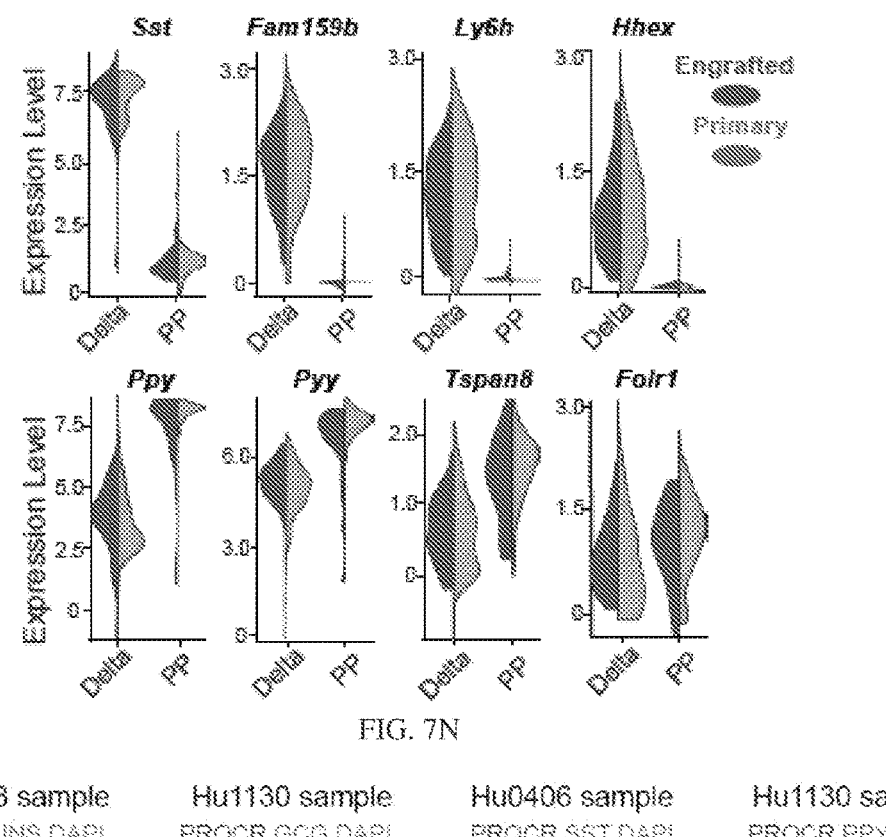
FIG. 7N
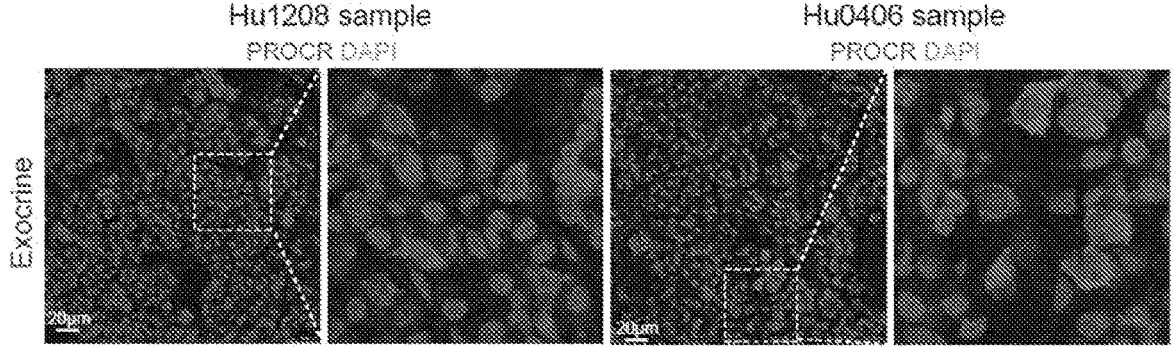
FIG. 8A
FIG. 8B

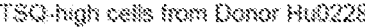
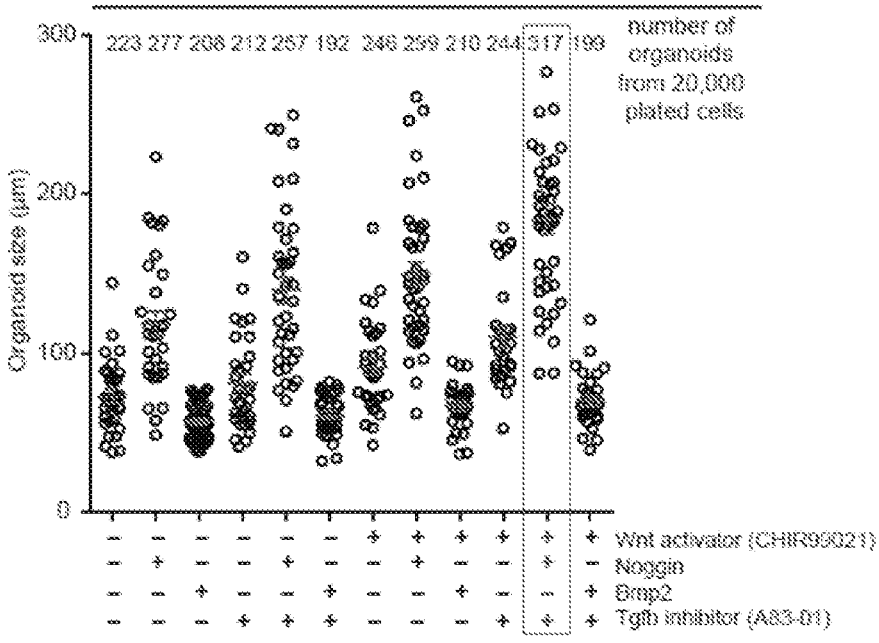
FIG. 10C
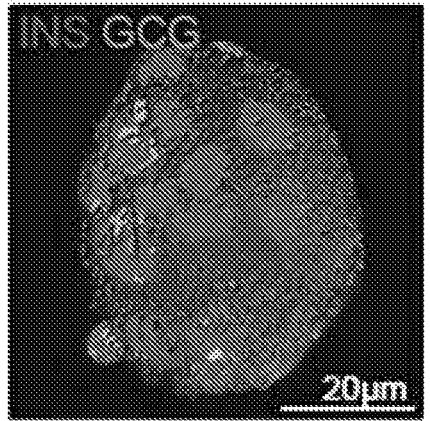
Organoid
from Donor Hu1130
FIG. 10D

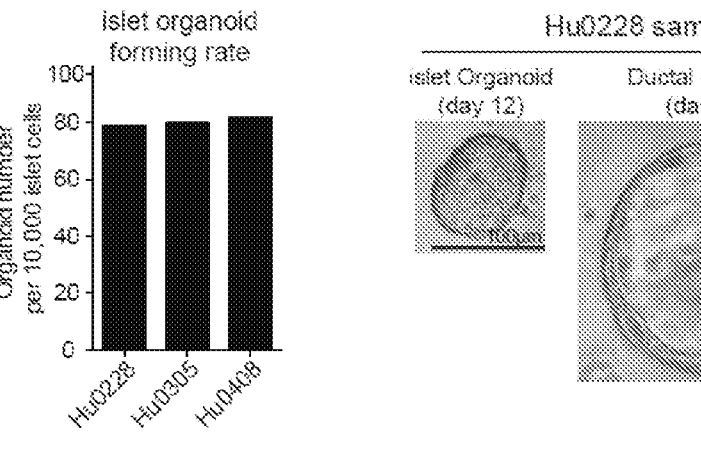
FIG. 11A                              FIG. 11B
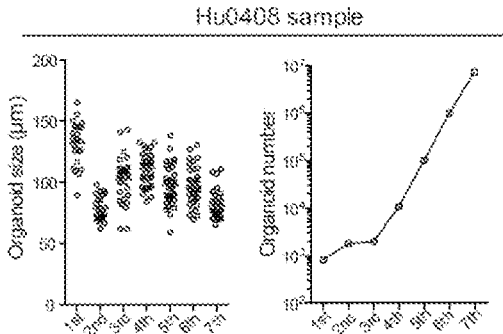
FIG. 11C
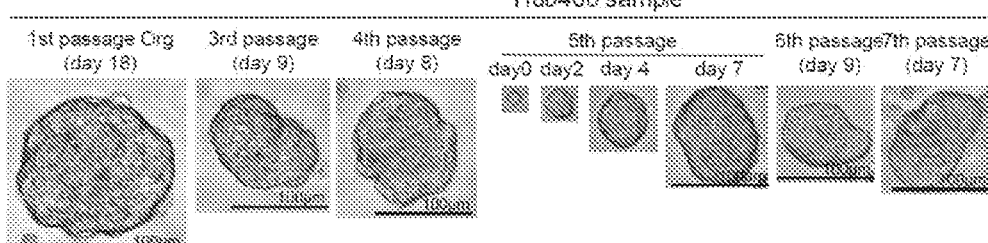
FIG. 11D 1st passage Org (day 12) Hu0228
FIG. 12A
1st passage Org (day 12) Hu0408
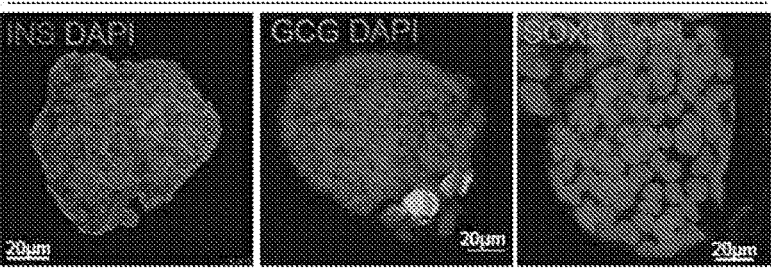
FIG. 12B
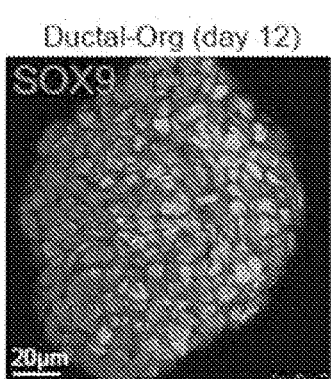
FIG. 12C
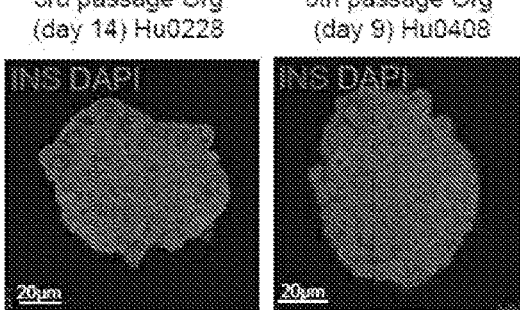
FIG. 12D
FIG. 12E

C

D

D

E

F

A
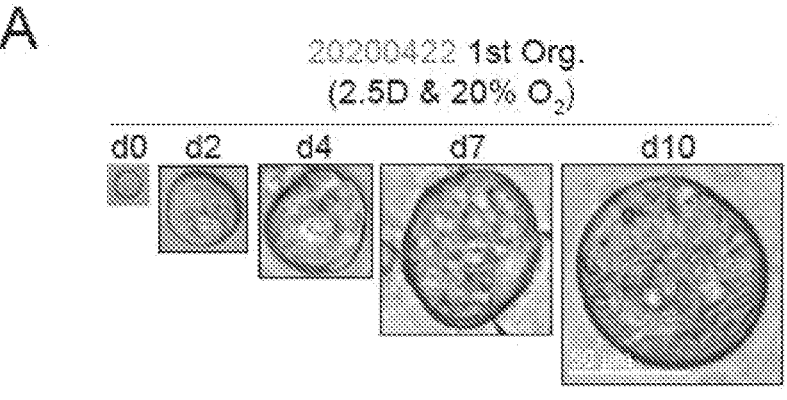
FIG. 16A
B
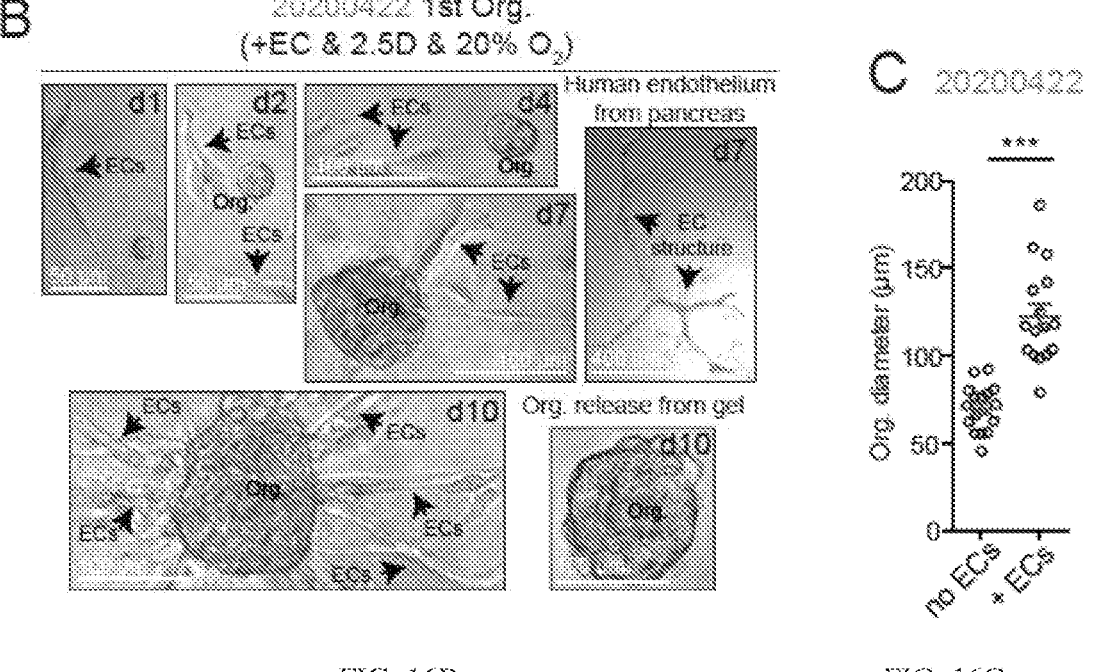
FIG. 16B
FIG. 16C

PANCREATIC ENDOCRINE PROGENITOR CELLS AND USE THEREOF

CROSS-REFERENCE TO RELATED APPLICATIONS

This application is a 371 U.S. National Phase Application of International Patent Application No. PCT/CN2020/115794, filed Sep. 17, 2020, which claims priority to and the benefit of International Patent Application No. PCT/CN2019/106093 filed Sep. 17, 2019, the entire disclosures of which are incorporated hereby by reference.

BACKGROUND

The pancreas consists of three main cellular components: endocrine islets, exocrine acini, and ducts. Pancreatic β-cells of the islets of Langerhans are the only cells that produce insulin in humans as well as in almost all other vertebrates. In the mouse, the islet is organized into spherical structures in which β-cells form a core surrounded by a mantle of α-, δ- and pancreatic polypeptide (PP)-cells. These cells produce insulin, glucagon, somatostatin and pancreatic polypeptide (PP; Ppy) respectively (Pan and Wright, 2011). β-cells have a limited capacity for regeneration, a predisposing factor for the development of diabetes (Hardikar, 2016).

Cell therapy is considered as a potential therapeutic alternative to traditional treatments of diabetes. Islet- and whole pancreas transplantations can restore glucose homeostasis by replenishing β cells (Lysy et al., 2013). Limitations in availability of donors have led to a search for strategies for generating β-cells in vitro. Besides the use of embryonic stem cell (ES)/induced pluripotent stem cell (iPSCs)-based technologies for the generation of transplantable (3-cells (Cheng et al., 2012; Pagliuca et al., 2014; Rezania et al., 2014; Sneddon et al., 2012), organoids directly derived from the tissue of interest have been investigated. However, it has so far proven difficult to produce new β-cells in culture from embryonic or adult pancreas, while the closely related enteroendocrine cells of the gut are readily generated in such organoids (Gehart et al., 2019).

Mouse embryonic pancreas progenitors, cultured in three-dimensional (3D), reflect exocrine and endocrine cell differentiation in vitro, yet does not support long-term expansion of pancreas cells (Greggio et al., 2013; Sugiyama et al., 2013). Tissue culture strategies using adult duct (Bonner-Weir et al., 2000; Gao et al., 2005; Huch et al., 2013; Jin et al., 2013; Ramiya et al., 2000; Rovira et al., 2010; Yatoh et al., 2007), acinar (Minami et al., 2005), and insuin$^{low}$ (Seaberg et al., 2004; Smukler et al., 2011) cells have only been marginally effective for expanding and differentiating putative progenitor cells into β-like cells.

Thus, a need exists for methods and compositions for in vitro production and long-term expansion of β-cells.

SUMMARY

In one aspect, provided herein is a method of producing a pancreatic organoid in vitro, comprising: providing an endocrine progenitor cell; and 3D culturing in vitro the endocrine progenitor cell in an organoid medium under conditions suitable to produce a pancreatic organoid comprising functional f3-cells and/or f3-like cells, wherein preferably the organoid medium further comprises a three-dimensional matrix such as basement membrane matrix MATRIGEL™ and hydrogel.

In some embodiments, the endocrine progenitor cell can be isolated from adult islet cells. In some embodiments, the endocrine progenitor cell is provided within a population of adult islet cells (e.g., without isolation). In some embodiments, a population of endocrine progenitor cells can be provided, in substantially pure and isolated form, or in enriched form along with other adult islet cells, or in naturally-existing form within adult islet cells as obtained from a subject.

In some embodiments, the adult islet cells can be from human and the endocrine progenitor cell can be MSLN+. The endocrine progenitor cell can further express one or more of UPK1B, S100A6, LGALS4, SDCBP2, SDC1, IGFBP3, HMGA1, ITGB4, ITGB6, HN1, GPRC5A, SLPI, LAMC2, FERMT1, MGLL, SEMA3B, TST, SFN, CDH3 and PROCR. In some embodiments, the method can further include contacting, in vitro, dissociated adult human islet cells with an anti-MSLN antibody or antigen-binding fragment thereof, followed by fluorescence assisted cell sorting (FACS), to isolate the endocrine progenitor cell. In certain embodiments, the organoid medium for culturing human cells can include a basal medium such as DMEM/F12 supplemented with one or more of: 10-200 (e.g., 50) ng ml$^{-1}$ EGF, 1-50 (e.g., 10) ng ml$^{-1}$ FGF2, 1-10 (e.g., 3) μM Wnt agonist such as CHIR99021 or 1-100 (e.g., 30) ng/ml Wnt surrogate such as NGS (next generation surrogate), 0.1-5 (e.g., 0.5) μM TGF-beta pathway inhibitors such as SB431542 or A83-01, 10-500 (e.g., 100) ng ml$^{-1}$ Bmp inhibitor such as Noggin, 1-10 (e.g., 2.5) μM Rock inhibitor such as Y27632, and 1-10 (e.g., 0.5) μM of p38 inhibitor SB202190; wherein optionally the basal medium is further supplemented with one or more of 1-5% (e.g., 2%) B27, 0.1-5% (e.g., 1%) ITS, 0.1-5 (e.g., 2) μg ml$^{-1}$ heparin, and 1-100 (e.g., 50) ng ml$^{-1}$ VEGFa.

In some embodiments, the adult islet cells can be from mouse and the endocrine progenitor cell can be Procr+. In some embodiments, the endocrine progenitor cell further expresses one or more of Rspo1, Fgf1, Upk3B, Hoxa5 and Msln. In some embodiments, the 3D culturing step can include co-culturing with a plurality of endothelial cells. In some embodiments, the method can further include contacting, in vitro, dissociated adult mouse islet cells with an anti-Procr antibody or antigen-binding fragment thereof, followed by fluorescence assisted cell sorting (FACS), to isolate the endocrine progenitor cell. In some embodiments, the culture medium for mouse cells can include a basal medium such as DMEM/F12 supplemented with one or more of: 10-200 (e.g., 50) ng ml$^{-1}$ EGF, 1-50 (e.g., 10) ng ml$^{-1}$ FGF2, and 1-20 (e.g., 5) ng ml$^{-1}$ VEGFa; wherein optionally the basal medium is further supplemented with one or more of 1-5% (e.g., 2%) B27, 0.1-5% (e.g., 1%) ITS, and 0.1-5 (e.g., 2) μg ml$^{-1}$ heparin.

In some embodiments, the 3D culturing and/or co-culturing step can include culturing until the endocrine progenitor cell forms a colony of about 100-300 μm in diameter, and continuously culturing the colony to form a pancreatic organoid of about 150-500 μm in diameter.

Another aspect relates to a method of obtaining pancreatic organoids in vitro, comprising: (a) enriching endocrine cells from adult pancreas, preferably by one or more of the following methods: (1) staining dissociated adult pancreas cells with TSQ (6-methoxy-8-p-toluenesulfonamido-quilone), followed by FACS; (2) density gradient centrifugation of dissociated adult pancreas cells; and (3) hand-picking and dissociating islets from adult pancreas; and (b) 3D culturing the enriched endocrine cells in an organoid medium under conditions suitable to produce a pancreatic organoid comprising functional β-cells and/or β-like cells, wherein preferably the organoid medium further comprises a three-dimensional matrix.

In some embodiments, the organoid medium can include basement membrane matrix MATRIGEL™ or hydrogel and a 20 basal medium such as DMEM/F12 supplemented with one or more of: 10-200 (e.g., 50) ng mr1 EGF, 1-50 (e.g., 10) ng mr1 FGF2, 1-10 (e.g., 3) μM Wnt agonist such as CHIR99021 or 1-100 (e.g., 30) ng/ml Wnt surrogate such as NGS (next generation surrogate), 0.1-5 (e.g., 0.5) μM TGF-beta pathway inhibitors such as SB431542 or A83-0l, 10-500 (e.g., 100) ng mr1 Bmp inhibitor such as Noggin, 1-10 (e.g., 2.5) μM Rock inhibitor such as Y27632, and 1-10 (e.g., 0.5) 25 μM of p38 inhibitor SB202190. In some embodiments, the basal medium can be further supplemented with one or more of 1-5% (e.g., 2%) B27, 0.1-5% (e.g., 1%) ITS, 0.1-5 (e.g., 2) μg mr1 heparin, and 1-100 (e.g., 50) ng mr1 VEGFa. In some embodiments, the pancreatic organoid is about 50-500 or about 100-300 μm in diameter.

In various embodiments, any one of the methods disclosed herein can further include a step of expanding the pancreatic organoid through passaging for at least 10 times, at least 20 times, or at least 30 times. The methods can additionally include culturing the expanded pancreatic organoids for about 1-12 or 1-4 or 2-12 weeks (e.g., about 1, 2, 3, 4, 5, 6, 7, 8, 9, 10, 11, 12 weeks or more, or about 7-100 days) to generate mature organoids. The mature organoid can, in some embodiments, sense glucose and produce and secrete insulin in response to glucose.

Also provided herein is a method of obtaining endocrine progenitor cells, comprising: contacting, in vitro, adult islet cells with an anti-MSLN antibody or antigen-binding fragment thereof; and isolating a MSLN$^+$ endocrine progenitor cell that binds to the anti-MSLN antibody or fragment thereof, preferably using fluorescence assisted cell sorting (FACS).

Another method of obtaining endocrine progenitor cells includes: contacting, in vitro, adult islet cells with an anti-Procr antibody or antigen-binding fragment thereof; and isolating a Procr$^+$ endocrine progenitor cell that binds to the anti-Procr antibody or fragment thereof, preferably using fluorescence assisted cell sorting (FACS).

A further aspect relates to a composition comprising a plurality of endocrine progenitor cells isolated from adult islet cells, a culture medium and optionally a plurality of endothelial cells. In some embodiments, the endocrine progenitor cells express Procr. In some embodiments, the culture medium further comprises a three-dimensional matrix, preferably basement membrane matrix MATRIGEL™ or hydrogel.

In some embodiments, the adult islet cells are from human, and the endocrine progenitor cells express MSLN and optionally one or more of UPK1B, S100A6, LGALS4, SDCBP2, SDC1, IGFBP3, HMGA1, ITGB4, ITGB6, HN1, GPRC5A, SLPI, LAMC2, FERMT1, MGLL, SEMA3B, TST, SFN, CDH3 and PROCR. In some embodiments, the culture medium for human cells comprises a basal medium such as DMEM/F12 supplemented with one or more of: 10-200 (e.g., 50) ng ml$^{-1}$ EGF, 1-50 (e.g., 10) ng ml$^{-1}$ FGF2, 1-10 (e.g., 3) μM Wnt agonist such as CHIR99021 or 1-100 (e.g., 30) ng/ml Wnt surrogate such as NGS (next generation surrogate), 0.1-5 (e.g., 0.5) μM TGF-beta pathway inhibitors such as SB431542 or A83-01, 10-500 (e.g., 100) ng ml$^{-1}$ Bmp inhibitor such as Noggin, 1-10 (e.g., 2.5) μM Rock inhibitor such as Y27632, and 1-10 (e.g., 0.5) μM of p38 inhibitor SB202190; wherein optionally the basal medium is further supplemented with one or more of 1-5% (e.g., 2%) B27, 0.1-5% (e.g., 1%) ITS, 0.1-5 (e.g., 2) μg ml$^{-1}$ heparin, and 1-100 (e.g., 50) ng ml$^{-1}$ VEGFa.

In some embodiments, the adult islet cells are derived from mouse, and the endocrine progenitor cells express Procr and optionally one or more of Rspo1, Fgf1, Upk3B, Hoxa5 and Msln. In some embodiments, the culture medium for mouse cells comprises a basal medium such as DMEM/F12 supplemented with one or more of: 10-200 (e.g., 50) ng ml$^{-1}$ EGF, 1-50 (e.g., 10) ng ml$^{-1}$ FGF2, and 1-20 (e.g., 5) ng ml$^{-1}$ VEGFa; wherein optionally the basal medium is further supplemented with one or more of 1-5% (e.g., 2%) B27, 0.1-5% (e.g., 1%) ITS, and 0.1-5 (e.g., 2) μg ml$^{-1}$ heparin.

Another aspect relates to a pancreatic organoid comprising functional β-cells and/or β-like cells differentiated in vitro from endocrine progenitor cells, wherein the endocrine progenitor cells are isolated from adult islet cells. In some embodiments, the pancreatic organoid senses glucose and produces and secretes insulin in response to glucose. In some embodiments, the pancreatic organoid is about 50-500 or about 100-300 μm in diameter.

A further aspect relates to the culture media disclosed herein, for in vitro expansion and/or differentiation of endocrine progenitor cells and pancreatic organoids.

Use of the organoid disclosed herein is also provided, for treating or preventing diabetes, or for screening in vitro an agent for treating or preventing diabetes.

BRIEF DESCRIPTION OF THE DRAWINGS

FIG. 1A includes graphs depicting distributions of the number of unique molecular identifiers (UMIs) per cell (left) and the number of genes detected per cell (right) are shown for pancreatic single cell (sc) RNAseq data. FIG. 1B includes dot-plots illustrating the reproducibility between three biological replicates. Average gene expression values (Log 2(TPM+1)) across all cells of three sc RNAseq experiments are used for the calculation (r=Pearson correlation coefficient). FIG. 1C includes t-SNE plots of three independent sc RNAseq experiments. Cell counts of each experiment and indicated cell type are labeled in brackets. Throughout the figures, unless indicated otherwise, "Mesen" denotes mesenchymal; "Endo." denotes endothelial. "New pop" denotes new population. FIG. 1D is a series of t-SNE plots of marker genes expression for endocrine or exocrine cells. For FIGS. 1D, 1E, and 1I, post hoc cluster interpretation was based on the expression of known cell type markers; and the different clusters represent the same cell types as shown in FIG. 1C. FIG. 1E is a series of t-SNE plots of marker genes expression for cell lineages other than endocrine and exocrine. FIG. 1F is a t-SNE plot of 7,160 pancreatic single cell (sc) RNAseq profiles (points) and annotated post hoc. The new population (new pop.) is. Cell counts of indicated cell types are in parentheses. Cells are pooled together from three biological replicates. FIG. 1G is a series of tSNE plots and accompanying Vlin plots illustrating gene expression for different pancreatic cell types. The different clusters represent the same cell types as shown in FIG. 1F. FIG. 1H is a series of tSNE plots and accompanying Vlin plots illustrating gene expression for different pancreatic cell types. The different clusters represent the same cell types as shown in FIG. 1F. FIG. 1I includes t-SNE plots of marker genes expression for the new population of cells. FIG. 1J is a heat map of cell type-enriched genes. Each column represents a single cell and each row represents one signature gene. The shading ranging from dark shading to brighter shading, which indicate low to high relative gene expression levels, respectively. FIG. 1K is a dot plot for signature genes of each cluster. The shadings denote average expression levels and the sizes of dots denote fractional expression. FIG. 1L is graph of selected gene ontology (GO) terms of upregulated genes (1536 genes are selected with p value $<5\times10^{-3}$) in the new population. FIG. 1M includes tSNE plots and Vlin plots illustrating expression levels of epithelial and mesenchymal markers are projected onto t-SNE plots. The Vlin plot under the t-SNE plot shows the expression level (Log 2(TPM+1)) of the indicated gene in each cell type. The new population (circled) express both epithelial and mesenchymal markers, indicating the EMT properties.

FIGS. 2A-2I illustrate that the new population in adult islets aligns with a subpopulation of embryonic endocrine cells. FIG. 2A is a tSNE plot showing two different single cell RNAseq datasets containing E14.5 Ngn3-expressing endocrine precursors integrated with the presently disclosed adult single cell RNAseq dataset and annotated post hoc. Both the aligned (left) and split (right) view are shown. Cell counts of each dataset and the new population (new pop.) are in parentheses. FIG. 2B includes tSNE plots that show expression levels of pancreatic endocrine and exocrine marker genes for each indicated cell type. The color bar and Log 2(TPM+1) value for each indicated gene are shown. FIG. 2C includes t-SNE plots of expression levels of epithelial and mesenchymal markers for E14.5 Ngn3-expressing endocrine precursors. The color bar and Log 2(TPM+1) value for each indicated gene are shown. Similar to the adult new population, the new sub-cluster (circled) of E14.5 Ngn3-expressing endocrine precursors express both epithelial and mesenchymal markers, indicating the EMT properties. FIG. 2D includes t-SNE plots showing expression levels of Ngn3. FIG. 2E includes t-SNE plots showing Rspo1 and Procr expression in the new population. The color bar and Log 2(TPM+1) value for each indicated gene are shown. E14.5 Ngn3$^+$ new pop. cells (circled) express Rspo1 and Procr at the similar levels as adult new pop. cells, while adult new pop. cells lose their Ngn3 expression. FIG. 2F is a dot plot showing the expression signatures of the new population across three datasets. FIG. 2G includes t-SNE plots that show expression levels of marker genes in the new population. Three datasets are shown separately for comparison. The color bar and Log 2(TPM+1) value for each indicated gene are shown. Within each dataset, cells are separated as new pop and others. The shadings denote average expression levels and the sizes of dots denote fractional expression. FIG. 2H includes graphs showing the developmental trajectory of the adult new population of cells and alpha, beta, delta, and PP cells (4,986 cells used) produced by Monocle2. The colors in left panel denote cell types. The cell counts for the indicated cell types are labeled in brackets. Pseudotime (arbitrary units) is depicted from dark to light blue (right panel). FIG. 2I is a gene branched Heat map depicting the expression of genes along each branch in pseudotime. An independent expression pattern is calculated across the entire pseudotime trajectory for each branch. Therefore, the portion of the trajectory before the branch point is displayed for each branch separately. Genes are clustered based on expression pattern across pseudotime, selected genes with differential expression along the branches are labeled on the right.

FIGS. 3A-3L characterize the isolated new islet population using the Procr surface marker. FIG. 3A includes graphs depicting the FACS analysis gating strategy for unstained control islet Procr-expressing cells. Doublets were excluded based on forward scatter and trigger pulse width. Lin$^+$ cells are excluded by CD31, CD45, and Ter119 antibodies staining. Procr$^+$ cells are analyzed in the EpCAM$^+$ islet epithelial cells. FIG. 3B includes graphs depicting the FACS analysis gating strategy for antibody stained samples of islet Procr-expressing cells. Doublets were excluded based on forward scatter and trigger pulse width. Lin$^+$ cells are excluded by CD31, CD45, and Ter119 antibodies staining. Procr$^+$ cells are analyzed in the EpCAM$^+$ islet epithelial cells. For FIGS. 3A and 3B, one of three similar biological replicates is shown. FIG. 3C include graphs summarizing the FACS analysis of Procr-expressing cells in hand-picked mouse islets. The Lin$^+$ and non-epithelial cells are gated out based on Lin (including CD31, CD45, and Ter119) and EpCAM antibodies staining. Within the Lin$^-$, EpCAM$^+$ islet epithelial compartment $1.02\pm0.14\%$ cells are Procr$^+$. Data are pooled from five biological replicates and presented as mean±s.e.m. FIG. 3D includes graphs that show the expression levels of new population signature genes in each isolated cell populations (i.e., the FACS-sorted islet or non-islet Procr$^+$ and Procr$^-$ pancreatic cells) as measured by qPCR. Islet Procr+ cells are the enriched new population with high levels of the new population markers expression. n=3 biological replicates. For each replicate, cells were isolated from four mice. Data are presented as mean±s.e.m. FIG. 3E includes graphs of the FACS analysis of Procr$^+$ cells in Ngn3-Cre; Rosa26-tdTomato pancreatic islets. Islet epithelial cells are marked by Lin$^-$, EpCAM$^+$. The majority of Procr$^+$ cells are tdTomato$^+$ (tdTom$^+$). One of three similar biological replicates is shown. FIG. 3F is a diagram of a double-reporter allele of Procr with a membrane GFP (mGFP)-2A-LacZ cassette inserted after the ATG start codon of Procr. FIG. 3G is a diagram illustrating a targeting strategy to generate the ProcrmGFP-2A-LacZ knock-in double reporter mouse. Designs of southern blot probe and genotyping primers are as indicated. FIG. 3H includes images of Southern blot analysis with a 5' external probe of BamHI-digested DNA from mouse embryonic stem cells that show an 8.5 kb band in addition to the 9.9 kb WT band (left) and an image of a Southern blot analysis with a 3' external probe of SacI-digested DNA from mouse embryonic stem cells that shows a 5.6 kb band in addition to the 6.9 kb WT band (right) in clones that have undergone homologous recombination at the Procr locus. FIG. 3I is a gel image of genotyping PCR reaction products, which indicate that pups #2, 3, 5, 7 were heterozygotes. One of three similar experiments are shown. FIG. 3J includes images of whole-mount X-gal staining that shows individual LacZ-expressing (Procr$^+$) cells within ProcrmGFP-2A-LacZ islets. The wildtype negative control is shown on the right. Scale bar denotes 20 μm. A similar distribution pattern was observed using in three mice. FIG. 3K includes a graph of a FACS analysis of Procr$^+$ and Procr$^-$ cells (image) and a graph illustrating the overlap of Procr$^+$ cells and mGFP$^+$ cells, which validates the ProcrmGFP-2A-LacZ knock-in report mouse. The islet Procr$^+$ or Procr$^-$ cells were FACS sorted and validated by mGFP immunostaining. The overlapping of sorted Procr$^+$ and mGFP$^+$ cells are quantified. The ProcrmGFP-2A-LacZ knock-in mice recapitulate the Procr expression in islets. n=3 biological replicates. Data are presented as mean±s.e.m. Scale bar denotes 20 FIG. 3L includes representative confocal images of ProcrmGFP-2A-LacZ islets whole mount immunostaining, which indicate that mGFP+ cells (Procr+ cells, allow) do not overlap with the mature β-cells (Ins$^+$), α-cells (Gcg$^+$), δ-cells (Sst$^+$) or PP-cells (Ppy$^+$). Scale bar denotes 20 Similar results are confirmed by n=3 mice.

FIG. 4A includes bright field images of freshly isolated primary islet cells cultured after 7 days. Procr$^+$ or Procr$^-$ islet cells are FACS sorted from ICR mice and cultured respectively. Only Procr$^+$ cells form colonies. Experiments were performed for n=3 biological replicates. For each replicate, cells are sorted from at least 5 mice. Scale bar denotes 50 FIG. 4B is a scatterplot showing the size per islet organoid cultured for 7 or 28 days, with or without endothelial cells. Experiments were performed for 3 biological replicates. One of three similar results are shown. The average sizes are shown as mean±s.e.m.

FIG. 5A illustrates the FACS analysis of Procr$^+$ and Procr$^-$ cells sorted (from ICR or FVB mice) and co-cultured with CD31$^+$ endothelial cells (from Actin-DsRed), respectively. FACS analysis of Procr). Bright field/fluorescence representative images are presented of freshly isolated primary islet cells cultured after 5 or 8 days. The red fluorescence indicating where CD31$^+$ endothelial cells are. Only Procr$^+$ cells form islet organoids under this culture condition. n=5 biological replicates. For each replicate, cells are sorted from at least 5 mice. Scale bar denotes 50 FIG. 5B includes bright field (left) and whole mount immunofluorescence images (right) of Procr$^+$ cell-derived islet organoids cultured for 28 days. Both Procr$^+$ cells and CD31$^+$ endothelial cells are sorted from ICR mice. The endothelial cells are labeled by CD31 antibody staining in red color. n=3 biological replicates. For each replicate, cells are sorted from at least 5 mice. "Org." denotes organoid. Scale bar denotes 50 μm. FIG. 5N is a graph quantifying the results observed in FIG. 5M. For FIGS. 5K-5N, the existence of different types of hormone-expressing cells within organoids is validated based on n=3 biological replicates. One of three similar quantification results is shown. n=3 mice are used for the quantification of fresh islets. Scale bar denotes 20 μm. Data are presented as mean±s.e.m FIGS. 6A-6N illustrate that Procr$^+$ cells-derived organoids can be expanded in vitro. FIG. 6A includes representative images of cultured organoids from different passages. All passage experiments were performed for n=3 biological replicates. Scale bar denotes 50 μm. FIG. 6B is a graph showing the sizes of the cultured organoids from FIG. 6A. One of three similar quantification results are shown. Average sizes of organoids are shown as mean±s.e.m. FIG. 6M is a graph depicting ELISA measurements of secreted insulin from 7th passaged day 30 islet organoids challenged sequentially with 2, 20, 2, 20, 2, and 20 mM glucose, with a 30-minute incubation for each condition. n=3 biological replicates. Data are presented as mean±s.e.m. FIG. 6N includes graphs depicting representative population measurements of dynamic normalized Fluo-4 fluorescence intensity for 7th passaged day 30 islet organoids challenged sequentially with 2, 20, 2, 20, 2, and 20 mM glucose and 30 mM KCl. The x axis represents time. n=3 biological replicates are shown separately.

FIG. 7A is a graph showing blood glucose levels after engrafting. The immunodeficient mice are made diabetic with streptozotocin (STZ) 7 days before engrafting. Random fed blood glucose levels are routinely checked. The blood glucose decreases to a normal level after engrafting of 1,000 7th or 15th passaged islet organoids, similar to the controls engrafting mouse 300 islets. Unengrafted diabetics remained hyperglycemic. Groups are indicated by colored lines and numbers of mice measured per group are labeled in parentheses. Data are presented as mean±s.e.m. FIG. 7N includes Vlin plots showing the comparable expression levels (Log 2(TPM+1)) of delta or PP cells markers between primary and engrafted cells.

FIGS. 8A and 8B illustrate that Procr+ cells that are devoid of endocrine marker expression are found in human islets. FIG. 8A includes representative confocal images for endocrine hormones (shown in green) and PROCR (shown in red) staining on human pancreas sections from indicated donors. Islets are outlined. Similar to mouse, human islet PROCR+ cells do not overlap with the hormone-expressing cells. Scale bar denotes 20 FIG. 8B includes representative confocal images for PROCR (shown in red) staining on human pancreas sections from indicated donors. PROCR is also expressed in the exocrine compartment of human pancreas. Scale bar denotes 20 μm.

FIG. 9A includes a representative FACS profile for TSQ staining in Hu0124 donor. Three different levels of TSQ staining are gated. FIG. 9B includes representative confocal images for the endocrine markers INS/GCG or exocrine markers AMY/KRT19 staining (shown in red) in each indicated cell population sorted from Hu0124 donor. TSQ-high cells are enriched for the islet hormone-expressing cells while the exocrine cells are TSQ-low or TSQ-neg. Scale bar denotes FIG. 9C includes FACS profiles for TSQ staining in different donors.

FIGS. 10A-10D illustrate screening for factors that promote growth of human islet organoids. FIG. 10A includes representative bright field images of organoids annotated to show the number of organoids cultured from donor Hu1021 under each indicated condition and a graph quantifying organoid size. FIG. 10B includes representative bright field images of organoids annotated to show the number of organoids cultured from donor Hu1130 under each indicated condition and a graph quantifying organoid size. FIG. 10C includes a graph quantifying organoid size that is annotated to show the number of organoids cultured from donor Hu0228 under each indicated condition. Data for FIGS. 10A-10C are presented as mean±s.e.m. FIG. 10D is a representative confocal image for the endocrine markers INS (shown in red) and GCG (shown in green) staining in organoid from Hu1130 donor. Scale bars for FIGS. 10A, 10B, and 10D denote 20 μm.

FIGS. 11A-11D depict establishing a 3D culture system to expand human islet organoids. FIG. 11A is a graph showing the number of primary passage organoids formed per 10,000 TSQ-high pancreas cells from 3 different donors. FIG. 11B include representative bright field images for islet organoids from Hu0228 donor, culture days are labeled in parentheses. Representative ductal organoid with distinguished hollow structure is also shown for comparison. Scale bar denotes 100 FIG. 11C includes graphs showing the sizes and growth curve of islet organoids (derived from primary Hu0408 donor) followed from passage 1 to passage 7. Data are presented as mean±s.e.m. FIG. 11D includes representative bright field images for islet organoids (Org) of each indicated passage cultured from Hu0408 donor. Culture days are in parentheses. Scale bar denotes 100 μm.

FIGS. 12A-12E illustrate that human islet organoids can express insulin, respond to glucose stimulation, and contain different endocrine cell types. FIG. 12A includes representative confocal images for insulin staining in islet organoids (Org) of indicated passages (culture days are in parentheses) from donor Hu0228. FIG. 12B includes representative confocal images for insulin staining in islet organoids (Org) of indicated passages (culture days are in parentheses) from donor Hu0408. For FIGS. 12A and 12B, Insulin $(INS)^+\beta$-like cells dominate in islet organoids, while glucagon $(GCG)^+$ α-like cells occur at lower frequencies. No SOX9 (duct cell marker) expression was detected in islet organoids. Scale bar denotes 20 FIG. 12C is a representative confocal image of SOX9 staining in ductal organoid. Scale bar denotes 20 FIG. 12D is a graph showing representative population measurements of dynamic normalized Fluo-4 fluorescence intensity for the 1st islet organoids (from Hu0228 donor) challenged sequentially with 2, 20, 2, 20, 2, and 20 mM glucose. The x axis represents time. FIG. 12E includes representative confocal images for INS staining in 3rd and 6th passage islet organoids from Hu0228 or Hu0408 donors. Scale bar denotes 20 μm.

FIG. 13A includes representative confocal images for EdU staining 3rd and 6th passage islet organoids from Hu0228 or Hu0408 donors. Scale bar denotes 20 FIG. 13B is a graph of a FACS analysis of $PROCR^+$ cells percentage in the 1st islet organoids culture from Hu0228 donor. FIG. 13C includes representative confocal images for EdU staining and quantification of $EdU^+$ cell percentages in PROCR+/PROCR– cells sorted from the islet organoids. $PROCR^+$ organoid cells are significantly more proliferative than PROCR– organoid cells. Scale bar denotes 20 μm.

(FIGS. 14A-14B) t-SNE plots of 20,660 human and 7,051 mouse pancreatic single cell (sc) RNAseq profiles (points), colored by cluster assignment and annotated post hoc. Both integrated (FIG. 14A) and split (FIG. 14B) view are shown. The islet progenitor population is circled in turquoise. Cell number of each cluster is shown in bracket in (FIG. 14B). Cells are pooled from n=3 biological replicates for mouse and 8 datasets for human. quie., quiescent. act., active. endo., endothelial. (FIG. 14C) Individual genes t-SNE plots showing the expression levels and distribution of representative marker genes for each cell type. The colors ranging from gray to blue indicate low to high relative gene expression levels. (FIG. 14D) Heat map of cell type-enriched genes. Each column represents a single cell and each row represents one signature gene. The colors ranging from purple to yellow indicate low to high relative gene expression levels. The marker genes of the islet progenitors are shown in the turquoise box in left. quie., quiescent. (FIG. 14E) Individual genes Vlin plots showing the expression levels (Log 2(TPM+1)) of the representative islet progenitor marker genes across different cell clusters. (FIG. 14F)

Developmental trajectory of the islet progenitor, α and β cells produced by Monocle 2. The colors in the upper panel denote cell types. Pseudotime (arbitrary units) is depicted from dark to light blue (bottom panel).

Figure 15A:
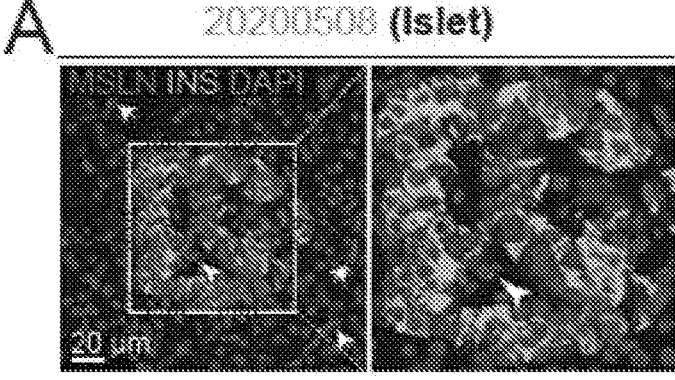
Figure 15B:
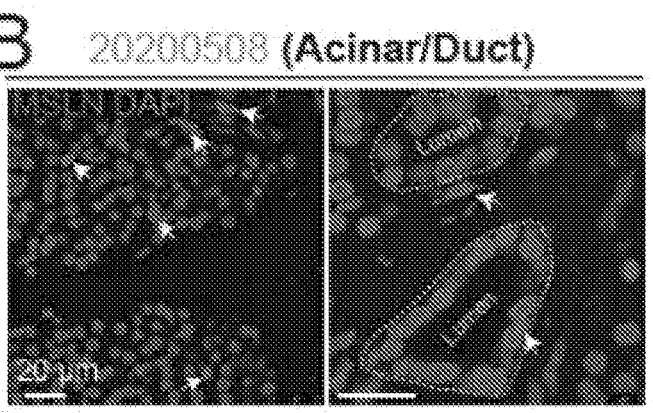
Figure 15C:
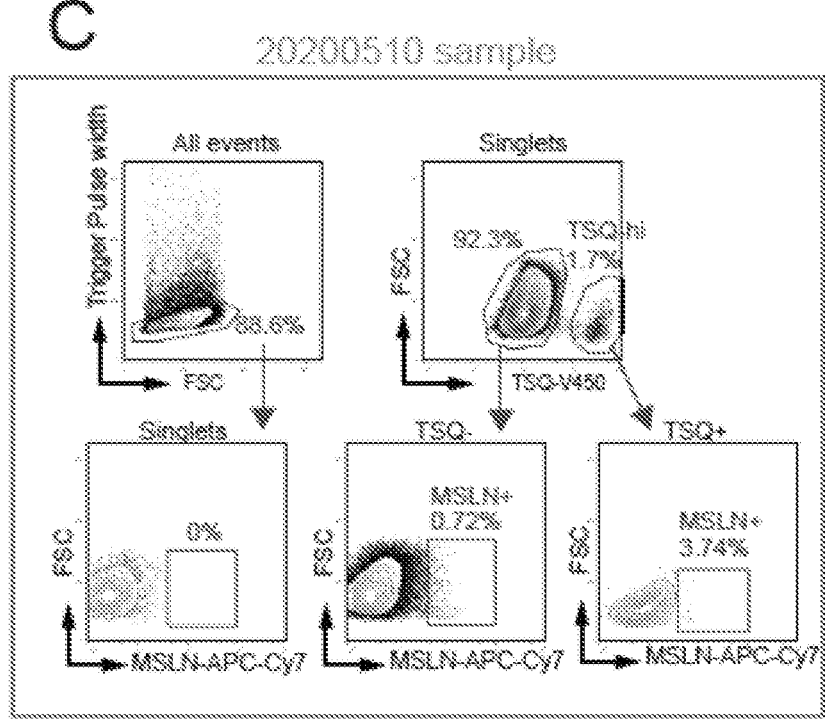
Figure 15D:
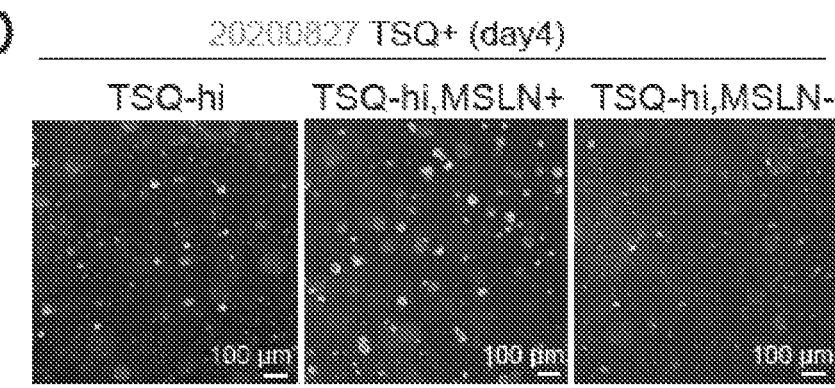
Figure 15E:
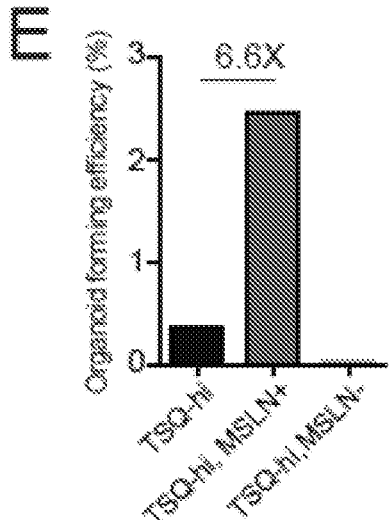

FIGS. 15A-15F. MSLN+ islet cells are adult human islet progenitors with organoid forming capacity. (FIGS. 15A-15B) Immunofluorescence staining of MSLN-expressing cells in human pancreas sections. The islet compartment is distinguished based on insulin staining in green color. The ductal region is outlined based on the lumen structure. MSLN antibody staining is shown in red color. The MSLN+ cells are a small subpopulation resided within islets (FIG. 15A). There are some of MSLN+ cells exist outside the islets (FIG. 15B). Scale bar=20 μm. (FIG. 15C) FACS analysis of MSLN-expressing cells in human pancreas. The doublets are removed based on trigger pulse width of the cells. In the TSQ+ islet epithelial compartment, ~4% of cells are MSLN+. In the TSQ– non-islet compartment, ~1% of cells are MSLN+. n=2 human samples are analyzed. The antibody-unstained samples are shown as control for APC-Cy7. (FIGS. 15D-15E) Total TSQ-hi cells, or TSQ-hi, MSLN+ cells or TSQ-hi, MSLN– cells are FACS sorted and cultured into islet organoids. Representative images in culture day 4 are shown (FIG. 15D). TSQ-hi, MSLN+ cells have the highest organoid forming efficiencies, with 6.6-fold higher than total TSQ-hi cells, whereas MSLN– cells can barely form organoids (FIG. 15E). (FIG. 15F) FACS analysis of day 14 organoids showing that most majority of MSLN+ cells is PROCR+.

FIGS. 16A-16C. Coculture with endothelial cells promotes human islet organoid growth in vitro. (FIG. 16A) Time-lapse images (culture day 0 to day 10) of human islet organoids derived from TSQ-hi islet cells. (FIG. 16B) Time-lapse images (culture day 0 to day 10) of human islet organoids derived from coculture of TSQ-hi islet cells and endothelial cells (ECs, arrows). The representative image of the day 10 organoid released from gel is also shown. (FIG. 16C) The quantification of organoid sizes showing EC coculture promotes organoid growth. ***P<0.001.

DETAILED DESCRIPTION

It has generally proven challenging to produce functional β-cells in vitro. The present disclosure is based on the discovery of a novel cell population in adult mouse and human pancreatic islets that express Protein C receptor (Procr). These $Procr^+$ cells do not express differentiation markers and feature epithelial-to-mesenchymal transition (EMT) characteristics. $Procr^+$ cells comprise approximately 1-3% of islet cells, and Procr expression allows sorting of these cells from islets. Isolated mouse $Procr^+$ cells can robustly form islet-like organoids when cultured at clonal density with endothelial cells (ECs), while human islet cells do not require ECs to form organoids. Exponential expansion can be maintained in vitro over long-time periods by serial passaging, and differentiation can be induced at any time point in culture. (3-cells are predominant in $Procr^+$ progenitor cell-derived differentiated islet organoids, while α-, δ-, and pancreatic polypeptide (PP) cells occur at lower frequencies. The $Procr^+$ progenitor cell-derived organoids are glucose-responsive and insulin-secreting. Upon transplantation in diabetic subjects, these organoids reverse disease. The findings disclosed herein demonstrate that the adult pancreas islet contains a population of $Procr^+$ endocrine cells with progenitor-like capacity.

Definitions

For convenience, certain terms employed herein, in the specification, examples and appended claims are collected here. Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

"Procr" and "PROCR" are used interchangeably and refer to protein C receptor, with "Procr" generally referring to the gene or mRNA and "PROCR" the protein product unless otherwise noted. It should be understood that the terms include the complete gene, the cDNA sequence, the complete amino acid sequence, or any fragment or variant thereof.

An "antibody," as used herein is a protein consisting of one or more polypeptides comprising binding domains that bind to a target epitope. The term antibody includes monoclonal antibodies comprising immunoglobulin heavy and light chain molecules, single heavy chain variable domain antibodies, and variants and derivatives thereof, including chimeric variants of monoclonal and single heavy chain variable domain antibodies. Binding domains are substantially encoded by immunoglobulin genes or fragments of immunoglobulin genes, wherein the protein immunospecifically binds to an antigen. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. For most vertebrate organisms, including humans and murine species, the typical immunoglobulin structural unit comprises a tetramer that is composed of two identical pairs of polypeptide chains, each pair having one "light" (about 25 kD) and one "heavy" chain (about 50-70 kD). "$V_L$" and $V_H$" refer to the variable domains of these light and heavy chains respectively. "$C_L$" and $C_H$" refer to the constant domains of the light and heavy chains. Loops of β-strands, three each on the $V_L$ and $V_H$ are responsible for binding to the antigen, and are referred to as the "complementarity determining regions" or "CDRs". The "Fab" (fragment, antigen-binding) region includes one constant and one variable domain from each heavy and light chain of the antibody, i.e., $V_L$, $C_L$, $V_H$ and $C_H1$.

Antibodies include intact immunoglobulins as well as antigen-binding fragments thereof. The term "antigen-binding fragment" refers to a polypeptide fragment of an antibody which binds antigen or competes with intact antibody (i.e., with the intact antibody from which they were derived) for antigen binding (i.e., specific binding). Antigen binding fragments can be produced by recombinant or biochemical methods that are well known in the art. Exemplary antigen-binding fragments include Fv, Fab, Fab', (Fab')$_2$, CDR, paratope and single chain Fv antibodies (scFv) in which a $V_H$ and a $V_L$ chain are joined together (directly or through a peptide linker) to form a continuous polypeptide.

Another class of antibodies known as heavy chain antibodies (HCA, also referred to as two-chain or two-chain heavy chain antibodies) have been reported in camelids such as dromedary camels, Bactrian camels, wild Bactrian camels, llamas, alpacas, vicuñas, and guanacos (Hamers-Casterman et al., Nature, 363, 446-448 (1993); Wesolowski et al., Med. Microbiol. Immunol (2009) 198:157-174; see also U.S. Pat. Nos. 5,759,808; 5,800,988; 5,840,526; and 5,874,541). Compared with conventional four-chain immunoglobulins of IgG-type, which are also produced by camelids, these antibodies lack the light chains and CH1 domains of conventional immunoglobulins, and their variable domains are sometimes designated "$V_HH$". $V_HH$ can include four framework regions or "FR", FR1, FR2, FR3 and FR4. The framework regions are interrupted by three CDRs, CDR1, CDR2 and CDR3. One of the salient features of these naturally occurring heavy chain antibodies is the predominant presence of Glu, Arg and Gly at VL interface positions 44, 45 and 47 (Kabat numbering), respectively, of their $V_HH$. The same positions in the VH of conventional four-chain antibodies (are almost exclusively occupied by Gly, Leu and Trp. These differences are thought to be responsible for the high solubility and stability of camelid HCA variable domain ($V_HH$), as compared with the relative insolubility of VH domain of the conventional four-chain antibodies. Two more salient features of camelid $V_HH$ domains are their comparatively longer CDR3 and high incidence of cysteine pairs in CDRs. It appears that cysteine pairs mediate the formation of a disulfide bridge and are therefore involved in modulating the surface topology of the antibody combining site. In the crystal structure of a camel sdAb-lysozyme complex, a rigid loop protruding from the sdAb and partly stabilized by a CDR disulfide linkage extends out of the combining site and penetrates deeply into the lysozyme active site (Desmyter et al., Nature Struct. Biol., 3, 803-811 (1996)).

Antibodies also include variants, chimeric antibodies and humanized antibodies. The term "antibody variant" as used herein refers to an antibody with single or multiple mutations in the heavy chains and/or light chains. In some embodiments, the mutations exist in the variable region. In some embodiments, the mutations exist in the constant region. "Chimeric antibodies" refers to those antibodies wherein one portion of each of the amino acid sequences of heavy and light chains is homologous to corresponding sequences in antibodies derived from a particular species or belonging to a particular class, while the remaining segment of the chains is homologous to corresponding sequences in another. Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations.

While the variable region has the advantage of ease of preparation, and the specificity is not affected by its source, the constant region being human, is less likely to elicit an immune response from a human subject when the antibodies are injected than would the constant region from a non-human source. However, the definition is not limited to this particular example. "Humanized" antibodies refer to a molecule having an antigen-binding site that is substantially derived from an immunoglobulin from a non-human species and the remaining immunoglobulin structure of the molecule based upon the structure and/or sequence of a human immunoglobulin. The antigen-binding site may comprise either complete variable domains fused onto constant domains or only the complementarity determining regions (CDRs) grafted onto appropriate framework regions in the variable domains. Antigen binding sites may be wild type or modified by one or more amino acid substitutions, e.g., modified to resemble human immunoglobulin more closely. Some forms of humanized antibodies preserve all CDR sequences (for example, a humanized mouse antibody which contains all six CDRs from the mouse antibodies). Other forms of humanized antibodies have one or more CDRs (one, two, three, four, five, or six) which are altered with respect to the original antibody, which are also termed one or more CDRs "derived from" one or more CDRs.

An "anti-PROCR antibody" is an antibody that immuno-specifically binds to PROCR (e.g., its extracellular domain). The antibody may be an isolated antibody. Such binding to PROCR exhibits a $K_d$ with a value of, e.g., no greater than 1 µM, no greater than 100 nM or no greater than 50 nM. Kd can be measured by any methods known to a skilled in the art, such as a surface plasmon resonance assay or a cell binding assay. An anti-PROCR antibody may be a mono-clonal llama antibody, e.g., GS5, GS4, GS2, HD13, HD21, HD44, HD58 or HD61 disclosed in PCT/CN2017/115198, or antigen-binding fragments thereof. Exemplary anti-PROCR antibodies inhibit PROCR binding with protein C. The anti-PROCR antibody may also be the "RCR-252" antibody, which refers to the monoclonal antibody having clone number RCR-252 as first described in Ye et al., "The endothelial cell protein C receptor (EPCR) functions as a primary receptor for protein C activation on endothelial cells in arteries, veins, and capillaries," Biochem Biophys Res Commun 1999, 259: 671. RCR-252 is a rat anti human PROCR antibody, and is commercially available from mul-tiple sources, such as Abcam under Catalog No. ab81712 and Sigma under Product No. E6280. In some embodiments, an anti-PROCR antibody can be those disclosed in US20190045758 or PCT/CN2017/115198, incorporated herein by reference in their entirety. Other commercially available anti-PROCR antibodies can also be used, includ-ing those disclosed herein.

As used herein, the term "adult cell" refers to a cell found throughout the body after embryonic development.

The term "pancreas" refers to a glandular organ that secretes digestive enzymes and hormones. In humans, the pancreas is a yellowish organ about 7 in. (17.8 cm) long and 1.5 in. (3.8 cm) wide. It lies beneath the stomach and is connected to the small intestine, muscular hoselike portion of the gastrointestinal tract extending from the lower end of the stomach (pylorus) to the anal opening. Most of the pancreatic tissue consists of grapelike clusters of cells that produce a clear fluid (pancreatic juice) that flows into the duodenum through a common duct along with bile from the liver. Pancreatic juice contains three digestive enzymes: tryptase, amylase, and lipase, that, along with intestinal enzymes, complete the digestion of proteins, carbohydrates, and fats, respectively. Scattered among the enzyme-produc-ing cells of the pancreas are small groups of endocrine cells, called the islets of Langerhans, that secrete two hormones, insulin and glucagon. The pancreatic islets contain several types of cells: α cells, which produce the hormone glucagon; β cells (also referred to herein as "pancreatic β cells"), which manufacture the hormone insulin; and δ-cells, which pro-duce the regulatory agent somatostatin. These hormones are secreted directly into the bloodstream, and together, they regulate the level of glucose in the blood. Insulin lowers the blood sugar level and increases the amount of glycogen (stored carbohydrate) in the liver; glucagon has the opposite action. Failure of the insulin-secreting cells to function properly results in diabetes or diabetes mellitus.

The terms "progenitor" and "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have signifi-cant or very high proliferative potential. Progenitor cells can give rise to multiple distinct differentiated cell types or to a single differentiated cell type, depending on the develop-mental pathway and on the environment in which the cells develop and differentiate.

The terms "pancreatic endocrine progenitor" and "endo-crine progenitor" are used interchangeably herein and refer to a progenitor cell which is capable of becoming a pancre-atic hormone expressing cell or capable of forming pancre-atic endocrine cells. In some embodiments, such progenitor cells are isolated from adult islets and are Procr$^+$, i.e., expressing Procr mRNA and/or protein. In some embodi-ments, such progenitor cells are MSLN$^+$, i.e., expressing MSLN mRNA and/or protein.

As used herein, the term "insulin-producing cell" refers to a cell differentiated from a pancreatic endocrine progenitor, or precursor thereof, which secretes insulin. An insulin-producing cell includes pancreatic β cells as that term is described herein, as well as pancreatic β-like cells (i.e., insulin-positive, endocrine cells) that synthesize (i.e., tran-scribe the insulin gene, translate the proinsulin mRNA, and modify the proinsulin mRNA into the insulin protein), express (i.e., manifest the phenotypic trait carried by the insulin gene), or secrete (release insulin into the extracellular space) insulin in a constitutive or inducible manner. A population of insulin-producing cells e.g. produced by dif-ferentiating insulin-positive, endocrine cells or a precursor thereof into β cells according to the methods of the present disclosure can be pancreatic β cells or β-like cells (e.g., cells that have at least one, or at least two) characteristic of an endogenous β cell and exhibit a GSIS response that resembles an endogenous adult β cell. The novelty of the present composition and methods is not negated by the presence of cells in the population that produce insulin naturally (e.g., β cells). It is also contemplated that the population of insulin-producing cells, e.g. produced by the methods as disclosed herein can comprise mature pancreatic β cells, and can also contain non-insulin-producing cells (i.e. cells of β cell like phenotype with the exception they do not produce or secrete insulin).

In the context of cell ontogeny, the adjective "differenti-ated", or "differentiating" is a relative term meaning a "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as a cardiomyocyte precursor), and then to an end-stage differentiated cell, which plays a characteristic role in a certain tissue type, and may or may not retain the capacity to proliferate further.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art. An exemplary basal medium used herein include DMEM/F-12 (Dulbecco's Modified Eagle Medium/Nutrient Mixture F-12; available from Thermo Fisher Scientific). A basal medium can be supplemented with one or more of: suitable buffer (e.g., HEPES (4-(2-hydroxyethyl)-1-piperazineethanesulfonic acid)), chemically-defined supplements such as N2 (0.1-10%, e.g., 1%) and B27 (0.1-10%, e.g., 1%) serum-free supplements (available from Thermo Fisher Scientific), antibiotics such as penicillin/streptomycin (0.1-10%, e.g., 1%), MEM non-essential amino acids (Eagle's minimum essential medium (MEM) which is composed of balanced salt solutions, amino acids and vitamins that are essential for the growth of cultured cells, which, when supplemented with non-essential amino acids, makes MEM non-essential amino acid solution), glucose (0.1-10%, e.g., 0.30%), L-glutamine (e.g., GlutaMAX™), ascorbic acid, and/or DAPT (N—[N-(3,5-difluorophenacetyl)-1-alanyl]-S-phenylglycine t-butyl ester). Factors for inducing differentiation such as Wnt agonist such as CHIR99021 or Wnt surrogate such as NGS, TGF-beta pathway inhibitors such as SB431542 or A83-01, Rho-ROCK pathway inhibitor such as Y27632, Bmp inhibitor such as Noggin, EGF (epidermal growth factor), insulin transferrin selenium mixture (ITS, available from Sigma), FGF2 (fibroblast growth factor 2), Heparin, Y27632 and B27 as disclosed herein can also be added to the medium.

The term "cell line" refers to a population of largely or substantially identical cells that has typically been derived from a single ancestor cell or from a defined and/or substantially identical population of ancestor cells. The cell line may have been or may be capable of being maintained in culture for an extended period (e.g., months, years, for an unlimited period of time). It may have undergone a spontaneous or induced process of transformation conferring an unlimited culture lifespan on the cells. Cell lines include all those cell lines recognized in the art as such. It will be appreciated that cells acquire mutations and possibly epigenetic changes over time such that at least some properties of individual cells of a cell line may differ with respect to each other. In some embodiments, a cell line comprises a Procr+ endocrine progenitor described herein.

By "organoid" is meant a three-dimensional multicellular in vitro construct that mimics, to some extent, an in vivo organ. For example, a pancreatic organoid comprises cells that mimic the function of islet cells. "Mature organoid" as used herein refers to an organoid that been cultured in a differentiation medium. Mature organoids, in some embodiments, have gene expression signatures similar or identical to the organ that they mimic.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences.

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The term "substantially pure", with respect to a particular cell population, refers to a population of cells that is at least about 75%, preferably at least about 85%, more preferably at least about 90%, and most preferably at least about 95% pure, with respect to the cells making up a total cell population. Recast, the terms "substantially pure" or "essentially purified", with regard to a population of Procr+ endocrine progenitor cells, refers to a population of cells that contain fewer than about 20%, more preferably fewer than about 15%, 10%, 8%, 7%, most preferably fewer than about 5%, 4%, 3%, 2%, 1%, or less than 1%, of cells that are not Procr+ endocrine progenitor cells as defined by the terms herein. In some embodiments, the present disclosure encompasses methods to expand a population of Procr+ endocrine progenitor cells, wherein the expanded population of Procr+ endocrine progenitor cells is a substantially pure population of Procr+ endocrine progenitor cells.

The terms "enriching" or "enriched" are used interchangeably herein and mean that the yield (fraction) of cells of one type is increased by at least 10% over the fraction of cells of that type in the starting culture or preparation.

The terms "renewal" or "self-renewal" or "proliferation" are used interchangeably herein, are used to refer to the ability of stem cells or progenitor cells to renew themselves by dividing into the same non-specialized cell type over long periods, and/or many months to years. In some instances, proliferation refers to the expansion of cells by the repeated division of single cells into two identical daughter cells.

The terms "diabetes" and "diabetes mellitus" are used interchangeably herein. The World Health Organization defines the diagnostic value of fasting plasma glucose concentration to 7.0 mmol/1 (126 mg/dl) and above for Diabetes Mellitus (whole blood 6.1 mmol/1 or 110 mg/dl), or 2-hour glucose level 11.1 mmol/L or higher (200 mg/dL or higher). Other values suggestive of or indicating high risk for Diabetes Mellitus include elevated arterial pressure 140/90 mm Hg or higher; elevated plasma triglycerides (1.7 mmol/L; 150 mg/dL) and/or low HDL-cholesterol (less than 0.9 mmol/L, 35 mg/dl for men; less than 1.0 mmol/L, 39 mg/dL women); central obesity (males: waist to hip ratio higher than 0.90; females: waist to hip ratio higher than 0.85) and/or body mass index exceeding 30 kg/m$^2$; microalbuminuria, where the urinary albumin excretion rate 20 μg/min or higher, or albumin:creatinine ratio 30 mg/g or higher). The term diabetes encompasses all forms of diabetes, e.g. Type I, Type II and Type 1.5.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

As used herein, the term "treating" and "treatment" refers to administering to a subject an effective amount of a composition so that the subject as a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. As used herein, the term "treatment" includes prophylaxis. Alternatively, treatment is "effective" if the progression of a disease is reduced or halted. "Treatment" can also mean prolonging survival as compared to expected survival if not receiving treatment. Those in need of treatment include those already diagnosed with a cardiac condition, as well as those likely to develop a cardiac condition due to genetic susceptibility or other factors such as weight, diet and health.

As used herein, the terms "administering," "introducing" and "transplanting" are used interchangeably in the context of the placement of cells, e.g., pancreatic organoids) of the present disclosure into a subject, by a method or route which results in at least partial localization of the introduced cells at a desired site. The cells (e.g., pancreatic organoids, pancreatic β cells or pancreatic β-like cells) can be implanted directly to the pancreas, or alternatively be administered by any appropriate route which results in delivery to a desired location in the subject where at least a portion of the implanted cells or components of the cells remain viable. The period of viability of the cells after administration to a subject can be as short as a few hours, e.g. twenty-four hours, to a few days, to as long as several years. In some instances, the cells can also be administered at a non-pancreatic location, such as in the liver or subcutaneously, for example, in a capsule (e.g., microcapsule) to maintain the implanted cells at the implant location and avoid migration of the implanted cells.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth.

Various aspects and embodiments are described in further detail in the following subsections. Any compositions or methods provided herein can be combined with one or more of any of the other compositions and methods provided herein.

Procr$^+$ Endocrine Progenitor Cells

It has been surprisingly discovered that Procr$^+$ endocrine progenitor cells reside in the adult pancreas as a small subset (about 1-3%) of cells present in islets. Procr is a Wnt target gene that encodes a protein residing on the surface of the endocrine progenitor cells. The human PROCR is a highly glycosylated type I transmembrane protein of 238 amino-acids (UniProtKB ID No. Q9UNN8). These amino acids comprise a signal peptide (amino acids 1017), an extracellular domain (amino acids 18-210), a 21-aa transmembrane domain (amino acids 211-231), and a 7-aa intracytoplasmic sequence (amino acids 232-238) together coding for an ~46 kDa protein. Deglycosylation will reduce the protein mass to 25 kDa.

PROCR is the receptor for protein C, a key player in the anticoagulation pathway. The protein C anticoagulant pathway serves as a major system for controlling thrombosis, limiting inflammatory responses, and potentially decreasing endothelial cell apoptosis in response to inflammatory cytokines and ischemia. The essential components of the pathway include thrombin, thrombomodulin, PROCR, protein C and protein S. The pathway is initiated when thrombin binds to thrombomodulin on the surface of endothelium. PROCR augments protein C activation by binding protein C and presenting it to the thrombin-thrombomodulin activation complex. Activated protein C (aPC) retains its ability to bind PROCR, and this complex appears to be involved in some of the cellular signaling mechanisms that down-regulate inflammatory cytokine formation (TNF, IL-6). PROCR is shed from the vasculature by inflammatory mediators and thrombin. PROCR binds to activated neutrophils in a process that involves proteinase 3 and Mac-1.

PROCR can be cleaved to release a soluble form (sPROCR) in the circulation. This sPROCR is detected as a single species of 43 kDa, resulting from shedding of membrane PROCR by the action of a metalloprotease, which is stimulated by thrombin and by some inflammatory mediators. Soluble PROCR binds PC and aPC with similar affinity, but its binding to aPC inhibits the anticoagulant activity of aPC by blocking its binding to phospholipids and by abrogating its ability to inactivate factor Va. sPROCR can be detected in plasma. In normal persons, sPROCR is present in levels of 83.6+/−17.2 ng/ml. Elevated levels of sPROCR are positively correlated to a higher risk for thrombosis. Furthermore, a haplotype (A3 allele) has been linked to elevated levels of sPROCR (264+/−174 ng/ml).

The full gene sequence of human Procr is 44819 bp (GenBank ID No. NC_000020.11). The human cDNA sequence is 717 bp in length (GenBank ID No. NM_006404.4). The full gene sequence of mouse Procr gene is 4354 bp (GenBank ID No. NC_000068.7).

In some embodiments, Procr$^+$ cells isolated from mouse pancreas can express R-spondin 1 (Rspo1), Fibroblast growth factor 1 (Fgf1), Uroplakin 3B (Upk3b), Homeobox A5 (Hoxa5) and Mesothelin (Msln) (as well as other genes shown in FIG. 2F), and the expression of these genes constitutes a unique, and previously unreported, expression signature for these progenitor cells. These Procr$^+$ progenitor cells can exhibit EMT characteristics. In some embodiments, the EMT characteristics include co-expression of epithelial markers EpCam, Krt8, and Cldn10 and mesenchymal markers Mmp2, Col1a1, and Vim. EMT plays a pivotal role during pancreatic islet formation. Committed endocrine precursor cells detach from the trunk epithelium, presumably via EMT, before the formation of the endocrine islets. It has also been proposed that at later stages ductal cells can serve as facultative endocrine progenitors, which is thought to happen through reawakening of the embryonic EMT process. Under specific culture conditions, β-cells can undergo EMT and dedifferentiate, thereby losing their mature characteristics. The resultant fibroblast-like cells can be extensively expanded and re-differentiated into endocrine cell types.

Procr$^+$ cells descend from Ngn3$^+$ cells, which appear to be in a partial EMT state, co-expressing epithelial markers and mesenchymal markers. Ngn3$^+$ cells exist within the embryonic endocrine precursor cell population, with similar EMT characteristic and shared signature genes such as Procr, Rspo1, Hoxa5, and Decorin (Dcn). The Ngn3$^+$ endocrine precursor represents a transient cell type in the embryonic pancreas. While the majority of Ngn3$^+$ endocrine precursors lose their precursor state after maturation into endocrine cells, it appears likely that a subpopulation is retained in an endocrine progenitor state post organogenesis. This reserve population does not express Ngn3, but it retains EMT features and the gene expression signature.

These Procr$^+$ cells can be isolated from the adult pancreas using the methods described herein. In various aspects of the present disclosure, Procr$^+$ endocrine progenitor cells are isolated and then cultured under conditions suitable for generating pancreatic organoids. In some embodiments, mouse Procr$^+$ endocrine progenitor cells also express one or more of Procr, Rspo1, Hoxa5 and Dcn. In some embodiments, a Procr$^+$ progenitor cell can be isolated from an islet by contacting the cell with an antibody that specifically binds Procr. In some embodiments, Procr$^+$ progenitor cells are isolated by fluorescence activated cell sorting (FACS). Other methods known in the art for isolating cells based on marker expression are contemplated herein.

MSLN$^+$ Endocrine Progenitor Cells

Another unexpected discovery is that a population of MSLN$^+$ endocrine progenitor cells reside in the adult human pancreas as a small subset (about 3-5%) of cells present in islets. In some embodiments, the endocrine progenitor cells are both Procr$^+$ and MSLN$^+$.

Mesothelin (MSLN) gene encodes a 71-KD precursor (UniProtKB ID No. Q9UNN8), which is a glycosylphosphatidylinositol (GPI)-anchored membrane glycoprotein that is cleaved into two products at arginine 295 (Arg 295): a soluble 31-KD N-terminal protein called megakaryocyte potentiating factor (MPF) and a 40-KD membrane-bound fragment called MSLN (Mesothelin). Both MPF and MSLN are bioactive, but their exact functions have remained unclear until the present disclosure. MPF functions as a cytokine that can stimulate colony formation of bone marrow megakaryocytes, while its activity is unknown in humans. MSLN was first described as a membrane protein expressed on mesothelioma and ovarian cancer cells and normal mesothelial cells.

MSLN is expressed on normal mesothelial cells in the pleura, pericardium, and peritoneum and in epithelial cells on the surface of the ovary, tunica vaginalis, rete testis, and fallopian tubes in trace amounts. In contrast, the aberrant overexpression of MSLN is observed in various cancer cells. In addition, MSLN is shed into the serum of patients with solid tumors, in which it is referred to as soluble MSLN-related protein (SMRP). The production of SMRP could be associated with abnormal splicing, which results in a secreted form or its cleavage from the membrane by the TNFα-converting enzyme ADAM17. SMRP was also identified as a cancer bio-marker in the sera of patients with mesothelioma, in which elevated SMR levels in serum was correlated with advanced stage and increased disease burden. However, the sensitivity and specificity of SMRP as a tumor marker in ovarian cancer was limited. The value of soluble MSLN in diagnosis and the prediction of cancer progression remain to be determined.

The full gene sequence of human MSLN is 8132 bp (GenBank ID No. NC_000016.10). The human MSLN cDNA sequence is 1869 bp in length (GenBank ID No. NM_005823.6) for variant 1 or 1893 bp in length (GenBank ID No. NM_013404.4) for variant 2.

The full gene sequence of mouse Msln is 5766 bp (GenBank ID No. NC_000083.6). The mouse Msln cDNA sequence is 1878 bp in length (GenBank ID No. NM_001356286.1) for variant1 or 1890 bp in length (GenBank ID No. NM_001374653.1) for variant 2.

In some embodiments, MSLN$^+$ cells isolated from human pancreas can express one or more of: UPK1B (uroplakin 1B), S100A6 (S100 calcium binding protein A6), LGALS4 (galectin 4), SDCBP2 (syndecan binding protein 2), SDC1 (syndecan 1), IGFBP3 (insulin like growth factor binding protein 3), HMGA1 (high mobility group AT-hook 1), ITGB4 (integrin subunit beta 4), ITGB6 (integrin subunit beta 6), HN1 (hematological and neurological expressed 1), GPRC5A (G protein-coupled receptor class C group 5 member A), SLP1 (secretory leukocyte peptidase inhibitor), LAMC2 (laminin subunit gamma 2), FERMT1 (fermitin family member), MGLL (monoglyceride lipase), MSLN (mesothelin), SEMA3B (semaphorin 3B), TST (thiosulfate sulfurtransferase), SFN (stratifin) and CDH3 (cadherin 3), and the expression of these genes constitutes a unique, and previously unknown, expression signature for these endocrine progenitor cells.

These MSLN$^+$ cells can be isolated from the human adult pancreas using the methods described herein. In various aspects of the present disclosure, MSLN$^+$ endocrine progenitor cells are isolated and then cultured under conditions suitable for generating pancreatic islet organoids. In some embodiments, human MSLN$^+$ endocrine progenitor cells also express one or more of UPK1B, S100A6, LGALS4, SDCBP2, SDC1, IGFBP3, HMGA1, ITGB4, ITGB6, HN1, GPRC5A, SLPI, LAMC2, FERMT1, MGLL, MSLN, SEMA3B, TST, SFN, CDH3 and PROCR. In some embodiments, a MSLN$^+$ progenitor cell can be isolated from an islet by contacting the cell with an antibody (or antigen-binding fragment thereof) that specifically binds MSLN, such as anti-human MSLN antibody (Biolegend, Cat #530203). In some embodiments, MSLN$^+$ progenitor cells can be isolated by fluorescence activated cell sorting (FACS). Other methods known in the art for isolating cells based on marker expression are contemplated herein.

Organoid Production

Identifying a reservoir of endocrine progenitor cells (e.g., Procr$^+$ and/or MSLN$^+$ endocrine cells) in the pancreas itself allows for either in situ or ex vivo expansion approach to increase β-cell mass. The expansion and differentiation capacities of the endocrine progenitors can be exploited to establish a culture system for the expansion and induction of islet-like organoids. The resulting organoids are dominated by β-cells surrounded by a mantle of α-, δ- and PP-cells, which is important for organoid function as proper glucose regulation requires coordination between the various islet cell types.

Isolated Procr$^+$ and/or MSLN$^+$ cells can be used to generate organoids that exhibit pancreatic functions (e.g., glucose sending and insulin production and secretion). In some embodiments, Procr$^+$ and/or MSLN$^+$ endocrine progenitor cells can be isolated from adult islet cells and cultured to produce the organoids of the present disclosure are derived can be obtained from any pancreatic source. For example, islet cells may be obtained from a commercial source or from a human source. In some embodiments, the source of the islet cells is a human cadaver. In some embodiments, the source of the islet cells is a human patient with abnormal pancreatic function (e.g., Type 1 or Type 2 diabetes patient, or MODY (maturity onset diabetes of the young) patient). Procr$^+$ and/or MSLN$^+$ endocrine progenitor cells present in islets obtained from a human patient can be cultured to produce organoids that comprise insulin-producing glucose sensitive islet cells (i.e., β-like cells).

In general, to form an organoid, isolated cells are first expanded. To expand cells (i.e., to form colonies of the isolated cells), the cells are cultured in an organoid medium under conditions suitable for cellular growth and reproduction. An organoid medium can be a serum-free medium supplemented with growth factors to facilitate cell growth and reproduction. In some embodiments, the organoid medium does not contain sufficient differentiation factors to cause the cells to differentiate. In some embodiments, the organoid medium contains no differentiation factors. Growth factors that can be used in an organoid medium include, but are not limited to Wnt agonists CHIR99021 or NGS, TGF-beta pathway inhibitors SB431542 or A83-01, Rho-ROCK pathway inhibitor Y27632, Bmp inhibitor Noggin, EGF (epidermal growth factor), ITS, FGF2 (fibroblast growth factor 2), Heparin, activating antibodies of Integrin beta 1, and B27. Additionally, growth-promoting conditions can include any condition (e.g., culture media, incubation time, frequency of media changes, and the like) that activates the Wnt, FGF, integrin and/or BMP signaling pathways. Growth promoting conditions can require inhibition of other cellular signaling pathways. For example, in some embodiments, growth promoting conditions can include inhibiting the TGFβ and/or Rho-ROCK pathways.

One exemplary organoid medium for culturing mouse cells is DMEM/F12 (with Penicillin-Streptomycin) plus 1-5% (e.g., 2%) B27, 0.1-5% (e.g., 1%) ITS, 10-200 (e.g., 50) ng ml$^{-1}$ EGF, 0.1-5 (e.g., 2) μg ml$^{-1}$ heparin, 1-50 (e.g., 10) ng ml$^{-1}$ FGF2 and 1-20 (e.g., 5) ng ml$^{-1}$ VEGFa. Another exemplary organoid medium for culturing human cells is DMEM/F12 (with Penicillin-Streptomycin) plus 1-5% (e.g., 2%) B27, 0.1-5% (e.g., 1%) ITS, 10-200 (e.g., 50) ng ml$^{-1}$ EGF, 0.1-5 (e.g., 2) μg ml$^{-1}$ heparin, 1-50 (e.g., 10) ng ml$^{-1}$ FGF2, 1-10 (e.g., 3) μM CHIR99021, 1-10 (e.g., 2) μM A83-01, 10-500 (e.g., 100) ng ml$^{-1}$ Noggin, 1-50 (e.g., 10) μM Y27632.

Isolated progenitor cells can be cultured in a microenvironment that mimics at least, in part, a cellular niche in which the cells naturally reside. The cellular niche can be mimicked by culturing the stem cells in the presence of biomaterials, such as matrices, scaffolds, and culture substrates that represent key regulatory signals controlling cell fate. The biomaterials can be natural, semi-synthetic and synthetic biomaterials, and/or mixtures thereof. A scaffold provides a two-dimensional or three-dimensional network. Suitable synthetic materials for the scaffold include polymers selected from porous solids, nanofibers, and hydrogels, such as peptides including self-assembling peptides, hydrogels composed of polyethylene glycol phosphate, polyethylene glycol fumarate, polyacrylamide, polyhydroxyethyl methacrylate, polycellulose acetate, and/or co-polymers thereof (see, for example, Saha et al., 2007, *Curr. Opin. Chem. Biol.* 11(4): 381-387; Saha et al., 2008, *Biophysical Journal* 95: 4426-4438; Little et al., 2008, *Chem. Rev.* 108, 1787-1796). As is known to a skilled person, the mechanical properties such as the elasticity of the scaffold influences proliferation, differentiation and migration of stem cells. A preferred scaffold comprises biodegradable (co)polymers that are replaced by natural occurring components after transplantation in a subject, for example to promote tissue regeneration and/or wound healing. It is furthermore preferred that the scaffold does not substantially induce an immunogenic response after transplantation is a subject. the scaffold can be supplemented with natural, semi-synthetic or synthetic ligands, which provide the signals that are required for proliferation and/or differentiation, and/or migration of stem cells. In a preferred embodiment, the ligands comprise defined amino acid fragments. Examples of the synthetic polymers comprise Pluronic® F127 block copolymer surfactant (BASF), and Ethisorb® (Johnson and Johnson).

A cellular niche is in part determined by the progenitor cells and surrounding cells, and the extracellular matrix (ECM) that is produced by the cells in the niche. In some embodiments, isolated cells are attached to an ECM. ECM is composed of a variety of polysaccharides, water, elastin, and glycoproteins, wherein the glycoproteins comprise collagen, entactin (nidogen), fibronectin, and laminin. ECM is secreted by connective tissue cells. Different types of ECM are known, comprising different compositions including different types of glycoproteins and/or different combination of glycoproteins. The ECM can be provided by culturing ECM-producing cells, such as fibroblast cells, in a receptacle, prior to the removal of these cells and the addition 20 of isolated progenitor cells. Examples of extracellular matrix-producing cells are chondrocytes, producing mainly collagen and proteoglycans, fibroblast cells, producing mainly type IV collagen, laminin, interstitial procollagens, and fibronectin, and colonic myofibroblasts producing mainly collagens (type I, III, and V), chondroitin sulfate proteoglycan, hyaluronic acid, fibronectin, and tenascin-C. Alternatively, the ECM can be commercially provided. 25 Examples of commercially available extracellular matrices are extracellular matrix proteins (Invitrogen) and basement membrane matrix MATRIGEL™ (BD Biosciences). The use of an ECM for culturing progenitor cells enhanced long-term survival of the cells and the continued presence of undifferentiated cells. In addition, the presence of an ECM allows culturing of three-dimensional tissue organoids.

A suitable ECM for use can include, in some embodiments, at least two distinct glycoproteins, such as two different types of collagen or a collagen and laminin. The ECM can be a synthetic hydrogel extracellular matrix or a naturally occurring ECM. An exemplary ECM is provided by basement membrane matrix MATRIGEL™ (BD Biosciences), which comprises laminin, entactin, and collagen IV.

In some embodiments, isolated Procr$^+$ and/or MSLN$^+$ cells can be co-cultured with endothelial cells at a ratio of about 1:10 to about 10:1, e.g., about 1:5, about 1:3, or about 1:1. Endothelial cells provide a critical niche component, and in some embodiments, the co-culture medium is supplemented with VEGFa.

Organoids can be passaged every 5-30 days to expand. For passage, organoids can be released from the basement membrane matrix MATRIGEL™ using dispase and dissociated into single cells (e.g., with trypsin-EDTA). The single cell suspension can then be mixed with freshly isolated CD31+ECs in a ratio of 1:1, followed by replating in a split ratio of about 1:2-1:10, or about 1:3-1:8, or about 1:4-1:6. Organoids can be passaged at least 20 times (about 6 months), at least 30 times, or indefinitely, with no deceleration of expansion rate.

This duration of expansion provides time for organoids to mature such that β-like cells are capable of producing and secreting insulin in response to a glucose stimulus. Then these passaged organoids can be taken out of expansion cycle and allowed to mature for an additional period of time (e.g., about 1-4 weeks or about 2-3 weeks or about 3 weeks (28-30 days upon being replated as single cells), mature organoids can appear that resemble the primary organoids. In some embodiments, organoids are tested to determine their capacity to produce and secrete insulin. In some embodiments, the testing is performed in vitro. In some embodiments, the testing is performed in vivo, for example, after an organoid is transplanted into a recipient (e.g., a mouse or human). Insulin production and/or secretion in or by an organoid can be assessed by any technique known in the art. For example, the expression of insulin can be assessed by enzyme-linked immunosorbent assay (ELISA) or other immunoassay that utilizes an antibody that specifically binds insulin (or another molecule of interest expressed in the organoid, including but not limited to glucagon, somatostatin, and pancreatic polypeptide. In some embodiments, detection of insulin production in an organoid can be assessed in vitro by obtaining at least one organoid in a culture and testing it directly. Insulin secretion by an organoid can be detected in vitro in the culture medium by any means known in the art. For example, a culture may be spun down and the organoid-free (or substantially free) supernatant tested for insulin. In some embodiments, in vivo insulin production by transplanted organoids can be assessed via analysis of a blood draw from a subject having received treatment with organoids of the present disclosure and compared to insulin levels in the subject prior to treatment. Such measurements are routine in the art.

Use of Insulin Producing Organoids

Organoids derived from Procr$^+$ and/or MSLN$^+$ endocrine progenitor cells, such as those organoids described herein or organoids produced using the methods described herein are useful as therapeutics and prophylactics for the treatment and prevention of diabetes mellitus (DM), or any disease or condition that is responsive to the presently described insulin producing organoids.

The number of the organoids described herein in the pharmaceutical composition necessary to achieve an optimal or satisfactory result may vary between subjects being treated. For example, the number of organoids necessary for a person with a complete loss of endogenous insulin production will likely be less than the amount of organoids necessary for a patient who has retained at least some endogenous insulin production. In some embodiments, the number of organoids present in the pharmaceutical composition can be between about 100 to about 10,000,000 organoids, about 1,000-1,000,000 organoids, or about 10,000-100,000 organoids, or any number smaller, larger or there between. Determining the precise effective dose may be based on factors for each individual subject, including their size, age, sex, weight, and condition. Dosages can be readily ascertained by those skilled in the art from this disclosure and the knowledge in the art. The skilled artisan can also readily determine the number of organoids and the amount of optional additives, vehicles, and/or carriers in compositions and to be administered in methods of the invention.

The present disclosure features compositions and methods that are useful for therapeutic approaches for treating diabetes. More specifically, the organoids described above are administered to those in need (e.g., a human diabetic), which can ameliorate, reduce, or otherwise treat or prevent a patient's abnormal pancreatic function. In some embodiments, the organoids are derived from endocrine progenitor cells obtained from the patient, optionally followed by correcting mutations (if any) by gene editing such as CRISPR. Obtaining autologous islet cells from the patient lessens the risk of rejection of the organoids when administered to the patient. In some embodiments, the organoids are derived from endocrine progenitor cells obtained from a heterologous human subject (such as a bank or library of organoids).

The administration of the organoids of the present disclosure for the treatment of diabetes (or any other disease or condition that may be responsive to the organoids) may be by any suitable means that results in a concentration of the therapeutic organoid that is effective in ameliorating, treating, or preventing diabetes.

In some embodiments, the organoids are transplanted directly into the patient's pancreas or another locus in the body, such as liver, spleen, renal capsule, omental pouch, skin, muscle, bone marrow (see, e.g., doi: 10.3389/fmed.2018.00202, incorporated herein by reference). The subject may also be administered anti-rejection medication to less the probability that the transplanted organoids are rejected by the patient's immune system.

In one aspect, the invention provides a method of monitoring treatment progress. The method includes the step of determining a level of insulin (or other marker (e.g., glucagon, somatostatin, or pancreatic polypeptide) or diagnostic measurement (e.g., screen, assay) in a subject suffering from or susceptible to diabetes or other disorder or symptoms thereof associated with impaired pancreatic islet function, in which the subject has been administered a therapeutic amount of Procr$^+$ and/or MSLN$^+$ organoids disclosed herein sufficient to treat the disease or symptoms thereof. The level of insulin (or other marker) determined in the method can be compared to known levels of insulin in either healthy normal controls or in other afflicted patients to establish the subject's disease status. In another embodiment, a second level of insulin in the subject is determined at a time point later than the determination of the first level, and the two levels are compared to monitor the course of disease or the efficacy of the therapy. In certain preferred embodiments, a pretreatment level of insulin (or other marker) in the subject is determined prior to beginning treatment according to this invention; this pre-treatment level of insulin (or other marker) can then be compared to the level of insulin (or other marker) in the subject after the treatment commences, to determine the efficacy of the treatment.

Screening Assays

Some aspects of the present disclosure provide screening assays in which Procr$^+$ and/or MSLN$^+$ endocrine progenitor cells or organoids of the present disclosure are used in an in vitro setting to test the efficacy of insulin production agonists or antagonists, or other compounds, compositions, or agents for inducing or otherwise affecting the differentiation of pancreatic endocrine progenitor cells. The organoids, in some embodiments, are derived from Procr$^+$ and/or MSLN$^+$ endocrine progenitor cells obtained for a healthy subject. In other embodiments, the organoids are derived from a subject having diabetes or another disease or condition characterized by impaired pancreatic islet function. If the insulin production agonist or other compound or composition is effective in promoting increased insulin, then insulin will accumulate in the culture medium and can be quantified. In some instances, the compound or composition administered to the organoid may be detrimental to the health of the organoid. For example, the organoid may cease growing and/or reproducing, may display an altered morphology, or may die. Such results would suggest that the compound or composition has a toxic profile.

In some embodiments, an in vitro screen comprising an organoid of the present disclosure can be used to better understand β-cell or islet function or other endocrine cell function. In some embodiments, organoids generated from Procr$^+$ and/or MSLN$^+$ endocrine progenitor cells derived from a subject having a disease or disorder (e.g., diabetes) can be studied to better understand the molecular and cellular contributors to the subject's disease or condition, including gene mutation and microenvironment factors.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1A:
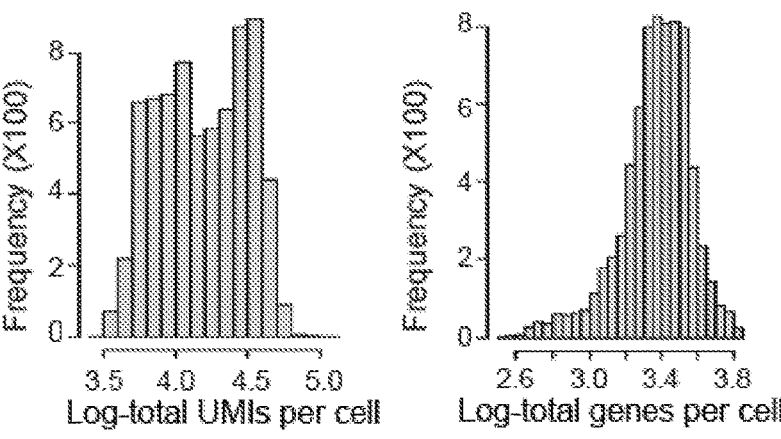
FIGS. 1A-1M illustrate single cell RNAseq analysis reveals a novel pancreatic cell population with EMT properties.
Figure 1B:
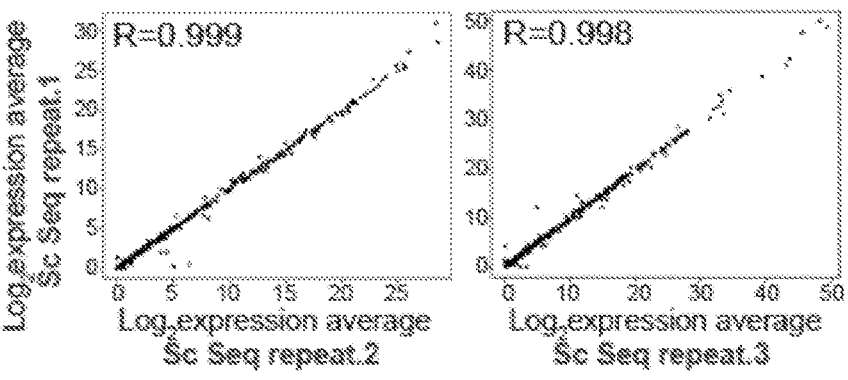
Figure 1C:
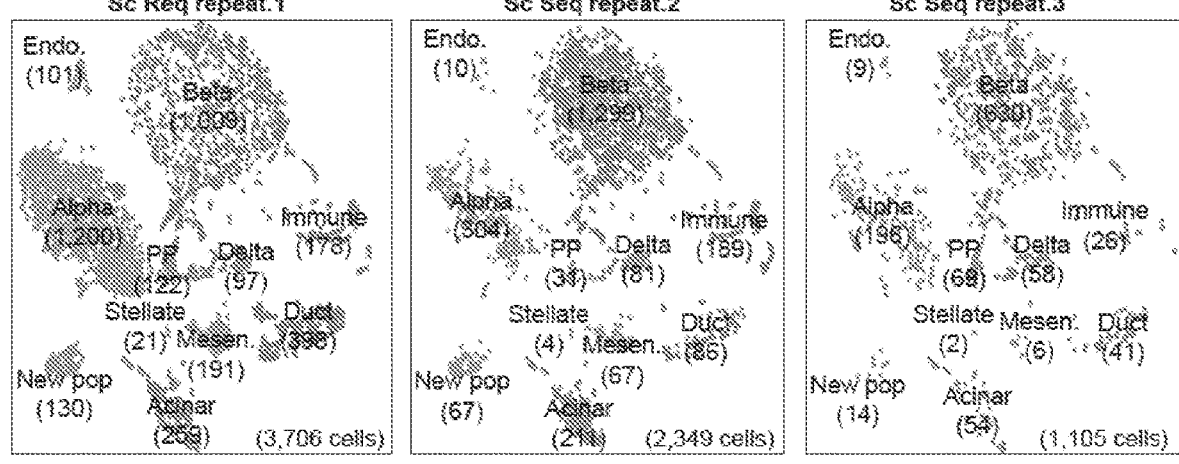
Figure 1D:
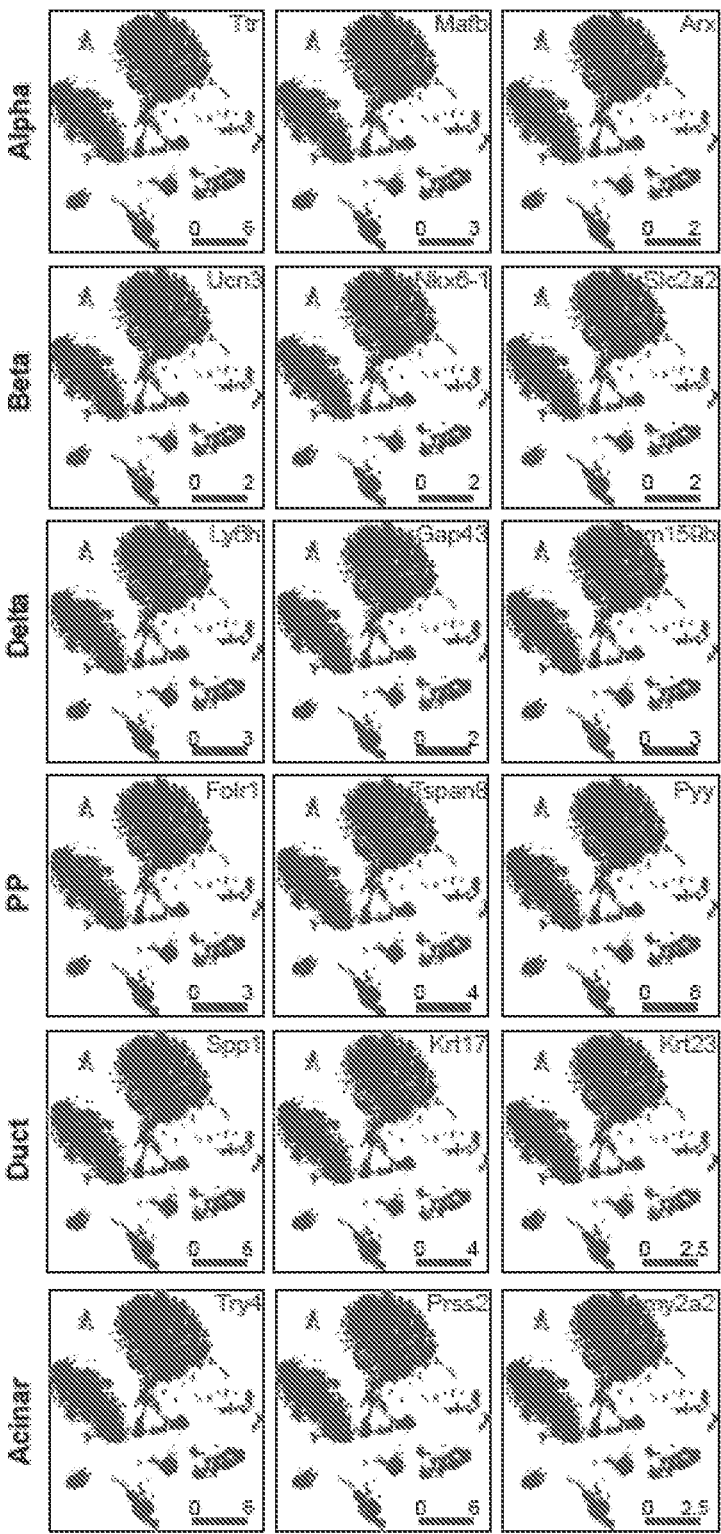
Figure 1E:
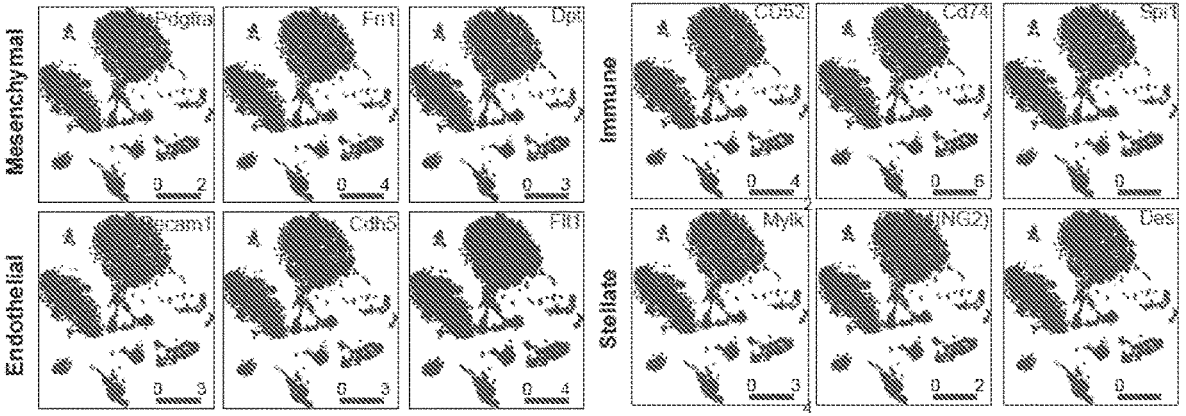
Figure 1F:
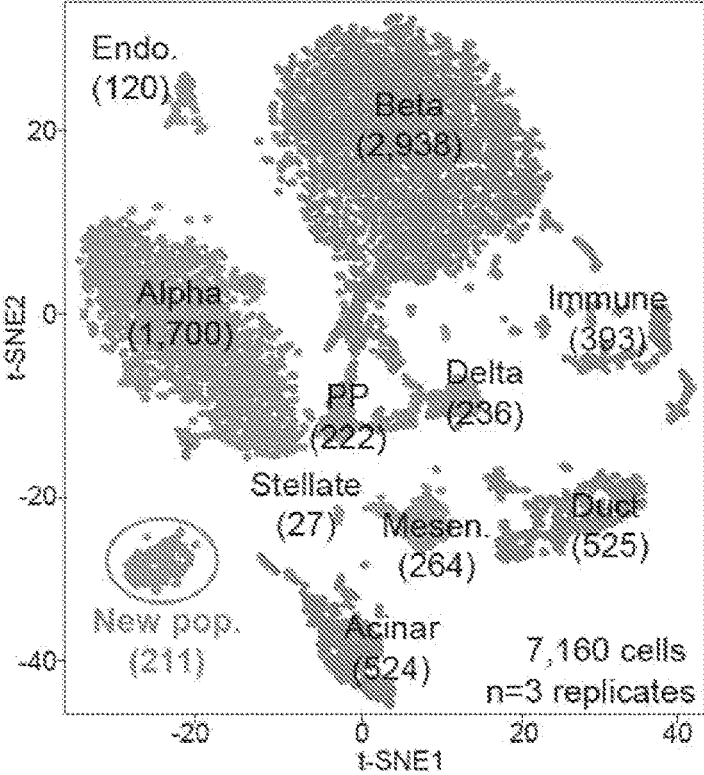
Figure 1G:
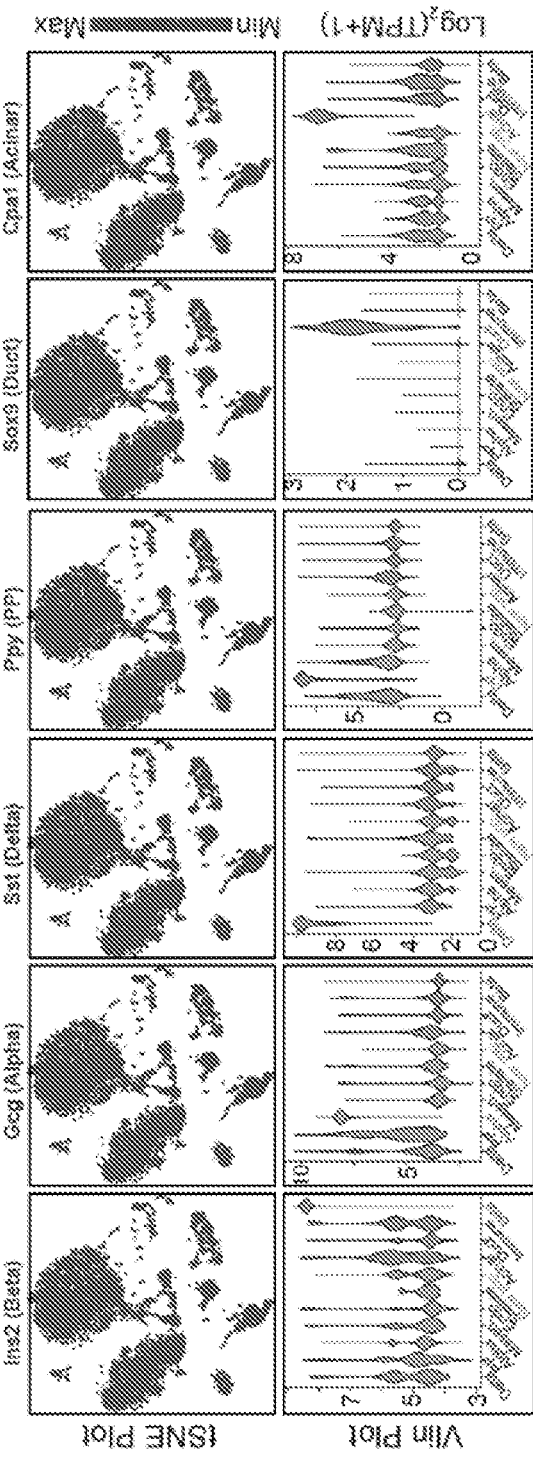
Figure 1H:
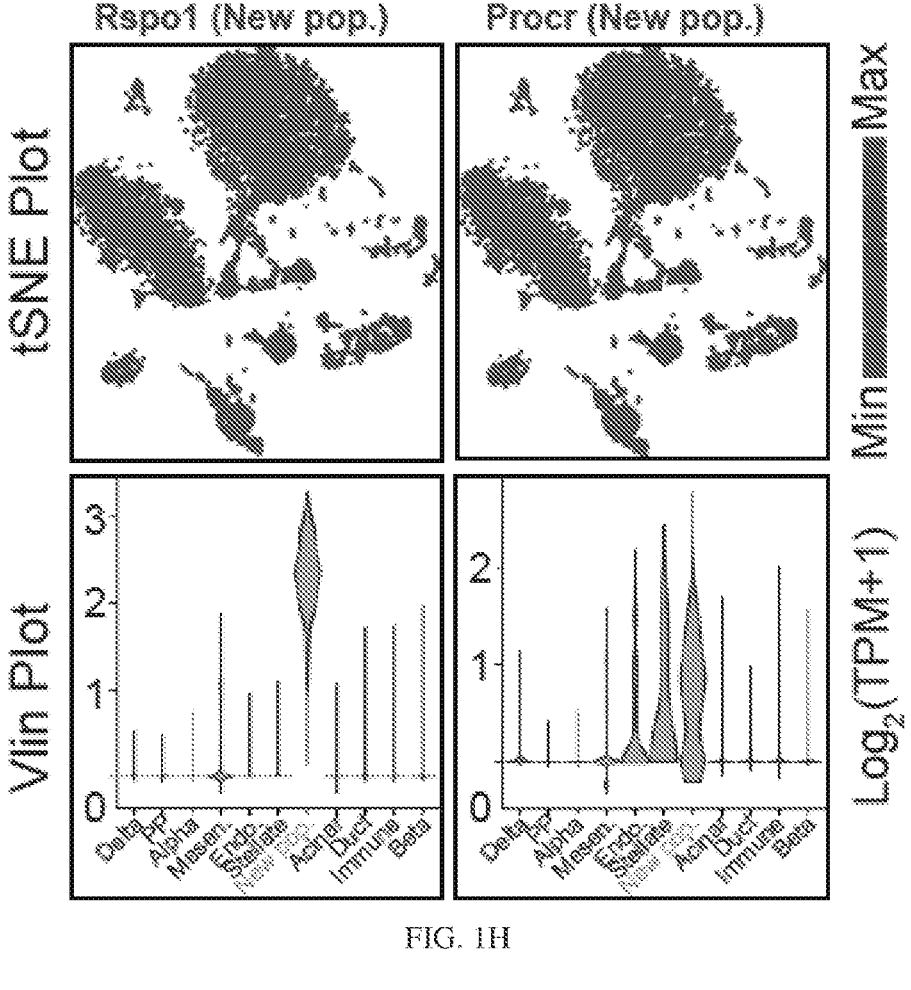
Figure 1I:
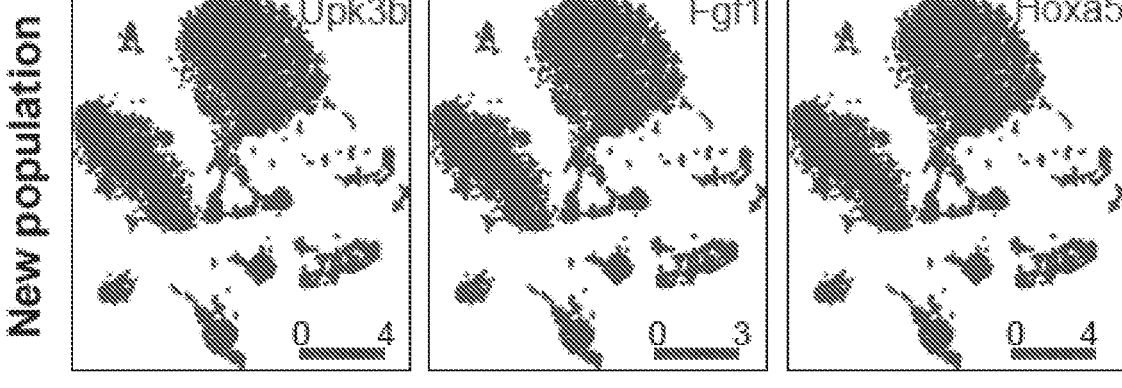
Figure 1J:
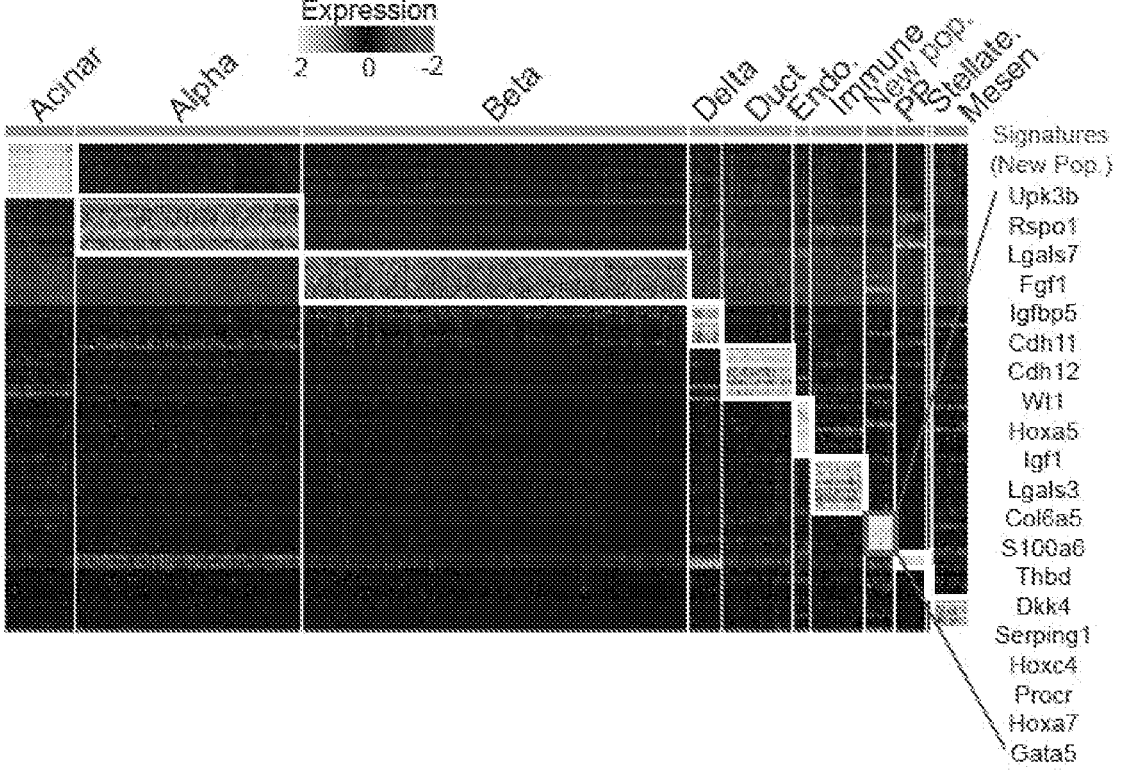
Figure 1K:
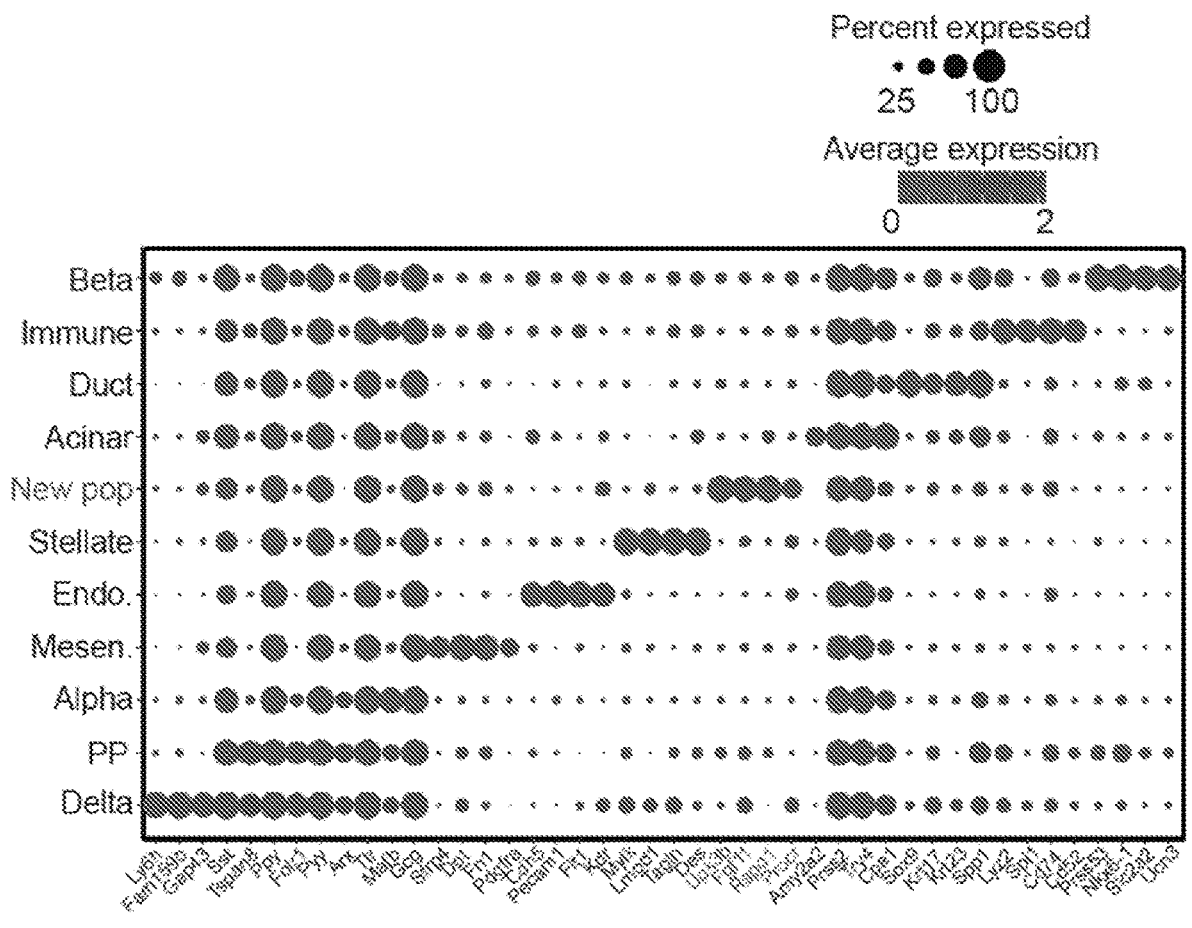
Figure 1L:
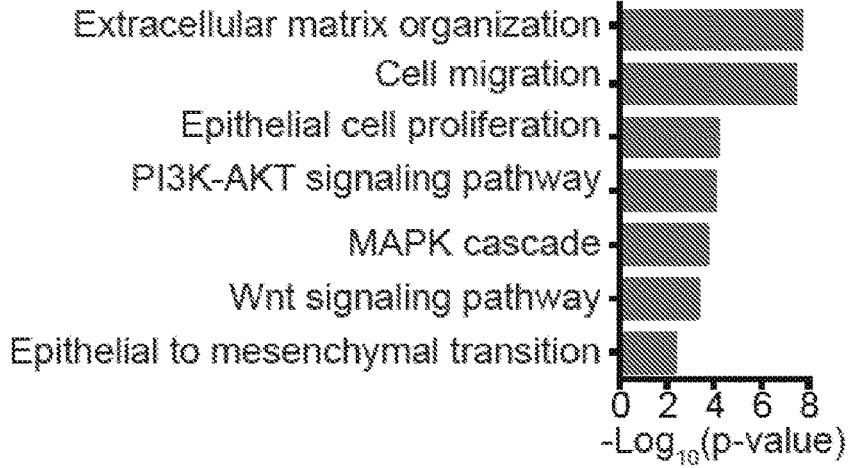
Figure 1M:
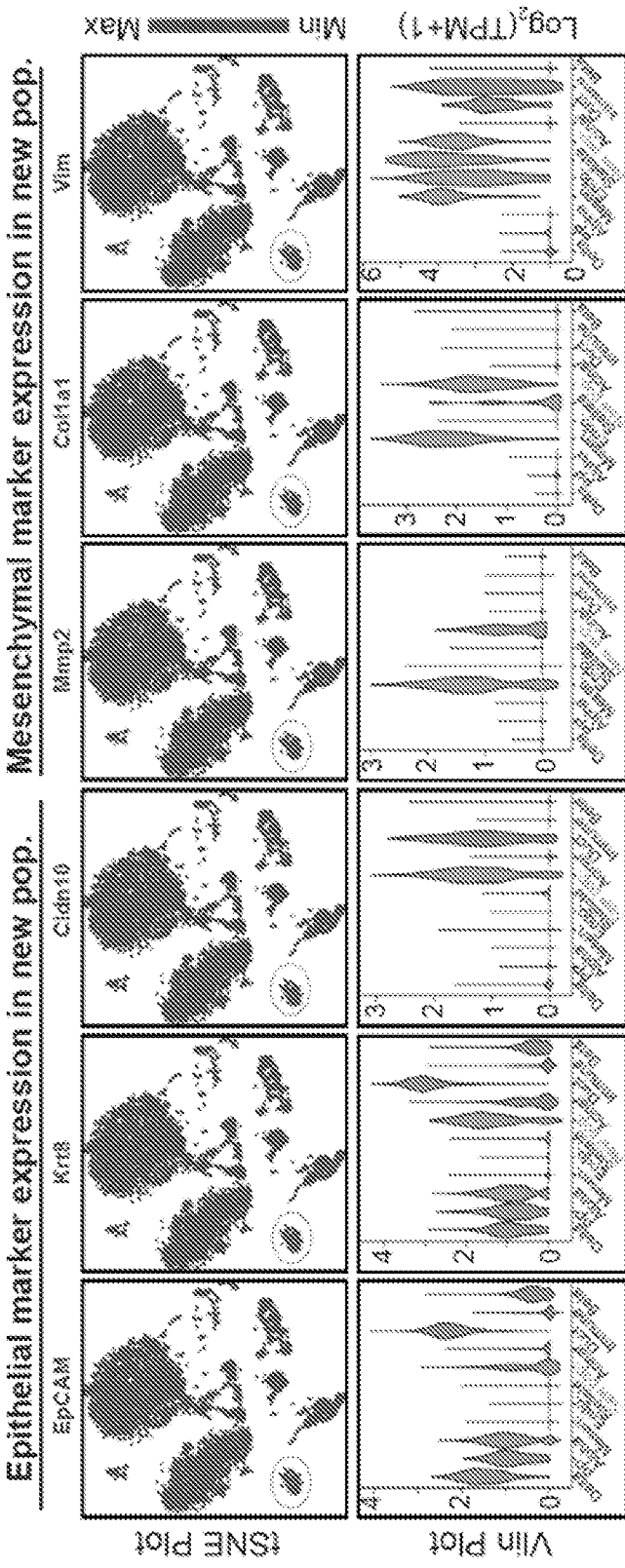

Example 1: Long-Term Expansion of Pancreatic Islet Organoids from Resident Procr+ Progenitors A Procr$^+$ Progenitor Population in Adult Islets As Procr is a surface protein which has been reported to mark stem cells in several adult tissues, including the mammary gland (Wang et al., 2015), endothelium (Yu et al., 2016) and hematopoietic systems (Balazs et al., 2006; Fares et al., 2017; Iwasaki et al., 2010; Zhou et al., 2016), we searched for Procr-positive cells in murine islets using Single Cell (sc) RNAseq. Pancreases from 8-week old adult mice were dissociated and endocrine cells were enriched (see Methods section below). 7,160 cells were profiled using sc RNAseq approaches (FIGS. 1A-1D). Each cluster was mapped to known abundant endocrine (α-, β-, δ- and PP-cells), abundant exocrine (acinar and duct cells), or rare (mesenchymal, endothelial, immune cells, and stellate) cell types (FIGS. 1D-1G). A single cluster contained cells distinct from any known cell population (FIGS. 1F-1H). This novel population displayed unique signature genes, including Rspo1, Fgf1, Upk3b, Hoxa5, and Procr (FIGS. 1H-1K), but did not express known endocrine or exocrine differentiation markers as shown by t-distributed stochastic neighborhood embedding (t-SNE) analysis (FIG. 1D, 1E, 1G, 1K). Gene ontology (GO) analysis identified enrichment of cell migration-, epithelial-to-mesenchymal transition (EMT)- and Wnt signaling pathway-GO terms (FIG. 1L). The signature expression of Wnt agonist gene Rspo1 and Wnt target gene Procr indicated enhanced Wnt signaling pathway activity. The co-expression of epithelial markers (EpCAM, Krt8, and Cldn10) and mesenchymal markers (Mmp2, Col1a1 and Vim) in the new population shown by t-SNE analysis supported its EMT characteristics (FIG. 1M).

Figure 2A:
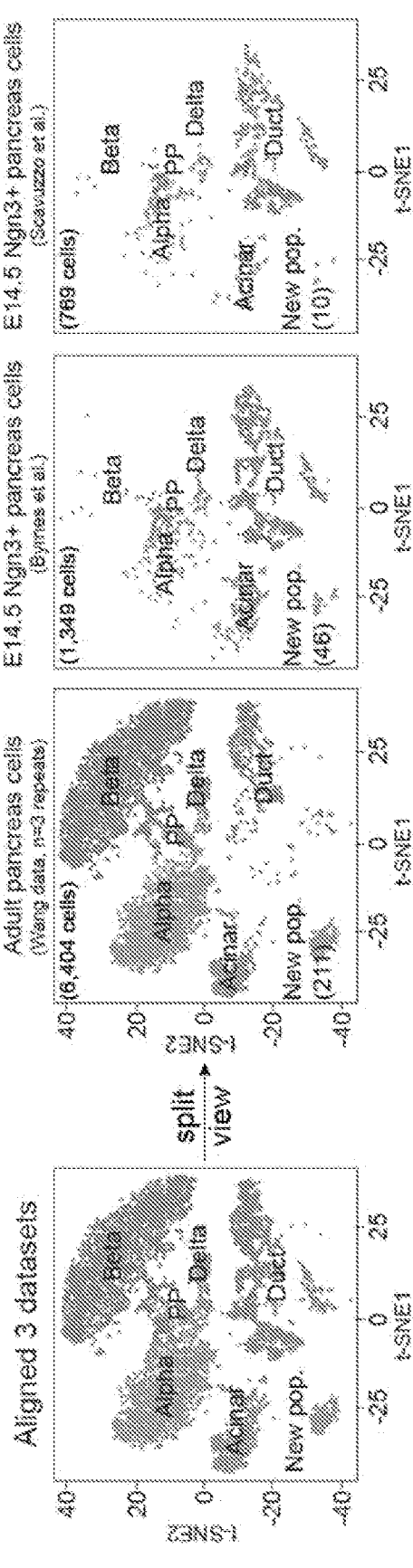
Figure 2B:
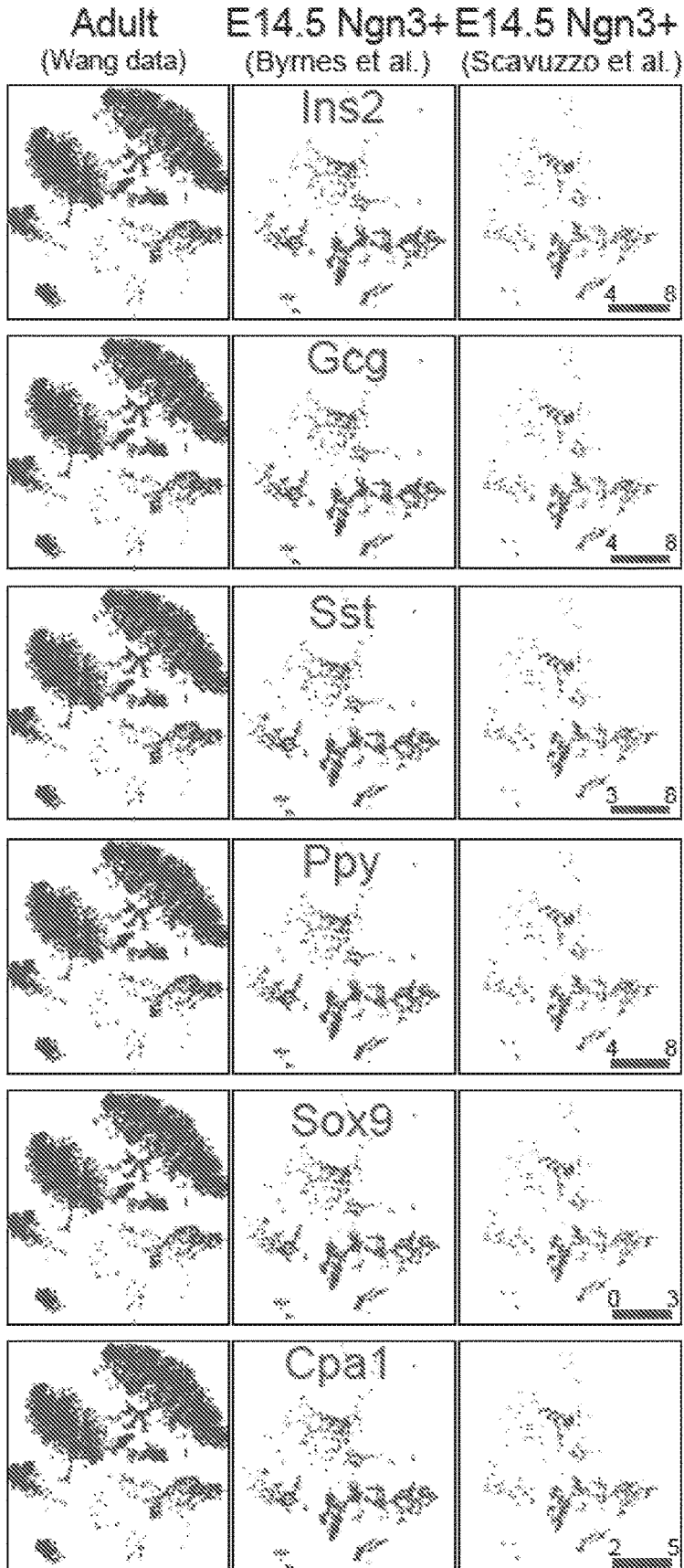
Figure 2C:
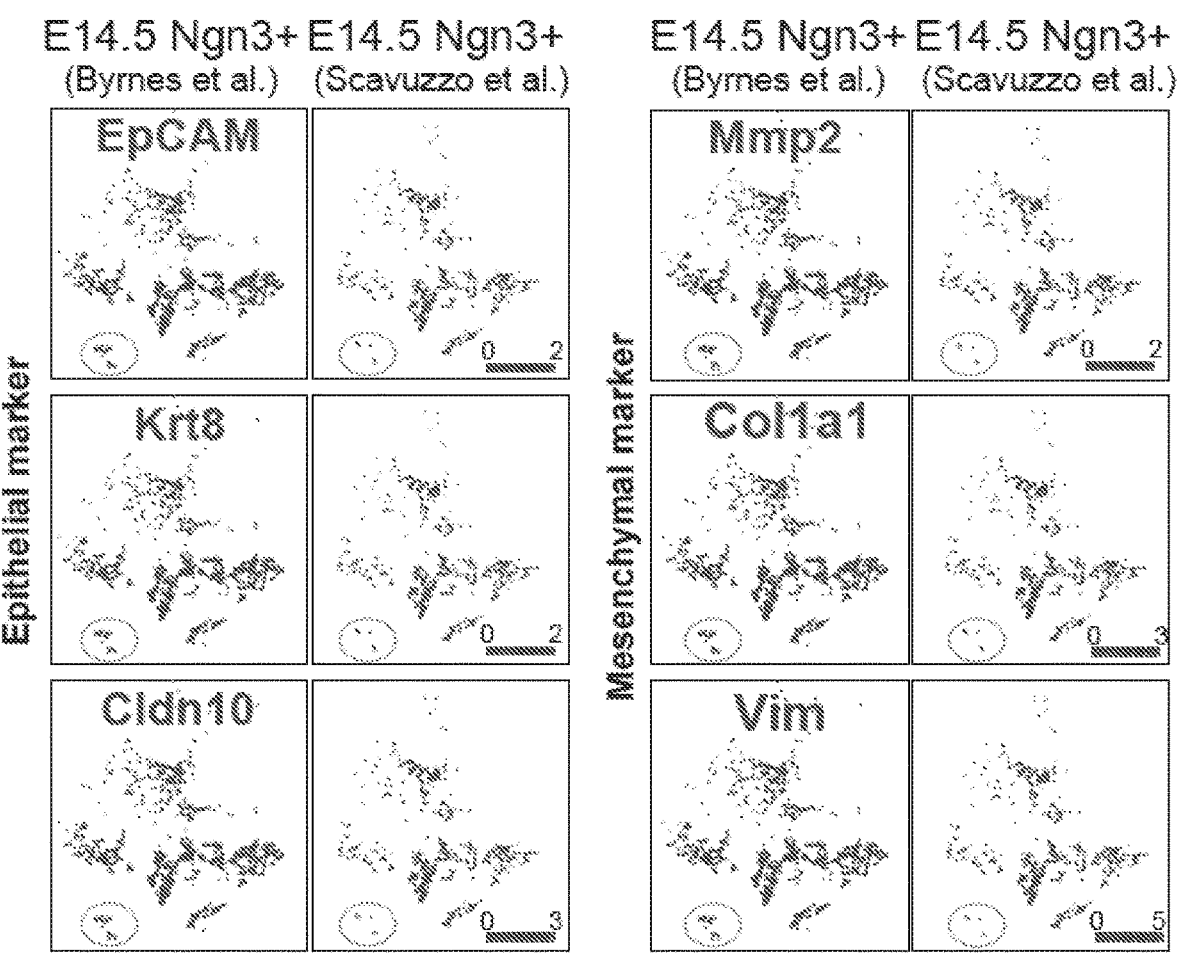
Figure 2D:
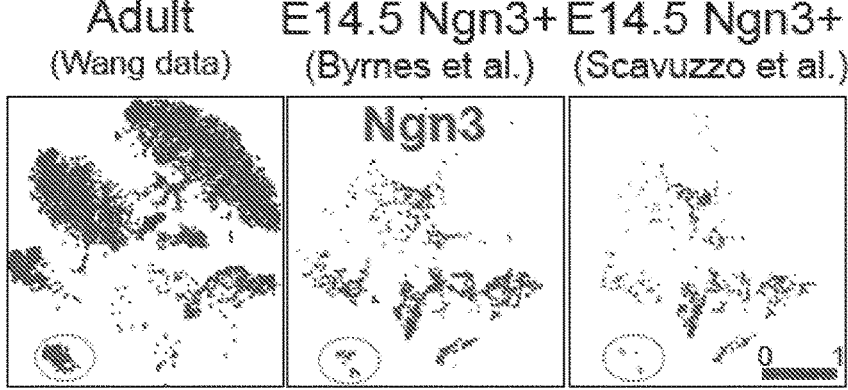
Figure 2E:
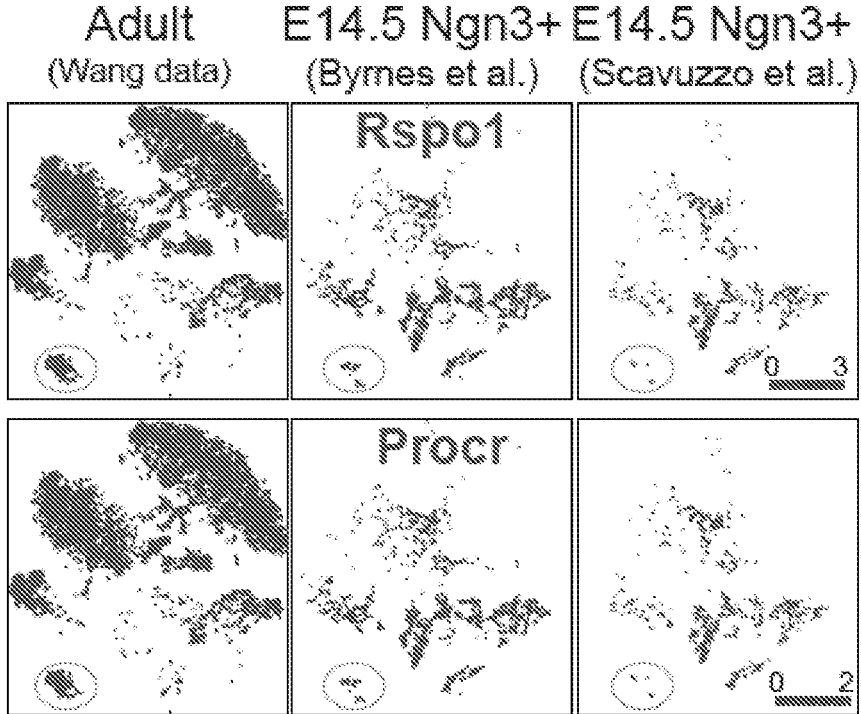
Figure 2F:
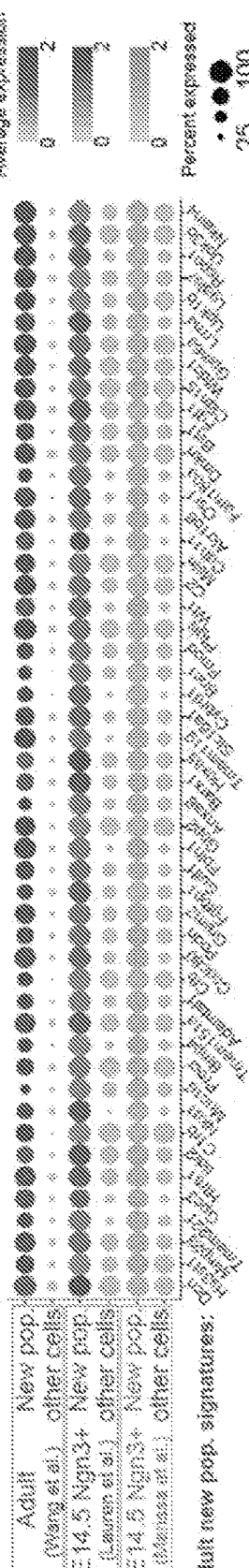
Figure 2G:
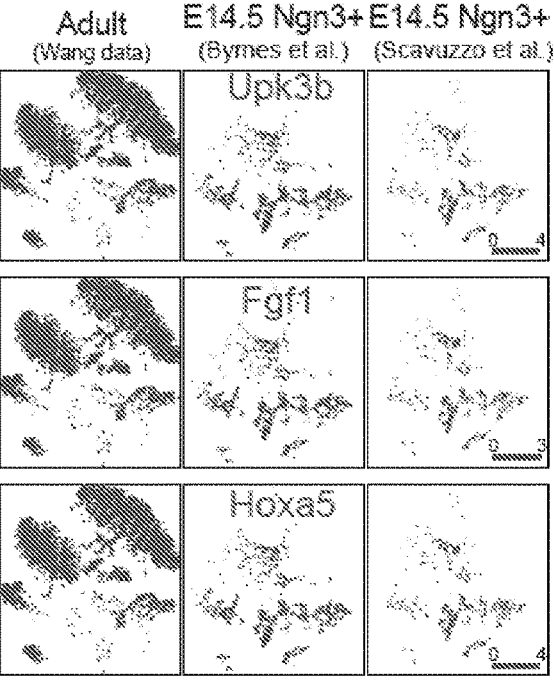
Figure 2H:
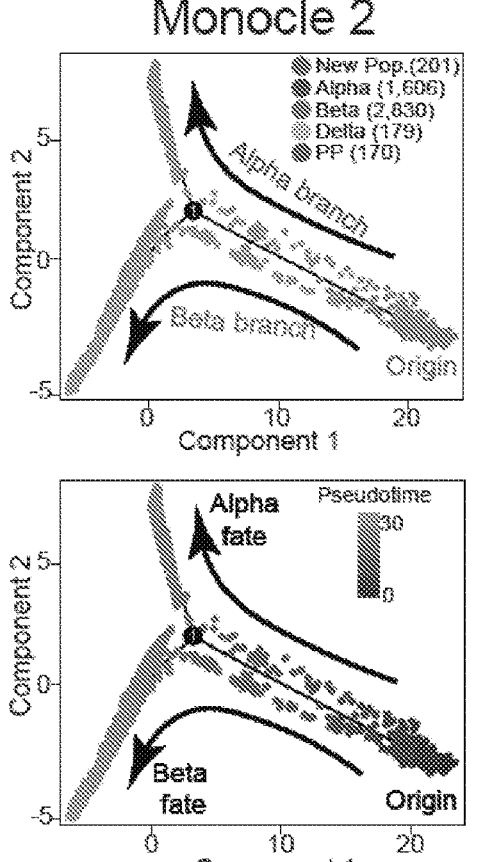
Figure 21:
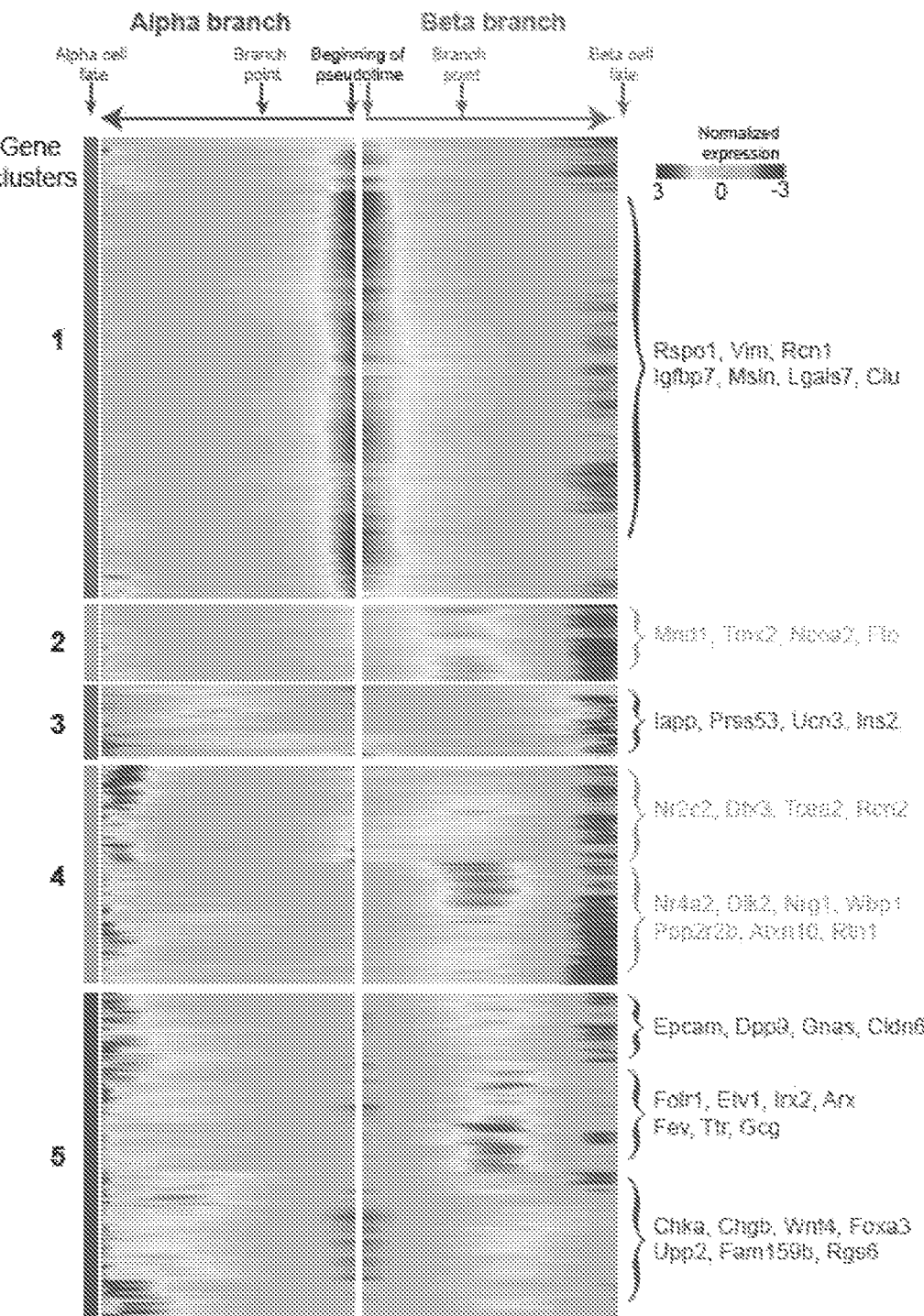

EMT is implicated in the formation of the endocrine islets by committed endocrine precursor cells (Rukstalis and Habener, 2007). The lack of differentiation marker expression in the new population also suggested a potential precursor state. To gain insight into the nature of the new population, expression data was merged with previously reported datasets of embryonic endocrine progenitors (Byrnes et al., 2018; Scavuzzo et al., 2018). The new population seen in adult pancreas aligned with a cluster of Neurog3 (Ngn3)$^+$ cells at embryonic day 14.5 (E14.5) (FIGS. 2A-2B). Interestingly, this population at E14.5 also displays EMT features, i.e., the combined expression of epithelial and mesenchymal markers (FIG. 2C). This E14.5 population was Ngn3$^+$, whereas the adult counterpart was Ngn3$^-$ (FIG. 2D). Importantly, the E14.5 population shared a gene signature, including Rspo1, Fgf1, Dcn, Upk3b, Hoxa5, and Procr (FIG. 2E-2G). The resemblance of the E14.5 population to the embryonic endocrine precursor suggested that the Procr$^+$ population represented a progenitor state. Thus, precursor-progeny relationships between the identified endocrine populations were examined by pseudo temporal analysis using monocle 2 (Qiu et al., 2017). This predicted two developmental trajectories: one toward the β-cell and one toward the α-cell (FIGS. 2H-2I).

Sorting Procr$^+$ Cells from Islets

Figure 3A:
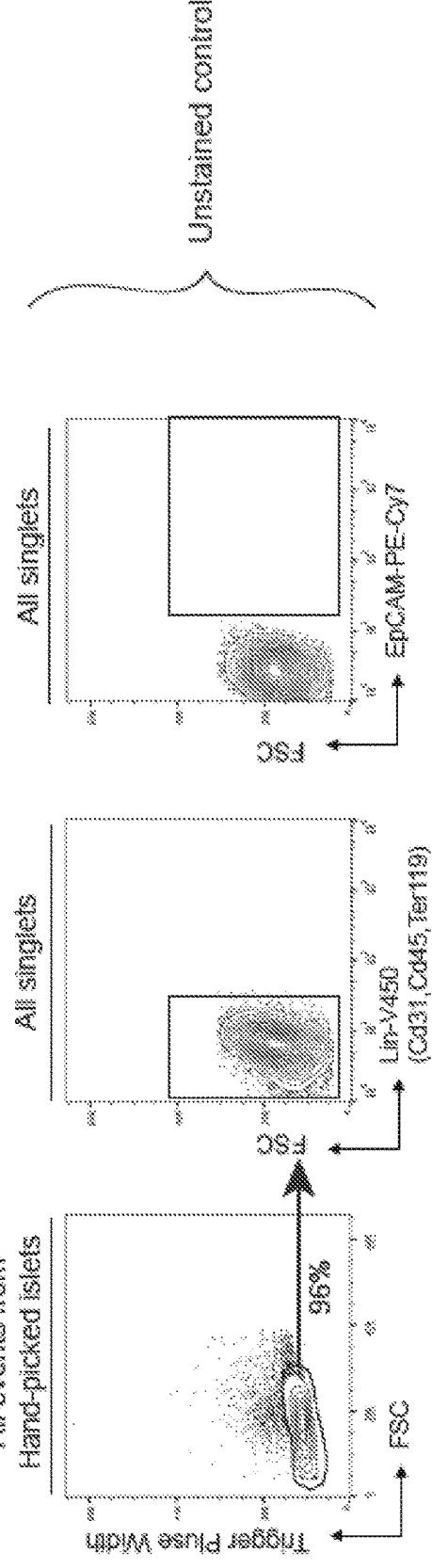
Figure 3B:
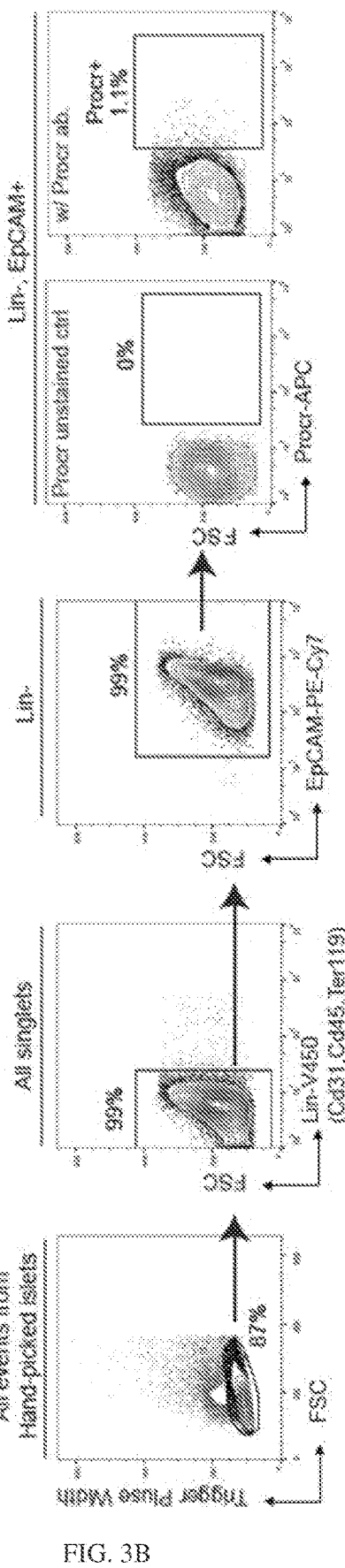
Figure 3C:
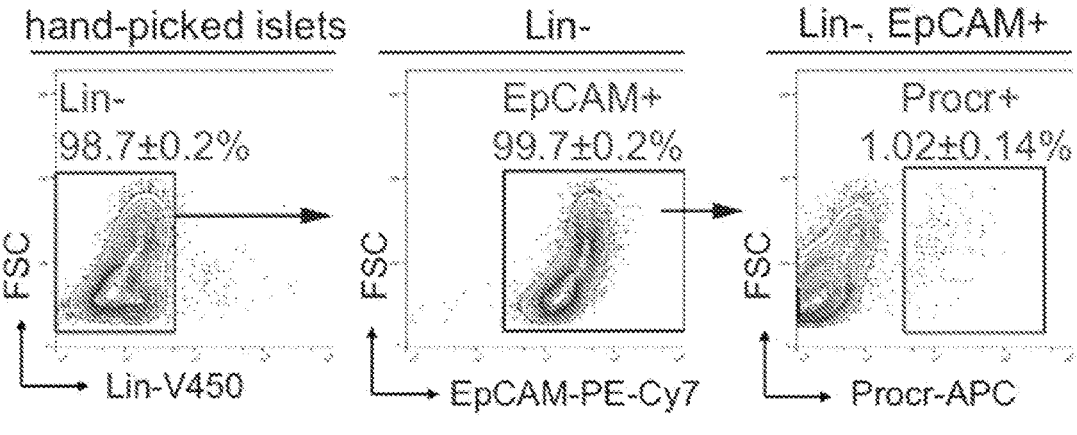
Figure 3D:
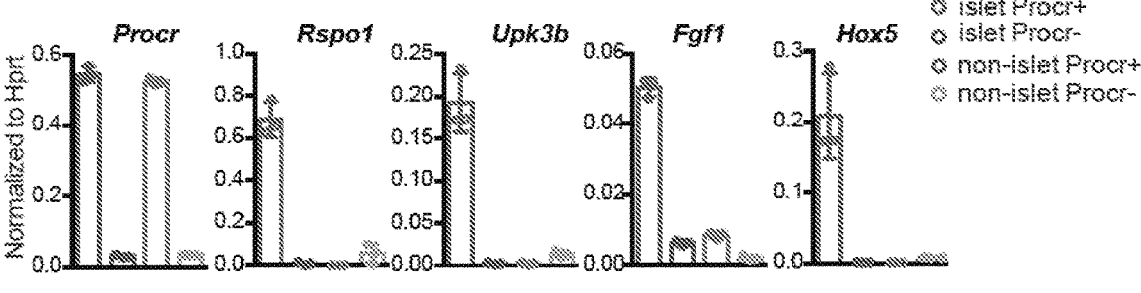

Islets and non-islet tissues were separated by hand-pick. Islet cell preparations underwent negative selection of blood lineage, positive selection of epithelial cells, followed by further separation into Procr$^+$ (Lin$^-$, EpCAM$^+$, Procr$^+$) and Procr$^-$ (Lin–, EpCAM$^+$, Procr) populations (FIGS. 3A-3B). The anti-Procr antibody used was PE or APC anti mouse Procr (clone 1560) from eBioscience. A small population (1.0±0.14%) of islet cells were Procr+(FIG. 3B-3C). Considering that rare mesenchymal, stellate, and endothelial cells can express Procr as shown by sc RNAseq (FIG. 1H), Procr$^+$ and Procr$^-$ cells were isolated from the non-islet tissue also. qPCR analysis indicated that signature genes of the new population, e.g., Rspo1, Fgf1, Upk3b, and Hoxa5 are exclusively expressed in Procr$^+$ islet cells (FIG. 3D).

Figure 3E:
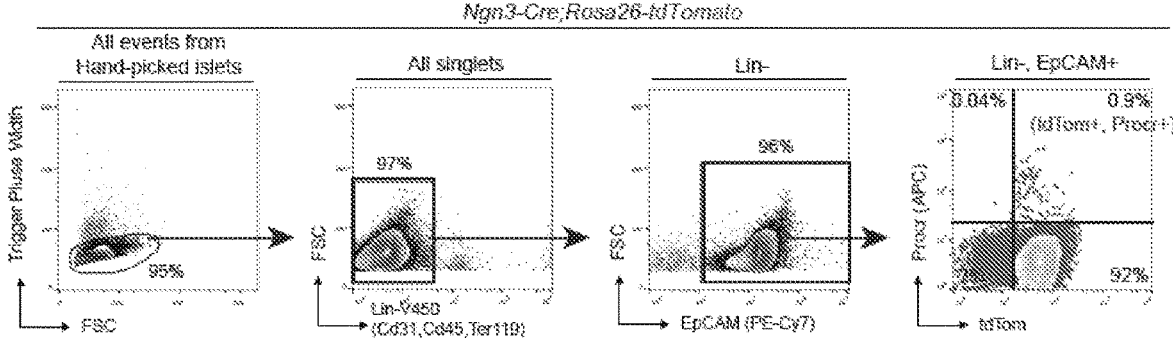

Ngn3-Cre; R26-tdTomato mice were next analyzed in which all endocrine lineages were marked in tdTomato, as they all are derived from embryonic Ngn3$^+$ pancreatic endocrine precursors (Gu et al., 2002). FACS analysis confirmed that Procr$^+$ islet cells were all tdTomato$^+$ (FIG. 3E), identifying the cells as progeny of Ngn3$^+$ endocrine precursors. Notably, they appeared to represent a new type of progeny lacking α-, β-, δ-, and PP-cell differentiation marker expression.

Figure 3J:
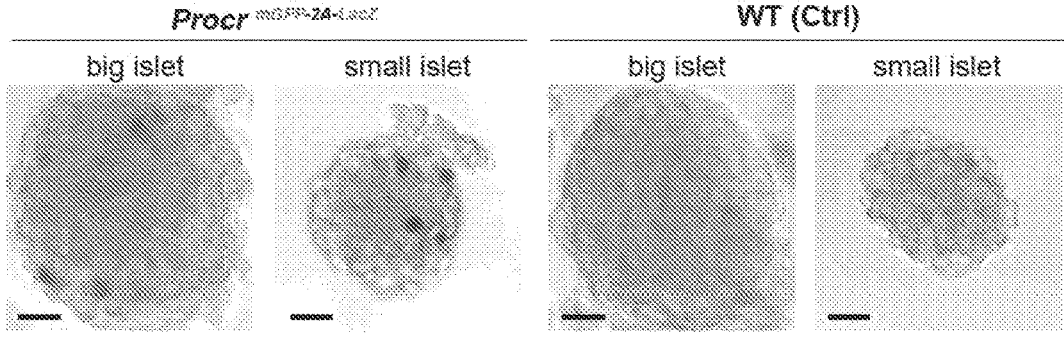
Figure 3K:
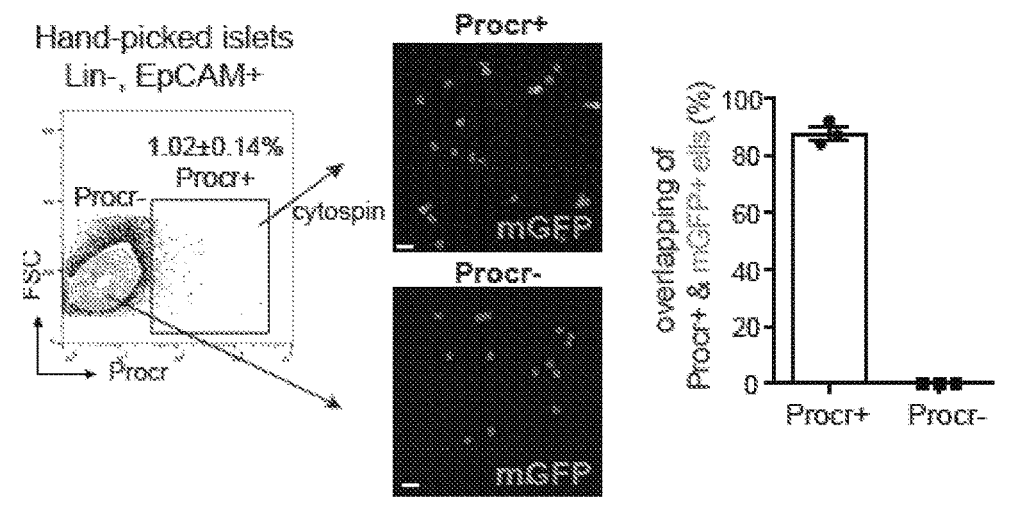
Figure 3L:
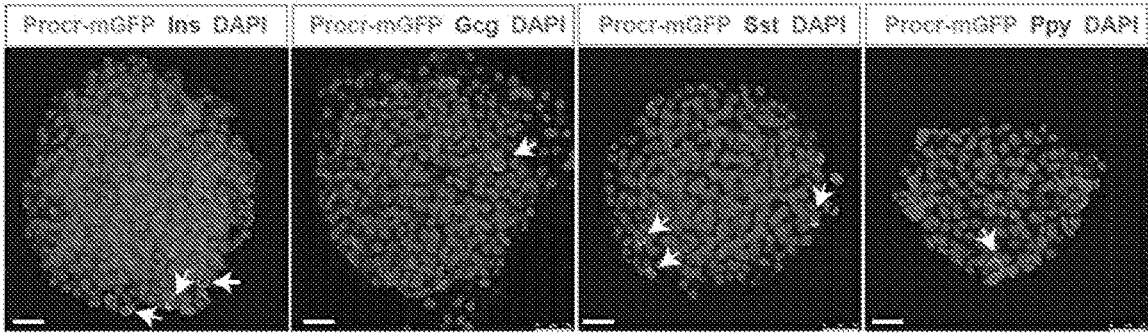
Figure 3M:
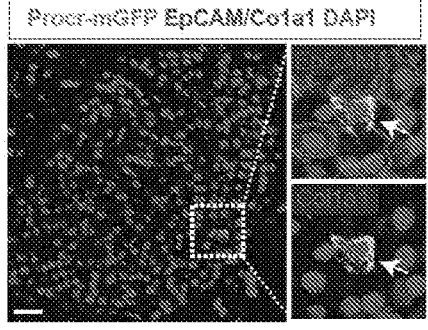
FIG. 3M includes representative confocal image of pancreas section immunostaining that show that the mGFP$^+$ cell (Procr$^+$ cell, arrow) expresses both epithelial marker EpCAM and mesenchymal marker Col1a1. Scale bar denotes 20 Sections are stained and analyzed from n=3 mice.

To visualize this population, a double-reporter allele with a membrane GFP (mGFP)-2A-LacZ cassette inserted at the ATG of Procr (FIGS. 3F-3I) was generated. As shown by whole-mount X-gal staining, Procr expression occurred in a small number of cells in a dispersed pattern in the islets (FIG. 3J). mGFP$^+$ cells were further validated by Procr antibody using FACS (FIG. 3K). Whole-mount islet staining confirmed that mGFP$^+$ (Procr$^+$) cells do not express endocrine differentiation markers (FIG. 3L), yet co-express the epithelial marker EpCAM and the mesenchymal marker Col1a1 (FIG. 3M), which was consistent with sc RNAseq analysis.

Single Procr$^+$ Islet Cells Form Islet-Like Organoids in Culture

Figure 4A:
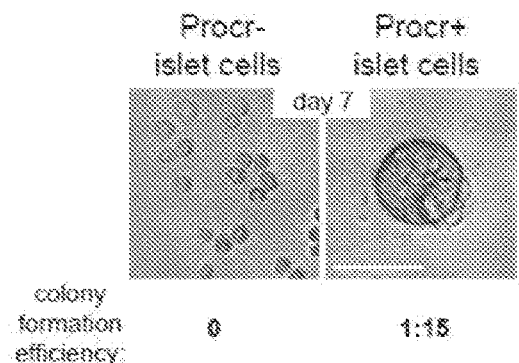
FIGS. 4A and 4B characterize pancreatic organoids at 7 days and 28 days of culture.
Figure 4B:
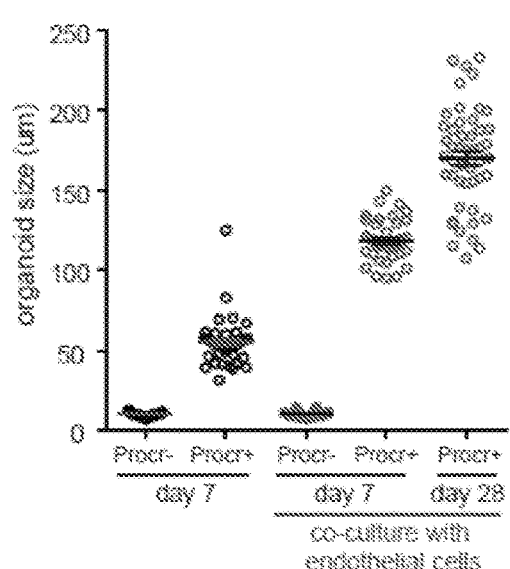

It was hypothesized that Procr$^+$ islet cells can serve as a cellular source for new β-cells in vitro. Procr$^+$ islet cells were FACS-isolated and plated at clonal density in 3D culture with serum-free media, supplemented with growth factors, including B27, ITS, EGF, heparin, and FGF2. While unsorted islet cells had a very low colony-forming efficiency (i.e., 1 colony formed out of 2,000 plated total cells), Procr$^+$ islet cells exhibited a 130-fold increased clonogenicity (i.e., 1 out of 15 plated cells formed a colony) (FIG. 4A). In contrast, Procr$^-$ islet cells were not able to form colonies (FIG. 4B). However, colonies derived from either unsorted islet cells or Procr$^+$ islet cells could not sustain for more than 7 days.

Figure 5A:
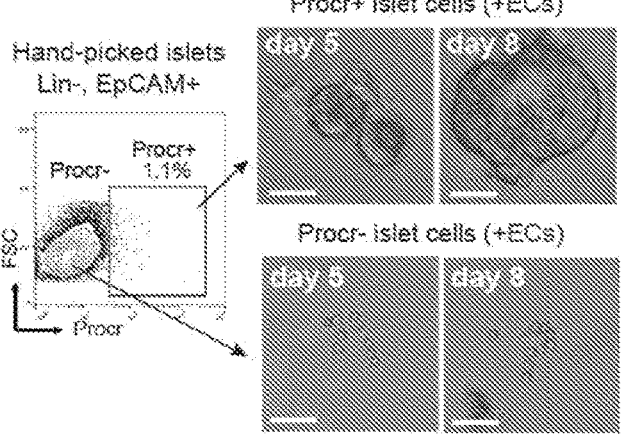
FIGS. 5A-5N demonstrate that islet organoids derived from single Procr$^+$ islet progenitor cells can express insulin.
Figure 5B:
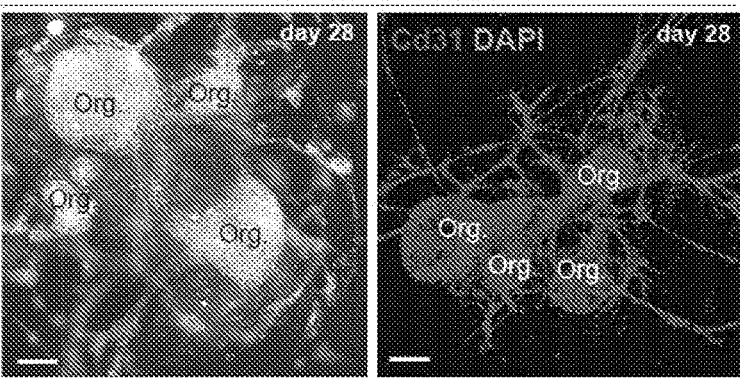
FIG. 5C is a scatter plot showing the size per islet organoid cultured for 7 or 28 days. n=3 biological replicates, one of three similar results are shown. The average organoid sizes are presented as mean±s.e.m.
FIG. 5D includes representative confocal images of whole mount insulin immunostaining in fresh islets or organoids cultured for 7 or 28 days, with or without glucose challenge. Scale bar denotes 20 μm. "hi glucose" denotes high glucose.
FIG. 5E is a scatterplot showing the percentage of insulin$^+$ (highly-expressed) cells per organoid under each indicated condition. n=3 biological replicates, one of three similar results is shown. The average percentages are presented as mean±s.e.m. "d7" denotes day 7; "hi glu" denotes high glucose.
FIG. 5F includes graphs showing expression levels of beta cells marker genes under each indicated condition are detected by qPCR. n=3 biological replicates. Data are presented as (mean+min)/max.
FIG. 5G includes graphs showing representative population measurements of dynamic normalized Fluo-4 fluorescence intensity for primary day 28 islet organoids challenged sequentially with 2, 20, 2, 20, 2, and 20 mM glucose and 30 mM KCl. The x axis represents time. n=3 biological replicates are shown separately.
FIG. 5H includes electron microscopy images and quantification (e) of granules within sectioned cells for each indicated culture condition. A fresh islet β-cells sample is shown. Increasing numbers of crystallized insulin granules are found in day 28 organoids after glucose challenge, indicating maturation of the β-cells. n=3 biological replicates. One of three similar quantification results is shown. Scale bar denotes 1 μm. "d7" denotes day 7; "d28" denotes day 28; "hi glu." denotes high glucose; "org." denotes organoid.
FIG. 5I is a scatterplot quantifying the results observed in FIG. 5H.
FIG. 5J is a graph of ELISA measurements of secreted insulin from day 28 islet organoids challenged sequentially with 2, 20, 2, 20, 2, and 20 mM glucose, with a 30-minute incubation for each condition. n=3 biological replicates. Data are presented as mean±s.e.m.
FIG. 5K includes images of whole mount immunostaining of α-cells marker Gcg, δ-cells marker Sst or PP-cells marker Ppy expressed by cells in fresh islets.
FIG. 5L is a graph quantifying the results observed in FIG. 5K.
FIG. 5M includes images of whole mount immunostaining of α-cells marker Gcg, δ-cells marker Sst or PP-cells marker Ppy expressed by cells in day 28 organoids.
Figure 5C:
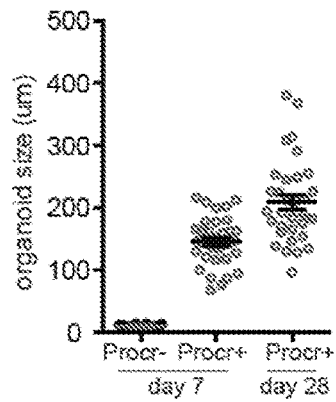

Endothelial cell (ECs), proposed as a critical niche component proposed as a critical niche component, were then added in co-culture (supplemented with VEGFa, see Methods section below). Procr$^+$ islet cells exhibited robust colony formation ability (i.e., 1 colony formed out of 4 plated Procr$^+$ cells) when co-cultured with ECs. Colonies were readily observed from day 5. By day 8, colonies were observed with an average diameter of 145 μm (FIG. 5A). In contrast, Procr$^-$ islet cells remained as single cells (FIG. 5A). Procr$^+$ cell-derived colonies were continuously cultured in the same conditions for a total of 28 days. The formation of more elaborated structures was observed, with large epithelial organoids in the center, surrounded and infiltrated by endothelial networks (FIG. 5B). The average organoid diameter reached 210 μm (FIGS. 5B-5C), similar to the size of mouse islets in vivo.

Figure 5D:
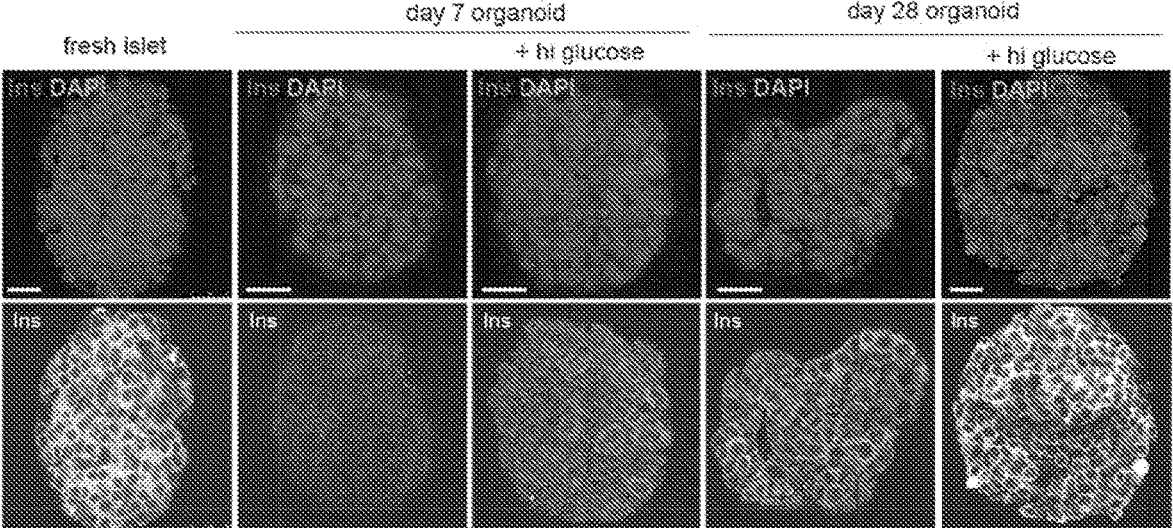
Figure 5E:
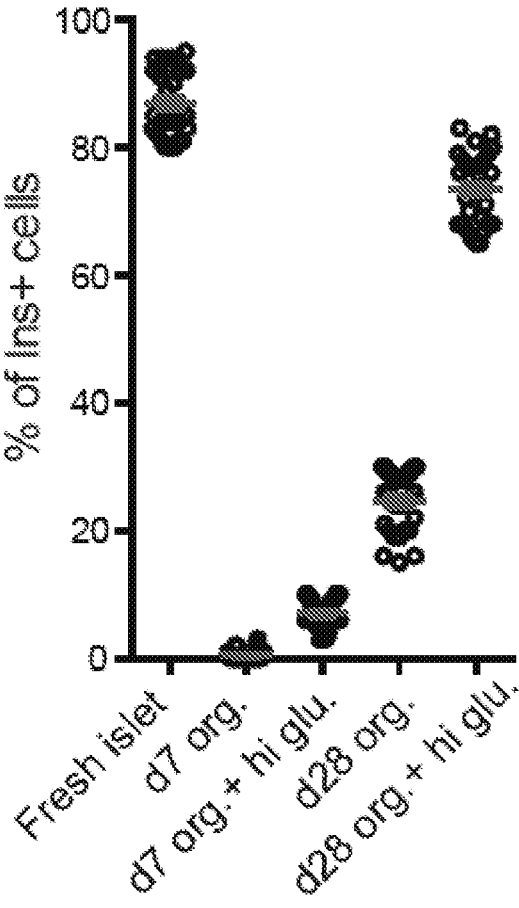
Figure 5F:
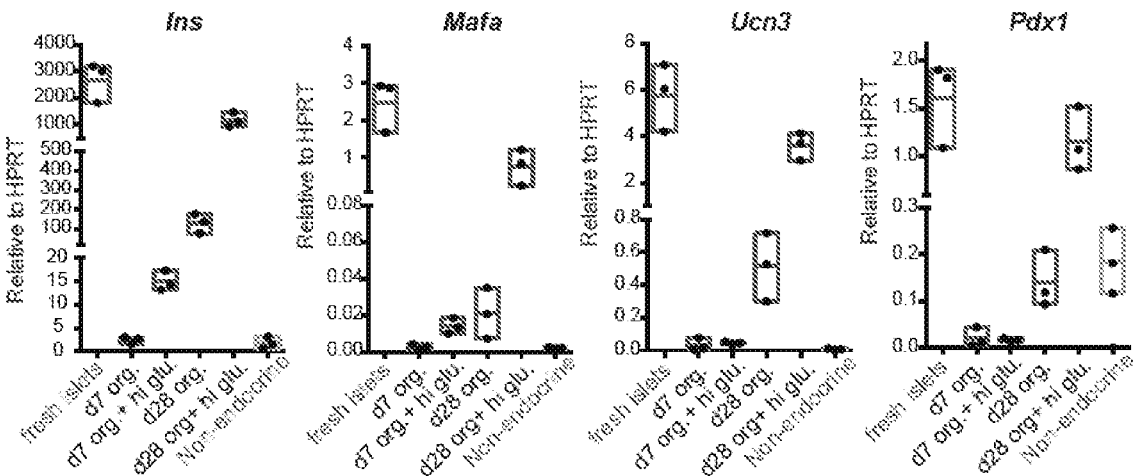

Insulin (Ins) expression was examined as an indication of functional β-cell formation. Ins staining was absent at day 7 and appeared at low levels at day 28 (FIG. 5D). After glucose stimulation (12 hrs incubation with low glucose followed by 12 hrs treatment with high glucose for a total of 3 rounds, see Methods section below), Ins expression in day 28 organoids reached a level comparable to that of freshly isolated islets (FIGS. 5D-5E). However, the same glucose stimulation treatment had only modest effects on Ins expression in day 7 organoids, suggesting that prolonged culture is critical for β-cell formation. β-cell key regulatory factors, MafA, Ucn3, and Pdx1, rose to similar levels in day 28 high-glucose treated organoids as compared to freshly isolated islets, as measured by qPCR analysis (FIG. 5F). The day 28 organoids rapidly increased cytosolic Ca$^{2+}$ concentrations in response to glucose and subsequently returned to baseline (FIG. 5G), indicating their capability of responding acutely to glucose (Mohammed et al., 2009). Analysis of ultrastructure by transmission electron microscopy (TEM) revealed that day 28 organoids contain abundant endocrine granules (FIGS. 5H-5I). ELISAs confirmed secretion of insulin in the media upon glucose stimulation of day 28 organoids (FIG. 5J). In addition to the abundant Ins$^+$β-like cells, the organoids contained smaller numbers of glucagon (Gcg)$^+$ α-like cells, somatostatin (Sst)$^+$ δ-like cells, and pancreatic polypeptide (Ppy)$^+$ PP-like cells reminiscent of the composition of fresh islets (FIGS. 5K-5N). Thus, a culture system was established that harnessed the endocrine progenitor-like capacity of Procr$^+$ cells, which allowed generation of islet-like organoids in vitro. Cells within these organoids were capable of producing packaged insulin granules, of glucose sensing, and of insulin secretion.

Islet-Like Organoids can be Expanded In Vitro Long-Term

Figures 5K, 5L, 5M, 5N, 6A, 6B:
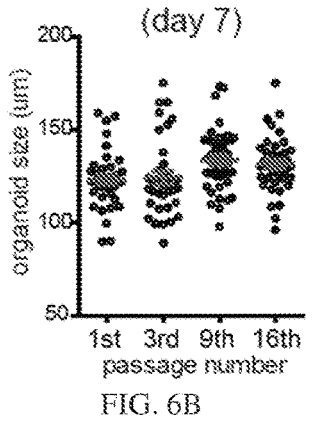
Figure 6C:
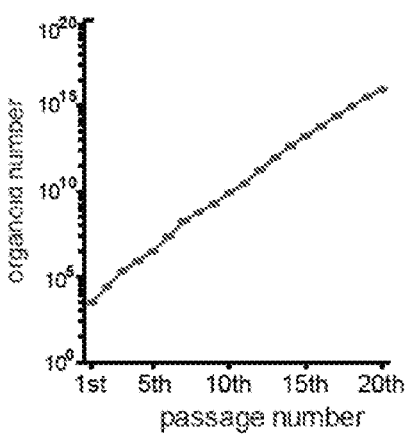
FIG. 6C is an expansion curve of islets organoids (derived from primary mouse islet Procr+ cells) followed from passage 1 to passage 20. n=3 biological replicates. Data are presented as mean±s.e.m.

The organoids described above were expanded through passaging. Dissociated single cells were replated every 7-8 days at a ratio of 1:4-6 (i.e., cells from 1 well were replated to 4-6 wells) in the same culture condition and supplemented with fresh ECs (see Methods section below). In this culture system, the average organoid size remained stable during passaging (FIGS. 6A, 6B). However, the number of organoids grew 3- to 7-fold with each passage (FIG. 6C). Organoids could be passaged at least 20 times, or 6 months, with no deceleration of expansion rate (FIG. 6C).

Figure 6D:
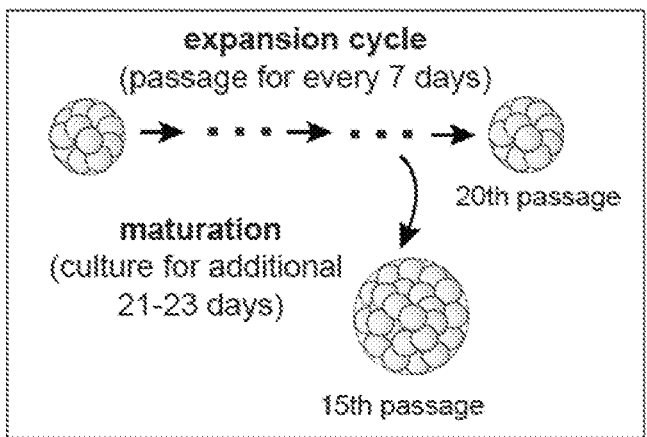
FIG. 6D is an illustration of an organoid expansion/maturation model.
Figure 6E:
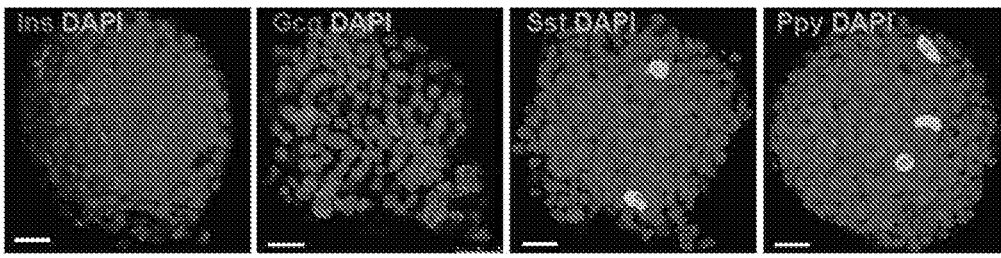
FIG. 6E includes representative images of whole mount immunostaining of β-cells marker Ins, α-cells marker glucagon (Gcg), δ-cells marker somatostatin (Sst), and PP-cells marker pancreatic polypeptide (Ppy) in 15th passaged day 30 organoids after glucose challenge. Scale bar denotes 20
Figure 6F:
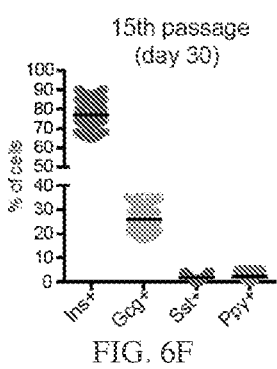
FIG. 6F is a graph quantifying the whole mount immunostaining described in FIG. 6E. n=3 biological replicates. One of three similar quantification results are shown. The average percentages are shown as mean±s.e.m.
Figure 6G:
FIG. 6G includes representative images of whole mount immunostaining of β-cells marker Ins, α-cells marker glucagon (Gcg), δ-cells marker somatostatin (Sst), and PP-cells marker pancreatic polypeptide (Ppy) in 7th passaged day 30 organoids after glucose challenge. Scale bar denotes 20
Figure 6H:
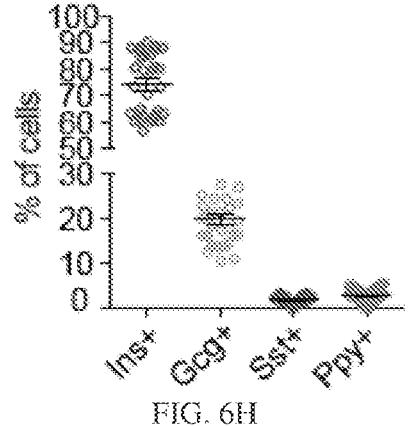
FIG. 6H is a graph quantifying the whole mount immunostaining described in FIG. 6G. n=3 biological replicates. One of three similar quantification results are shown. The average percentages are shown as mean±s.e.m.
Figure 6I:
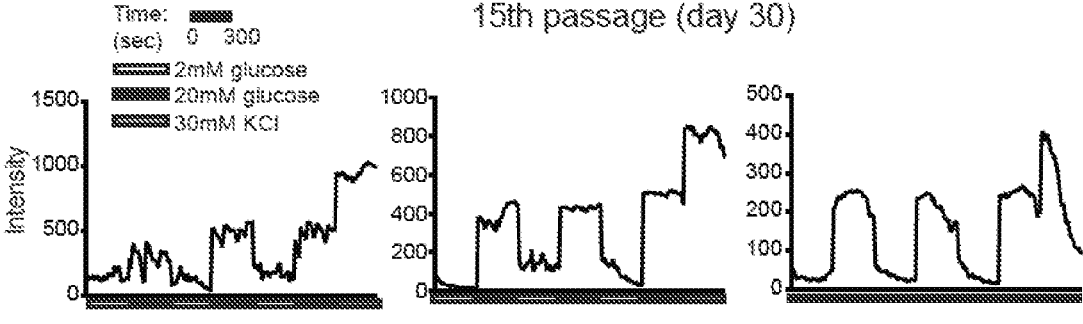
FIG. 6I includes graphs showing representative population measurements of dynamic normalized Fluo-4 fluorescence intensity for 15th passaged day 30 islet organoids challenged sequentially with 2, 20, 2, 20, 2, and 20 mM glucose and 30 mM KCl. The x axis represents time. n=3 biological replicates are shown separately.
Figure 6J:
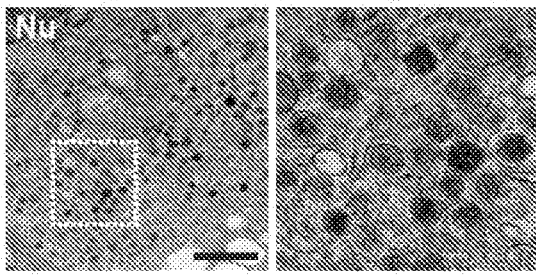
FIG. 6J includes electron microscopy images of granules within sectioned cell. Crystallized insulin granules are found in 15th day 30 organoids after glucose challenge, indicating the maturation of β-cells. n=3 biological replicates. Scale bar denotes 1
Figure 6K:
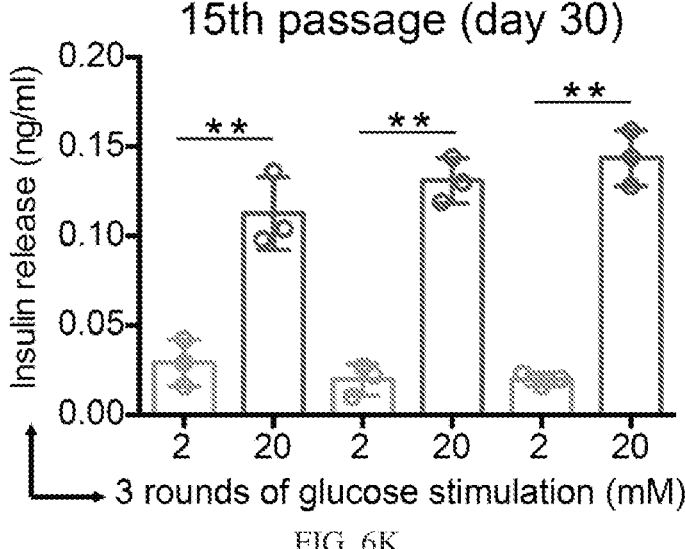
FIG. 6K is a graph depicting ELISA measurements of secreted insulin from 15th passaged day 30 islet organoids challenged sequentially with 2, 20, 2, 20, 2, and 20 mM glucose, with a 30-minute incubation for each concentration. n=3 biological replicates. Data are presented as mean±s.e.m.
Figure 6L:
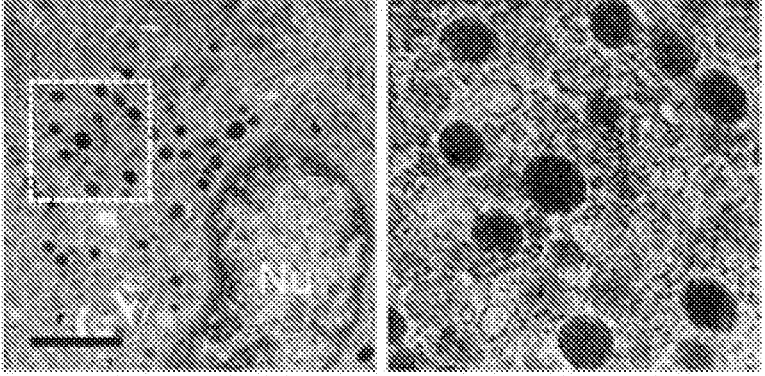
FIG. 6L includes electron microscopy images of granules within sectioned cell. Crystallized insulin granules are found in 7th day 30 organoids after glucose challenge. n=3 biological replicates. Scale bar denotes 1

When passaged organoids were taken out of expansion cycle and allowed to mature for an additional 3 weeks (i.e., 28-30 days upon being replated as single cells; see FIG. 6D), and mature organoids appeared that resembled the primary organoids described above. 7th and 15th passage organoids are given as examples, showing similar percentages of α-, β-, δ-, and PP-cells (FIG. 6E-6H), glucose sensing and insulin secretion abilities, insulin granule numbers, and Ca$^{2+}$ response when compared to the primary passage organoids (FIG. 5G-5H, FIGS. 6I-6N). These results suggest that the expansion and differentiation capacities of the cells were maintained long-term.

Long-Term Cultured Organoids Reverse Diabetes In Vivo

Long-term cultured organoids were transplanted into the kidney capsule of streptozotocin (STZ)-induced diabetic mice to test the full potential of the organoids. The mice were monitored for glycemic improvement. 1000 organoids (from 7th or 15th passage, taken at day 7 of culture) or 300 freshly isolated islets, which contained similar cell numbers (300,000 cells), were transplanted per recipient mouse. At 1-week post-transplantation, blood glucose levels were clearly reduced (FIG. 7A), and body weight loss was stopped (FIG. 7B). The glycemic improvement was maintained throughout the analysis period (FIG. 7A). Notably, the organoid-transplanted groups exhibited similar rescue effects as the fresh islet-transplanted group (FIGS. 7A and 7C). At 1-month post-transplantation, mice transplanted with organoids exhibited glucose clearance ability and serum insulin levels almost identical to the mice receiving fresh islets (FIGS. 7C-7D). Thus, the transplanted organoids were capable of secreting insulin and ameliorating progressive hyperglycemia in a diabetic mouse model.

Figure 7E:
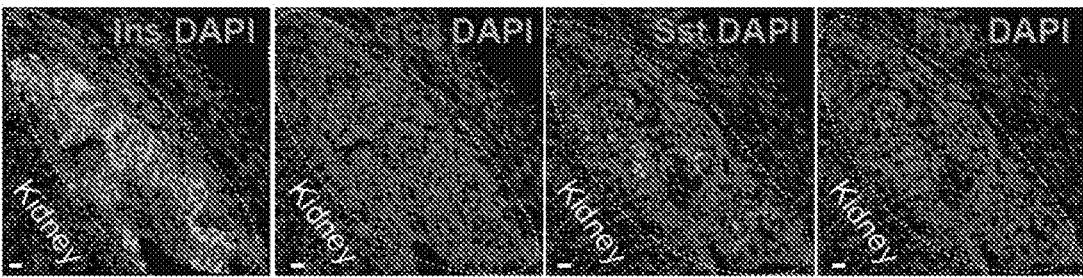
FIG. 7E is representative images of immunofluorescence staining of β-cells marker Ins, α-cells marker Gcg, δ-cells marker Sst or PP-cells marker Ppy on regenerated tissues engrafted organoids for 1 month. n=3 mice. Scale bar denotes 20 "Org." denotes organoid.
Figure 7F:
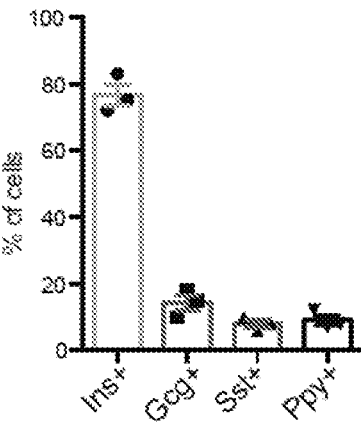
FIG. 7F is a graph quantifying the different hormone-expressing cells in regenerated tissues engrafted organoids for 1 month. n=3 mice.
Figure 7G:
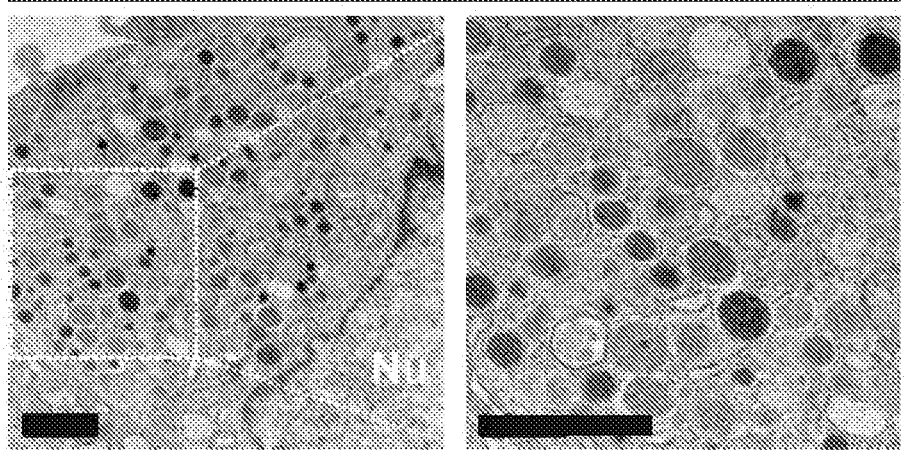
FIG. 7G includes electron microscopy images of granules within sectioned cell. The organoid cells are isolated 1 month after engrafting. Crystallized insulin granules indicating maturation of the β-cells. n=3 mice. Scale bar denotes 1 FIG. 7H includes t-SNE2 plots of 2,129 engrafted hormone-expressing single cells RNAseq profiles (points). Organoids cells are isolated 1 month after engrafting. Data are shown by aligning with the primary single cell RNAseq dataset described above and colored by cluster assignment and annotated post hoc (left), or colored by cell source (right). The engrafted cells were pooled from n=3 mice.
Figure 7H:
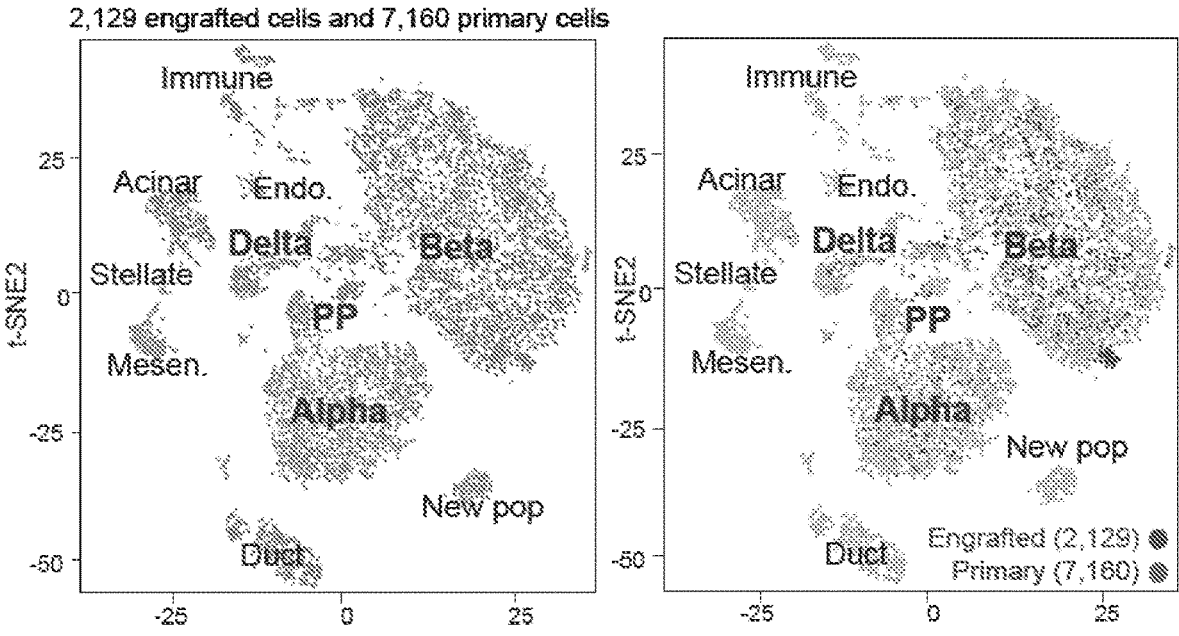
FIGS. 7A-7N demonstrate that long-term cultured organoids restore insulin-dependent glucose homeostasis in streptozotocin (STZ)-induced T1D mice.
FIG. 7B is a graph showing body weight of mice after engrafting. The immunodeficient mice were made diabetic with streptozotocin (STZ) 7 days before engrafting. Body weight changes are routinely checked. The body weight loss of the diabetics can be rescued by engrafting of 1,000 7th or 15th passage islet organoids, similar to the controls engrafting 300 islets. The body weight of unengrafted diabetics continuously decreased. Groups are indicated by colored lines and numbers of mice measured per group are labeled in parentheses. Data are presented as mean±s.e.m.
FIG. 7C is a graph of a glucose tolerance test (GTT) administered 1 month after engrafting that indicates significantly improved glucose tolerance in both organoids engrafted and islets engrafted groups. Groups are indicated by colored lines and numbers of mice analyzed per group are labeled in parentheses. Data are presented as mean±s.e.m.
FIG. 7D is a graph showing ELISA measurements of serum insulin for each indicated group before and after glucose injection (15 minutes after glucose injection). The number of mice used per group are the same as in FIGS. 7A and 7C. Data are presented as mean±s.e.m.
FIG. 7I is a graph showing the distributions of the number of UMIs per cell (left) and the number of genes detected per cell (right) for the engrafted single cell (sc) RNAseq dataset.
FIG. 7J includes t-SNE plots of Sc RNAseq profiles (points) of engrafted or primary samples in split view, colored by cluster assignment and annotated post hoc. Cell counts of indicated samples and cell types are labeled in parentheses. "Mesen." denotes mesenchymal; "Endo." denotes endothelial; "New pop." denotes new population.
FIG. 7K is a heat map for signature genes of endocrine cell types. Each column represents a single cell and each row represents one signature gene. To compare the similarities, engrafted or primary cells are shown separately. The shading ranging from dark shading to lighter shading indicate low to high relative gene expression levels, respectively.
FIG. 7L includes Vlin plots showing the comparable expression levels (Log 2(TPM+1)) of α- or β-cell marker genes between primary and engrafted cells.
FIG. 7M is a dot plot for signature genes of endocrine cell types. Engrafted or primary cells are separately shown for comparison. The shadings denote average expression levels and the sizes of dots denote fractional expression.
Figure 7I:
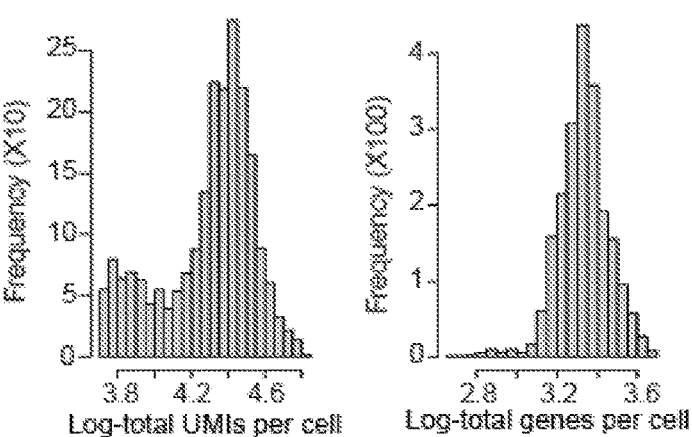
Figure 7J:
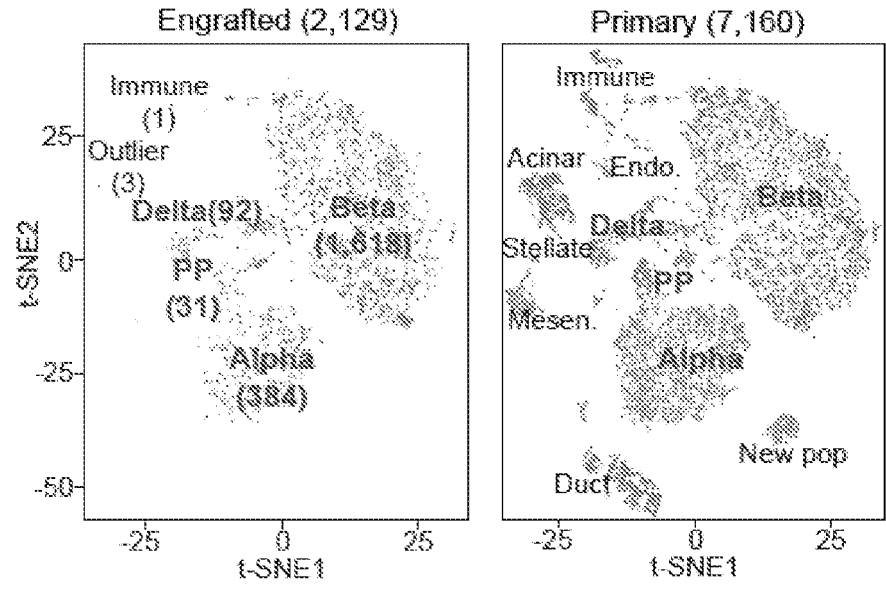
Figure 7K:
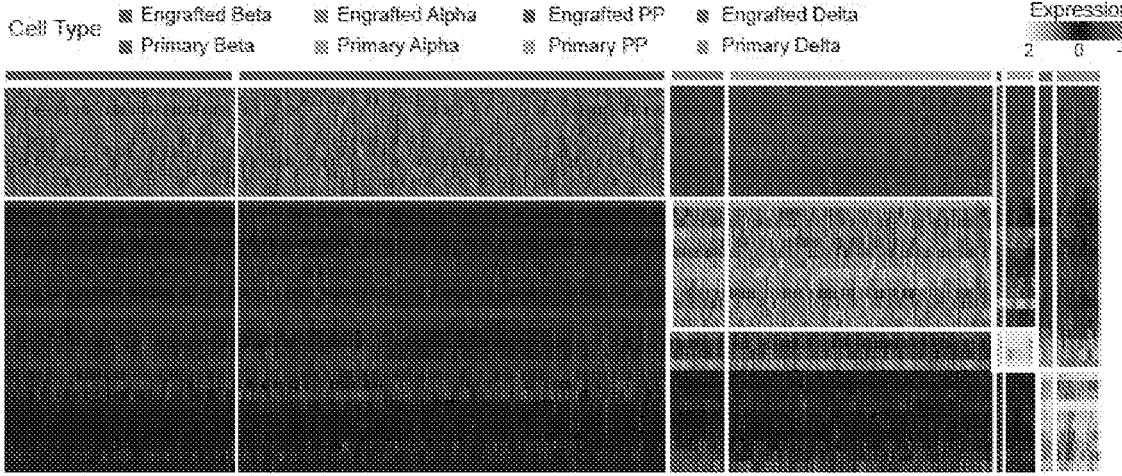
Figure 7L:
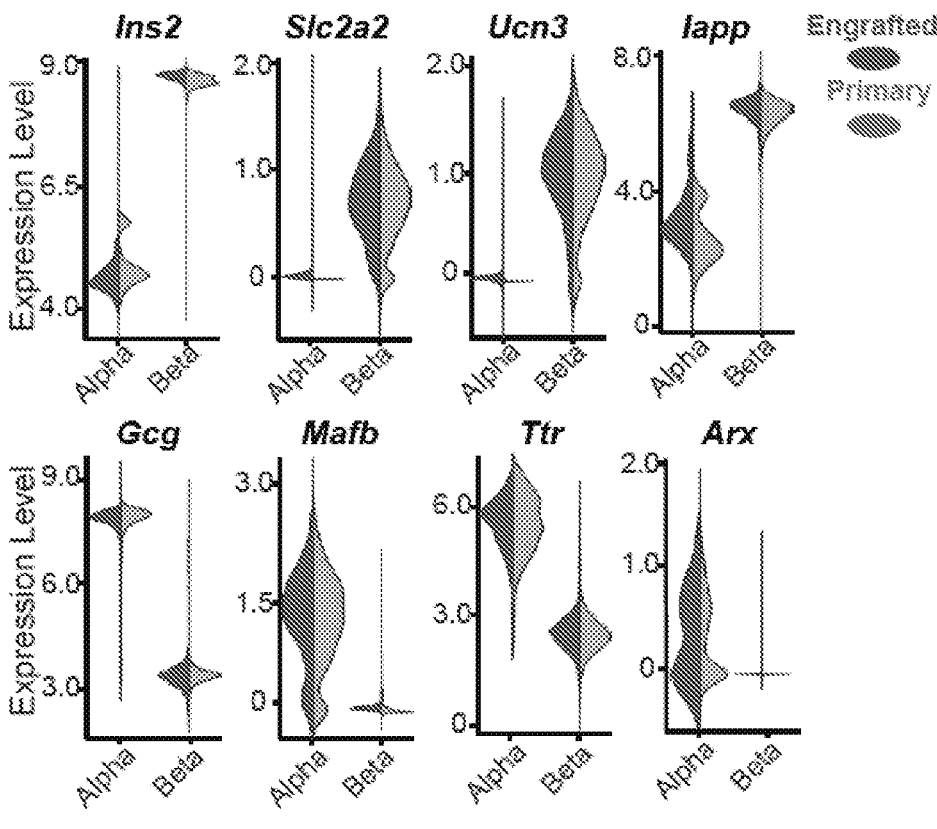
Figure 7M:
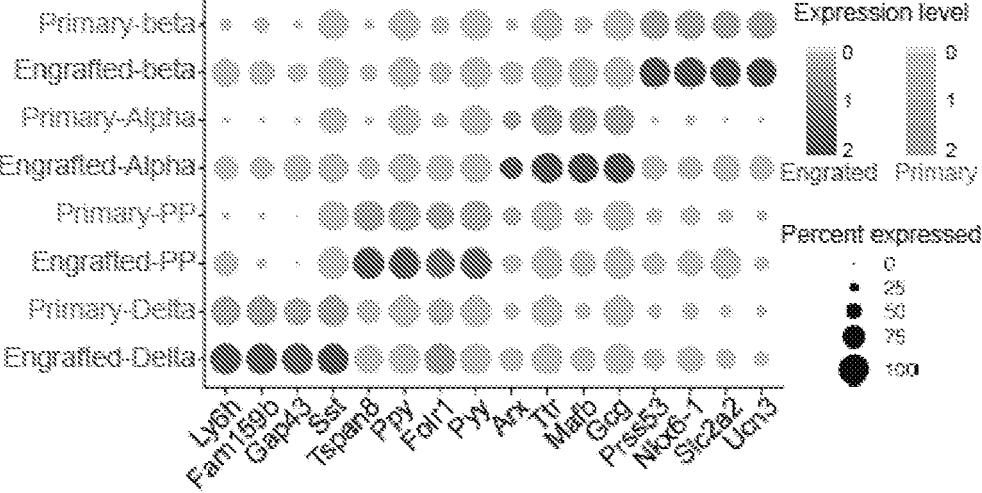

The grafted organoid cells were removed and analyzed 1 month after transplantation. All four endocrine cells types were detected with the vast majority being Ins$^+$ β-cells (FIGS. 7E-7F). The grafted cells also contained a high density of endocrine granules as shown by TEM (FIG. 7G). The identities of these cells were further analyzed by sc RNAseq. The grafted cells, after maturation in vivo, clustered with primary endocrine cells (FIG. 7H-7K). In particular, the genes that encode islet cell markers, hormones, and transcriptional regulators were expressed at comparable levels between the primary mouse endocrine cells and the grafted organoid cells (FIG. 7L-7N).

Discussion

In the current study, we identify a population of endocrine progenitor cells in adult mouse pancreas. These cells do not express known mature endocrine cell markers, feature EMT characteristic, and express Procr on their surface. Isolated Procr+ islet cells can grow in clonal density into islet-like organoids, which comprise all endocrine cell types and are capable of glucose-sensing and insulin secretion. These organoids can be exponentially expanded in vitro by serial passage over long periods. The long-term cultured islet-like organoids can reverse diabetes in vivo.

EMT plays a pivotal role during pancreatic islet formation. Committed endocrine precursor cells detach from the trunk epithelium, presumably via EMT, before the formation of the endocrine islets (Rukstalis and Habener, 2007). It has also been proposed that—at later stages—ductal cells can serve as facultative endocrine progenitors, which is thought to happen through reawakening of the embryonic EMT process (Al-Hasani et al., 2013). Under specific culture conditions, β-cells can undergo EMT, and dedifferentiate to lose their mature characteristics. The resultant fibroblast-like cells can be extensively expanded, and redifferentiation into endocrine cell types (Gershengorn et al., 2004; Ouziel-Yahalom et al., 2006; Russ et al., 2008). In the current study, we identify a population of cells in healthy adult islets, that appear to be in a partial EMT state, co-expressing epithelial markers and mesenchymal markers. Intriguingly, a counterpart cell population also appears to exist within the embryonic endocrine precursor cell population, with similar EMT characteristic and shared signature genes such as Procr, Rspo1, Hoxa5 and Dcn etc. The Ngn3$^+$ endocrine precursor represents a transient cell type in the embryonic pancreas. While the majority of Ngn3$^+$ endocrine precursors lose their precursor state after maturation into endocrine cells, it appears likely that a subpopulation is retained in an endocrine progenitor state post organogenesis. This reserve population no longer expresses Ngn3, but it retains EMT features and the indicated signature genes. Using Ngn3-Cre mediated lineage tracing, we confirm that Procr$^+$ cells (endocrine progenitors) descend from Ngn3$^+$ endocrine precursors.

As an alternative source of these cells, we cannot formally rule out the ductal tree. There is growing body of evidence for the existence of a pancreas progenitor pool within the ductal tree of the adult pancreas. Severe damage to the pancreas can stimulate non-endocrine precursors, such as duct cells, to proliferate and differentiate towards acinar (Criscimanna et al., 2011; Furuyama et al., 2011), duct (Criscimanna et al., 2011; Furuyama et al., 2011; Kopp et al., 2011), and also endocrine lineages (including –cells) (Criscimanna et al., 2011; Inada et al., 2008; Pan et al., 2013; Van de Casteele et al., 2013; Xu et al., 2008). In the current study, we analyze Procr$^+$ endocrine progenitors at the state when they already physically reside in islets. We visualize these cells by LacZ and mGFP knock-in reporter, we FACS-isolate these cells by EpCAM+ and Procr+ surface marker in hand-picked islets. We further interrogate their clonogenicity, expansion and multipotent endocrine lineage differentiation capacities in culture.

Identifying a reservoir of endocrine progenitor cells in the pancreas itself allows for either in situ or ex vivo expansion approach to increase β-cell mass. The current study explores the latter possibility. We harness the expansion and differentiation capacities of the endocrine progenitors, by establishing a culture system for the expansion and induction of the islet-like organoids. The resulting organoids are dominated by β-cells surrounded by a mantle of α-, δ- and PP-cells. We demonstrate these organoids to be a useful cell source for ameliorating diabetes in mouse model. Increasing evidence indicates that proper glucose regulation requires coordination between the various islet cell types (Johnston et al., 2016; van der Meulen et al., 2015). It may therefore be advantageous to produce whole islets in vitro rather than to differentiate cells into a specific cell type.

In summary, this study identifies a novel endocrine progenitor in adult mouse pancreas, and establishes an in vitro method for long-term expansion and induction of islet-like organoids. Eventually, this progenitor population may be exploited for their existence in human and treatment of diabetes.

Methods

| Key Resources Table | | |
| --- | --- | --- |
| REAGENTS or RESOURCE | SOURCE | IDENTIFIER |
| Antibodies | | |
| FITC anti mouse CD31 (clone MEC 13.3) | BD | cat#553372; RRID: AB_394818 |
| FITC anti mouse CD45 (clone 30-F11) | BD | cat#553079; RRID: AB_394609 |
| FITC anti mouse Ter119 (clone TER-119) | BD | cat#557915; RRID: AB_396936 |
| Biotin anti mouse CD31 (clone MEC 13.3) | BD | cat#553371; RRID: AB_394817 |
| Biotin anti mouse CD45 (clone 30-F11) | BD | cat#553080; RRID: AB_394610 |
| Biotin anti mouse Ter119 (clone TER-119) | BD | cat#553672; RRID: AB_394985 |
| PE anti mouse Procr (clone 1560) | eBioscience | cat#12-2012-82; RRID: AB_914317 |
| APC anti mouse Procr (clone 1560) | eBioscience | cat#17-2012-82; RRID: AB_11041975 |
| PE-Cy7 anti mouse EpCAM (clone G8.8) | Biolegend | cat#118216; RRID: AB_1236471 |
| Rabbit anti-mouse Insulin (polyclonal) | Proteintech | cat#15848-1-AP; RRID: AB_10597100 |

-continued

| Key Resources Table | | |
|---|---|---|
| REAGENTS or RESOURCE | SOURCE | IDENTIFIER |
| Mouse anti-mouse Gcg (clone K79bB10) | Sigma | cat#G2654; RRID: AB_259852 |
| Mouse anti-mouse Insulin (clone K36AC10) | Sigma | cat#I2018; RRID: AB_260137 |
| Rabbit anti-mouse Sst (polyclonal) | Sigma | cat#HPA019472; RRID: AB_1857360 |
| Mouse anti-mouse Sst (clone ICDCLS) | eBioscience | cat#13-9751-82; RRID: AB_2572823 |
| Goat anti-mouse Ppy (polyclonal) | Sigma | cat#SAB2500747; RRID: AB_10611538 |
| Rat anti-mouse EpCAM (clone G8.8) | eBioscience | cat#17-5791-82; RRID: AB_2716944 |
| Rabbit anti-mouse Col1a1 (polyclonal) | Abcam | cat#ab34710; RRID: AB_731684 |
| Chicken anti-GFP (polyclonal) | Thermo | cat#A10262; RRID: AB_2534023 |
| Chemicals, Peptide and Recombinant Proteins | | |
| RNAiso plus | Takara | cat#9109 |
| HEPES | Sigma | cat#H4034 |
| Type IV collagenase | Worthington | cat#LS004189 |
| HBSS | Thermo | cat#C14175500CP |
| DMEM/F12 | Hyclone | cat#SH30023.01B |
| DMEM 1640 | Gibco | cat#C11875500 |
| Histopaque-1077 | Sigma | cat#10771 |
| 0.05% trypsin-EDTA | Gibco | cat#25300 |
| DNase I | Sigma | cat#D4263 |
| TSQ | Invitrogen | cat#M668 |
| Matrigel | BD | cat#354230 |
| Penicillin-Streptomycin | Thermo | cat#15140-122 |
| B27 | Thermo | cat#0080085-SA |
| ITS | Thermo | cat#41440 |
| EGF | BD | cat#354001 |
| Heparin | Sigma | cat#H4784 |
| FGF2 | Sigma | cat#SRP2092 |
| VEGFa | R&D | cat#494-VE-005 |
| Dispase | BD | cat#354235 |
| Formaldehyde | Sigma | cat#F8775 |
| Glutaraldehyde | Sigma | cat#G6257 |
| NP-40 | Sigma | cat#NP40S |
| $K_3[Fe(CN)_6]$ | Sigma | cat#455946 |
| $K_4[Fe(CN)_6]$ | Sigma | cat#455989 |
| $MgCl_2$ | Sigma | cat#449172 |
| X-gal | Takara | cat#9031 |

-continued

| Key Resources Table | | |
|---|---|---|
| REAGENTS or RESOURCE | SOURCE | IDENTIFIER |
| PFA | Sigma | cat#P6148 |
| Triton-X 100 | Sigma | cat#T9284 |
| DAPI | Thermo | cat#D1306 |
| OCT | Thermo | cat#D6506 |
| Streptozotocin | Sigma | cat#V900890 |
| Aqueous osmium tetraoxide | Sigma | cat#75632 |
| Epon812 | Sigma | cat#45347 |
| Fluo4-AM | Thermo | cat#F14201 |
| Fetal bovine serum | PAN | cat#P30-3302 |
| Glucose | Sigma | cat#47829 |
| Uranyl acetate | Sigma | cat#73943 |
| Lead citrate | Sigma | cat#15326 |
| DMSO | Sigma | cat#D2650 |
| Critical Commercial Assays | | |
| SYBR green Mix | Roche | cat#04913914001 |
| PrimeScript RT master Mix | Takara | cat#RR036A |
| Ultra-sensitive insulin ELISA Kit | APLCO | cat#80-INSMSU-E01 |
| Chromium Single cell 3' library kit v2 | 10X genomics | cat#PN-120233 |
| OneTouch glucometer | Roche | cat#06988547022 |
| Deposited Data | | |
| Single-cell RNA-seq datasets | this paper | OEP000249, OEP000250 |
| Experimental Models: Organisms/Strains | | |
| Ngn3-Cre | Jackson lab | #006333 |
| Rosa26-tdTomato | Jackson lab | #007909 |
| FVB/NJ | Jackson lab | #001800 |
| C57BL/6 | Jackson lab | #000664 |
| Nude | Jackson lab | #002019 |
| Actin-DsRed | Jackson lab | #006051 |
| ICR | SLAC | N/A |
| Procr$^{mGFP-2A-LacZ}$ | this paper | N/A |
| Software and Algorithms | | |
| Graphpad Prism 6 | Graphpad software | www.graphpad.com |
| Adobe Photoshop CC2017 | Adobe | www.adobe.com/product/photoshop.html |
| Adobe illustrator CC2017 | Adobe | www.adobe.com/product/photoshop.html |
| Imaris v8.2 | Imaris | imaris.oxinst.com |
| Rstudio | Rstudio | www.rstudio.com |

-continued

| Key Resources Table | | |
|---|---|---|
| REAGENTS or RESOURCE | SOURCE | IDENTIFIER |
| Flow Jo vX | Flow Jo | www.flowjo.com |
| Cell Ranger v2 | 10X genomics | support.10xgenomics.com |
| Loupe Cell Browser | 10X genomics | support.10xgenomics.com |
| Seurat R package v3 | Butler et al., 2018 | satijalab.org/seurat/ get_started_v1_2.html |
| Monocle R package v2 | Qiu et al., 2017 | cole-trapnell- lab.github.io/monocle-release/ |
| DAVID 6.8 | LHRI | david.ncifcrf.gov/home.jsp |
| Oligonucleotides | | |
| mouse Hprt qPCR forward primer: TCAGTCAACGGGGGACATAAA | this paper | N/A (SEQ ID NO: 1) |
| mouse Hprt qPCR reverse primer: GGGGCTGTACTGCTTAACCAG | this paper | N/A (SEQ ID NO: 2) |
| mouse Procr qPCR forward primer: CTCTCTGGGAAAACTCCTGACA | this paper | N/A (SEQ ID NO: 3) |
| mouse Procr qPCR reverse primer: CAGGGAGCAGCTAACAGTGA | this paper | N/A (SEQ ID NO: 4) |
| mouse Rspo1 qPCR forward primer: GCAACCCCGACATGAACAAAT | this paper | N/A (SEQ ID NO: 5) |
| mouse Rspo1 qPCR reverse primer: GGTGCTGTTAGCGGCTGTAG | this paper | N/A (SEQ ID NO: 6) |
| mouse Fgf1 qPCR forward primer: CAGCTCAGTGCGGAAAGTG | this paper | N/A (SEQ ID NO: 7) |
| mouse Fgf1 qPCR reverse primer: TGTCTGCGAGCCGTATAAAAG | this paper | N/A (SEQ ID NO: 8) |
| mouse Upk3b qPCR forward primer: AGACCTGATTGCCTACGTGC | this paper | N/A (SEQ ID NO: 9) |
| mouse Upk3b qPCR reverse primer: GGTGTCCTTAGTTGAGACATGCT | this paper | N/A (SEQ ID NO: 10) |
| mouse Hoxa5 qPCR forward primer: CTCATTTTGCGGTCGCTATCC | this paper | N/A (SEQ ID NO: 11) |
| mouse Hoxa5 qPCR reverse primer: ATCCATGCCATTGTAGCCGTA | this paper | N/A (SEQ ID NO: 12) |
| mouse Ins1 qPCR forward primer: TGGCTTCTTCTACACACCCAAG | this paper | N/A (SEQ ID NO: 13) |
| mouse Ins1 qPCR reverse primer: ACAATGCCACGCTTCTGCC | this paper | N/A (SEQ ID NO: 14) |
| mouse Mafa qPCR forward primer: GTCATCCGACTGAAACAGAA | this paper | N/A (SEQ ID NO: 15) |
| mouse Mafa qPCR reverse primer: GCCAACTTCTCGTATTTCTC | this paper | N/A (SEQ ID NO: 16) |
| mouse Ucn3 qPCR forward primer: AAGCCTCTCCCACAAGTTCTA | this paper | N/A (SEQ ID NO: 17) |
| mouse Ucn3 qPCR reverse primer: GAGGTGCGTTTGGTTGTCATC | this paper | N/A (SEQ ID NO: 18) |
| mouse Pdx1 qPCR forward primer: CCCCAGTTTACAAGCTCGCT | this paper | N/A (SEQ ID NO: 19) |

-continued

| Key Resources Table | | |
| --- | --- | --- |
| REAGENTS or RESOURCE | SOURCE | IDENTIFIER |
| mouse Pdx1 qPCR reverse primer:<br>CTCGGTTCCATTCGGGAAAGG | this paper | N/A (SEQ ID NO: 20) |

Experimental Animals

Rosa26-tdTomato, Ngn3-Cre, Actin-DsRed, Procr$^{mGFP\text{-}2A\text{-}LacZ}$, wild-type CD1, C57BL/6, FVB/NJ, and Nude mice were used in this study. The Procr$^{mGFP\text{-}2A\text{-}Lanz}$ mouse strain was generated by knocking in a cassette of mGFP-2A-LacZ behind start codon of the Procr gene.

The targeting construct, southern blot validation, and genotyping methods are shown in FIGS. 3G-3I. All the animal experimental procedures were approved by the Animal Care and Use Committee of Shanghai Institute of Biochemistry and Cell Biology, Chinese Academy of Sciences, with a project license number of IBCB0065.

Islets Enrichment and Purification

Mouse pancreas was perfused by injection of 2-4 ml digestion buffer (DMEM 1640 medium containing type IV collagenase (1000-1500 U/ml), 10% FBS (fetal bovine serum), and 25 mM HEPES) from the common duct. The pancreas was then dissected carefully to keep the integrity of the perfused tissue and then incubated at 37° C. for 5-6 min followed by gently shaking for 3-6 min. The proper perfusion and digestion time are critical for islet yield and structure integrity. After digestion, the tissue was suspended in 20 ml HBSS with 10% FBS and rigorously shaken up and down 40 times within 20 seconds and followed by two HBSS washes. The digested tissue was then filtered with 500 μm cell strainers. To enrich islets, the filtered sample underwent density gradient centrifugation or was transferred under the microscope for hand-picking of islets. To prepare the density gradient centrifugation, the tissue was first re-suspended in 10 ml histopaque-1077 and slowly covered by 10 ml HBSS without breaking the interface. The re-suspended tissue was centrifuged at 2,400 rpm for 22 min with the slowest acceleration and braking to obtain the enriched islets compartment at the HBSS/histopaque-1077 interface. The purity of islets ranged from about 20% to 70% after the density gradient centrifugation step, depending on the quality of earlier perfusion and digestion process. To ensure high purity of islets, the samples were re-suspended in HBSS with 10% FBS for hand-pick. Islets with high purity were hand-picked under dissecting microscope for at least 3 rounds.

Islets X-Gal Staining

X-gal staining of purified islets was performed following the standard protocol with minor changes. In brief, islets were fixed in Fix A solution (1% Formaldehyde, 0.2% Glutaraldehyde, 0.02% NP-40 in PBS) at 4° C. for 30 min, washed 3 times with PBS, then stained in X-gal staining solution (1 mg/ml X-gal, 5 mM K$_3$[Fe(CN)$_6$], 5 mM K$_4$[Fe(CN)$_6$], 2 mM MgCl$_2$ in PBS) at room temperature for 5 h. After staining, islets were washed with PBS and the whole mount images were captured by Zeiss inverted microscope.

Immunofluorescence, Whole Mount Staining and Microscopy

To prepare samples for frozen sections, the dissected pancreas was fixed in 4% PFA at 4° C. for 4 h, washed 3 times with PBS and then embedded with Optimum Cutting Temperature (OCT). Tissue sections were incubated with primary antibodies at 4° C. overnight, followed by washing in PBST (PBS+0.1% Triton-X 100) and incubation with secondary antibodies and DAPI for 2 h at room temperature. The sections were then washed and mounted for confocal imaging.

To perform whole mount staining, islets or cultured organoids were fixed in 4% PFA at 4° C. for 1 h followed by 3 PBS washes. The islets or cultured organoids were then blocked with the whole mount blocking buffer at room temperature for 1 h. The blocking buffer contained 10% FBS in PBST. Primary antibodies were diluted in blocking buffer and incubated at 4° C. overnight after washing 3 times with PBST. The secondary antibodies and DAPI were incubated at 4° C. overnight. Islets or organoids were then washed and mounted with mounting medium for confocal imaging.

All confocal images were captured by Leica SP8 confocal detection system fitted on a Leica DMI6000 microscope.

Preparation of Islets Single Cell Suspension and FACS Analysis

Purified islet samples were treated with 2 ml 0.05% trypsin-EDTA at 37° C. for 4 min, followed by digestion with 0.1 mg/ml DNase I for 4 min and gently pipetting the sample about 20 times. The digested cells were filtered through a 70 μm cell strainer.

For FACS analysis and cell sorting, antibody incubation was performed on ice for 25 min in HBSS with 5% FBS at a dilution of 1:200. All analyses and sorting experiments were performed using FACS Jazz (Becton Dickinson). The purity of the sorted population was routinely checked and ensured to be more than 95%.

Co-Culture and Passage of Mouse Pancreatic Islet Organoids

200 μl basement membrane matrix MATRIGEL™ was coated in one well of a 48-well plate and transferred into 37° C. ESCO incubator to gel. Mouse islet EpCAM+, Procr +/− cells were F ACS-sorted from handpicked islets of wild-type CD1, C57BL/6, or FVB mice. CD3 1+ endothelial cells (ECs) were F ACS-isolated from inguinal fat pad or skin of Actin-DsRed mice. Islet cells and ECs were mixed in a ratio of 1:3 and plated within 500 μl mouse organoid medium comprising DMEM/Fl2 (with penicillin-streptomycin) plus 2% B27, 1% ITS, 50 ng/ml EGF, 2 μg/ml heparin, 10 ng/ml FGF2, and 5 ng/ml VEGFa. The medium was refreshed every 2-3 days. To induce J3-cell maturation, glucose challenges were performed. 20 mM glucose in HBSS was mixed with the organoid medium in a 1:1 ratio to prepare high glucose medium with a final concentration of 11 mM glucose. Organoids were first cultured for 12 h in low glucose (2 mM) followed by 12 h treatment in high glucose (11 mM) for 3 rounds.

Organoids were passaged every 6-14 days. For passage, organoids were released from the basement membrane matrix MATRIGEL™ using dispase (37° C. for 40 min) and dissociated into single cells with 1 ml 0.05% trypsin-EDT A (37° C. for 6-9 min). The single cell suspension was mixed with freshly isolated CD3 1+ECs in a 1:1 ratio followed by replating in a 1:4-6 split ratio.

Glucose-Stimulated Insulin Secretion

About 100 mouse organoids at day 28 culture were used. The organoids were first washed 3 times with Krebs buffer, then pre-incubated in low glucose (2 mM) for 2 h to remove residual insulin. The organoids were then washed 2 times in Krebs buffer followed by incubation in low-glucose for 30 min. The supernatant samples were collected, and organoids were washed 2 times in Krebs buffer followed by incubation in high glucose (20 mM) for 30 min, and the supernatant samples were collected. This process was repeated twice. Insulin levels contained in the supernatant samples were analyzed using mouse Ultrasensitive Insulin ELISA kit following standard protocols.

Transmission Electron Microscope (TEM)

To prepare samples for TEM, organoids or islets were fixed in 1% glutaraldehyde in 0.1 M sodium cacodylate buffer (pH 7.4) at 4° C. overnight and post-fixed in 2% aqueous osmium tetraoxide at 4° C. for 1.5 h. The samples were then dehydrated in gradual ethanol (30% to 100%) and propylene oxide, embedded in Epon812, and cured for 48 h at 60° C. 50 nm ultrathin sections were collected on 200 mesh copper grids and stained with uranyl acetate (10 min) and lead citrate (5 min) before examination by transmission electron microscopy. Images were captured with FEI Tecnai G2 Spirit Transmission electron microscope.

$Ca^{2+}$ Imaging

Organoids were harvested after dispase dissociation and plated on 35 mm glass bottom dishes without basement membrane matrix MATRIGEL™ for 24 h. The cell clusters were washed twice with Krebs buffer and incubated with Fluo4-AM for 30 min. The Fluo4-AM was washed out with Krebs buffer, and the cell clusters were incubated in 3 7° C. for an additional 15 min without the dye. The cell clusters were then staged on a Nikon AI inverted confocal microscope for the acquisition of high-resolution time series images. Time series images were acquired every 10 s. Conditions for the progression of glucose challenges and time of stimulation during imaging were as follows: 5 min in low glucose (2 mM), Krebs wash, 5 min in high glucose (20 mM), Krebs wash. This sequential treatment was performed three times, and then a final incubation for 5 min with 2 mM glucose containing 30 mM KCl was performed. For the measurement of the average fluorescence intensity, images were quantified by Imaris software (v8.2.0).

Transplantation in Diabetic Mice

Nude recipients were induced diabetes with a single intraperitoneal injection of streptozotocin (STZ, 160 mg per kg in pH 4.5 citrate buffer) 7 days prior to engraft. Nonfasted blood glucose was measured from tail vein samples with a OneTouch glucometer to select the diabetic recipients with blood glucose level increased to about 20 mM. 300 mouse islets or 1,000 organoids (7th or 15th passage, at day 7 culture) were engrafted underneath the kidney capsule of recipient mice. Nonfasted blood glucose and body weight were routinely measured after engrafting for 1 month. Glucose tolerance tests (GTTs) were performed following standard protocol 1 month after engrafting. In brief, mice were fasted overnight and received an intraperitoneal injection of 2 g per kg body weight glucose. Blood glucose levels were measured at 0, 15, 30, 60, 90, and 120 min after glucose challenges. Serum samples before and after glucose injection were also collected and measured by ELISA. Recipients were sacrificed 1 month after engrafting, and the regenerated tissues were harvested for section and endocrine markers staining or digested into single cells for transmission electron microscope analysis and 10× sc RNA-sequencing.

RNA Isolation and qPCR

RNA isolation of primary cells or organoids were performed following manufacturer instructions. Samples were lysed in RNAiso plus. Extracted RNA was reverse transcribed into cDNA using the Primerscript RT master kit. qPCR samples were prepared with SYBR Green Mixture and detected using Applied Biosystems Stepone Plus machine. All qPCR primers were listed in Key Resource Table above.

Single Cell RNA Sequencing with 10× Genomics Chromium Platform

For the primary pancreatic single cell RNAseq, 3 biological replicates were performed with ICR mice used in replicate-1 and replicate-2 and C57BL/6 mice used in replicate-3. Islets were enriched by density gradient centrifugation as described above. To minimize the damage of exocrine enzymes released during tissue dissociation, hand-picking of islets was not performed as a purification step (hand-picking islets required at least 1 h at room temperature). Alternatively, TSQ (6-methoxy-8-p-toluenesulfonamido-quilone) was used to enrich endocrine cells by FACS sorting (Huch et al., 2013). The cells were re-suspended in a solution containing TSQ (0.2 mg/ml). After FACS sorting, the endocrine (TSQ$^+$) and non-endocrine (TSQ) compartments were mixed together at a 1:1 ratio to form one sequencing sample. The cell quality was checked under the microscope before loading onto the 3' library chip and cell viability was ensured to be higher than 75%, with over 90% of cells ensured as singlets. 13,000 single cells were loaded, with a recovery of 3,706; 2,349; and 1,111 cells. Respectively, for each biological replicate. The output ratio between endocrine and non-endocrine compartments was higher than 1:1. This may have been due to the relative larger size of acinar cells, leading to them being underrepresented when using the 10× Genomics method (see below).

To retrieve the grafted cells for sequencing, the transplant was carefully dissected from the kidney, followed by mincing and digestion of the transplant with trypsin-EDTA and DNase I. Dissociated single cells underwent FACS sort for TSQ$^+$ cells, which were sequenced and then compared to primary mouse islet cells. 13,000 engrafted cells pooled from 3 recipient mice (1 mouse transplanted with 7th organoid and 2 mice with 15th organoid) were loaded, with a recovery of 2,129 cells.

For the library preparation, single cells were loaded onto 3' library chips for the Chromium Single Cell 3' Library (V2) according to the manufacturer's recommendations (10× Genomics). In brief, single cells were partitioned into gel beads in emulsion in the GemCode instrument with cell lysis and barcoded reverse transcription of RNA, followed by amplification, shearing, and 5' adaptor and sample index attachment. Libraries were sequenced on an Illumina Hiseq PE150.

Filtering (demultiplexing), alignment to the mm10 transcriptome, and unique molecular identifier (UMI)-collapsing were performed using the Cell Ranger (V2) pipeline (10× Genomics). The Seurat 3 R package was used for data integration, analysis, and visualization as described in Butler et al., Nat Biotechnol 36, 411-420 (2018), the contents of which are hereby incorporated by reference in their entirety. For detail, Seurat object was created by selecting genes expressed in at least two cells and cells that had at least 300 detected genes and 3,000 detected UMIs. Only six cells were filtered from replicate-3 primary pancreatic sample (from 1,111 cells to 1,105 cells). In analyses involving the E14.5 Ngn3$^+$ single cell RNAseq data from Byrnes et al., Nat Commun 9, 3922 (2018) and Scavuzzo et al. Nat Commun 9, 3356 (2018) (the contents of each are hereby incorporated by reference in their entirety), same filtering standards were used for Seurat objects creation and Ngn3+ cells were filtered by Neurog3 UMI>0. Variable genes were found by "vst" method, and the top 2,000 genes were selected for principal component analysis (PCA). Dimensionality reduction was performed with the t-stochastic neighboring embedding method (tSNE). The top 20 principal components (PCs) were used. Cell clustering was based on shared-nearest neighbor (SNN) method, and the resolution value was set to 0.9 for primary cells or primary V.S. engrafted cells and 0.8 for primary V.S. E14.5 Ngn3+ cells. Some clusters were put together as one cell type based on the similarity of the expression profiles and marker genes. For data display, violin plots, heat maps, dot plots, and individual tSNE plots for the given genes were generated by using the Seurat toolkit VlnPlot, DoHeatmap, DotPlot, and FeaturePlot functions, respectively.

Pseudo temporal analysis of primary pancreas cells was performed using the Monocle 2 R package as described in Qui et al., Nat Methods 14, 979-982 (2017), the contents of which are incorporated by reference in their entirety. Alpha, beta, delta, PP and new population cells were directly transferred from Seurat to Monocle 2 for the creation of the monocle CellDataSet object, and 321 cells were further filtered. The top 2,000 variable genes identified by Seurat were used as ordering genes. The "DDRTree" method was used for dimensionality reduction, and the max_components was set to 2 to generate one branching point. The split heat map was generated from selected genes showing significant change through pseudotime (q-value<E-10).

Statistics

Unpaired, two-tailed Student's t-test was performed and the p-value was calculated using GraphPad PRISM 6 when two groups of samples were compared. For all experiments with error bars, the std. error of mean (S.E.M) was calculated to indicate the variation within each experiment.

Data Availability

Sc RNAseq data is available at the website www.biosino.org/node/index, with access NO. OEP000249 and OEP000250.

Example 2: Long-Term Culture and Expansion of Human Pancreatic Islet Organoids Transplantations of islet and whole pancreas from cadaveric organ donation provided the proof-of-concept of glucose homeostasis restoration after replenishment of the deficiency of β cells responsible for the disease (Lysy et al., 2013). Scarcity of donors has led to the search for strategies of generating β-cells in vitro. It has proven challenging to make new β-cells in vitro. Cell therapy for diabetes requires identifying candidate cell sources and new culture strategies. Our previous study (see Example 1) in murine pancreas identified a new population of endocrine progenitor cells. The cells do not express pancreas differentiation markers and can be sorted from islets based on surface Protein C receptor (Procr) expression. These cells can form islet-like organoid in culture that are glucose-responsive, insulin-secreting and can be expanded for long-term. In the current study, we exploited the existence of such an endocrine progenitor population in human and their implication in generating new human beta cells in vitro.

To probe the existence of PROCR+ cells in human islet, immunostaining of PROCR in sections of human pancreas was performed. A small population of PROCR+ islet cells were detected within islets (FIG. 8A). Interestingly, these PROCR+ cells did not express endocrine differentiation markers (FIG. 8A), similar to its counterpart in mice. PROCR+ cells were also found in the exocrine compartment of the human pancreas (FIG. 8B).

Figure 9A:
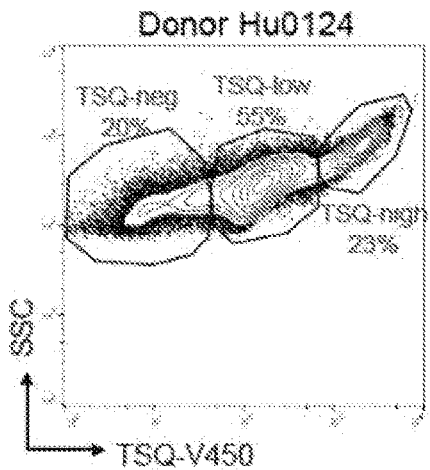
FIGS. 9A-9C illustrate the isolation of human islet single cells by FACS.
Figure 9B:
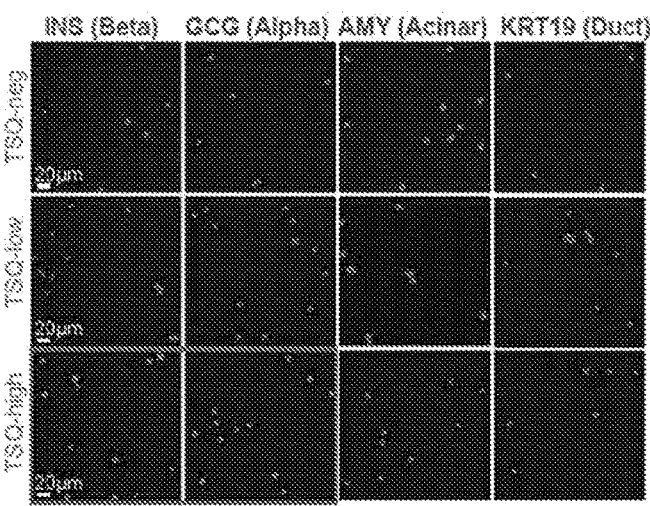

Next, these PROCR+ islet cells were isolated and cultured. The human islets were obtained by collagenase perfusion and density gradient centrifugation, followed by hand-pick purification. Due to the cleavage or endocytosis of PROCR from the cell surface during collagenase perfusion, we were not able to isolate PROCR+ cells from primary islets. However, by experimenting collagenase and other conditions, we believe that PROCR+ cells can be isolated using an anti-PROCR antibody from human islets, similar to mouse experiments in Example 1. Nonetheless, total islet cells from human were cultured. To this end, dissociated single cells were stained with TSQ (6-methoxy-8-p-toluene-sulfonamido-quilone, a fluorescent zinc indicator, for enriching endocrine cells) and underwent positive selection for TSQ+ cells by FACS sorting. Representative FACS profile showed three different levels of TSQ uptake in human islet samples, TSQ-high, TSQ-low, and TSQ-negative (FIG. 9A). These three populations were sorted, followed by cytospin and staining with endocrine (INS, GCG) and exocrine (AMY, KRT19) markers. It was found that the TSQ-high fraction also showed enriched exocrine markers expression (FIG. 9B), consistent with the findings in mouse.

Figure 9C:
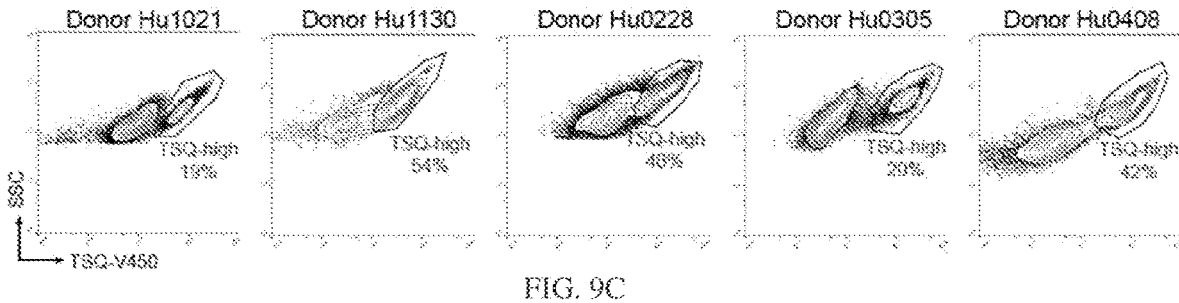
Figure 10A:
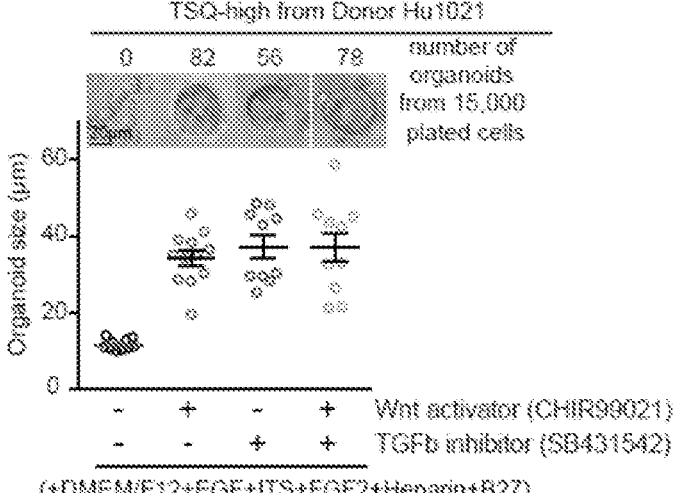
Figure 10B:
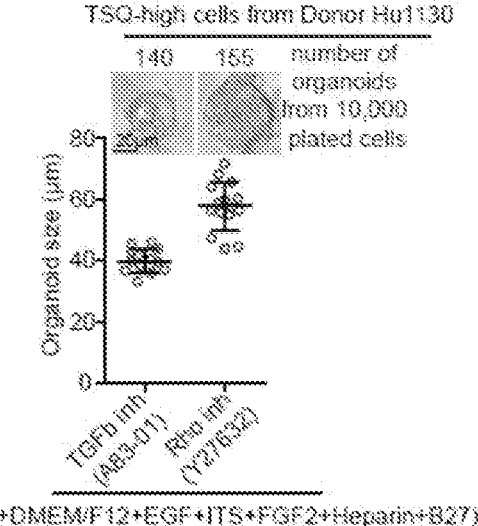

Next, TSQ-high cells (endocrine/islet cells) in 3D culture from various donor tissues were sorted and cultured (FIG. 9C). To establish a culture medium for human islet cells, on the base of a basic medium used in mouse islet organoid culture (DMEM/F12+EGF+ITS+FGF2+Heparin+B27), small molecules and growth factors were screened, including Wnt agonists CHIR99021 or NGS (a Wnt pathway activation peptide), TGF-beta pathway inhibitors SB431542 or A83-01, Rho-ROCK pathway inhibitor Y27632, Bmp agonist Bmp2, or Bmp inhibitor Noggin for the ability to support growth (FIG. 10A-10C). Based on the colony formation rate and colony/organoid size, a growth-promoting condition (DMEM/F12+EGF+ITS+FGF2+Heparin+Y27632+B27+CHIR99021+Noggin+A83-01) was established, which required activation of Wnt, FGF, and BMP signaling and inhibition of the TGFβ and Rho-ROCK pathways (FIG. 10C). Activating Integrin beta 1 antibody (1 nM) can also help growth. Organoids formed in this culture conditions contain majority of INS+ β-like cells and few GCG+ α-like cells (FIG. 10D), resemblance of the cellular composition of human islets.

Islet organoids were generated from three different donors. The organoid forming efficiency was consistently about 0.8% (FIG. 11A), suggesting that the organoids were unlikely formed from contaminated non-endocrine cells. Indeed, endocrine islet organoids and exocrine ductal organoid displayed distinct phenotypes. Islet organoids were more compact, with a "bunch-of-grapes" structure similar to islets (FIG. 11B (day 12)), whereas ductal organoids exhibited a typical "ring-like" structure (FIG. 11B (day 14)). At culture day 18, the organoid sizes ranged from 50-300 μm (FIG. 11C). When dissociated to single cells and replated in the same culture condition, the organoids expanded for 3-9 folds in number during each passage (FIG. 11C), with a slight decrease in average sizes in passaged organoid and maintained stable for many passages (FIG. 11C-11D).

Insulin (INS) expression was examined as an indication of functional β-cell formation. Whole mount immunostaining was performed in primary organoids. The majority of organoid cells exhibited high levels of insulin (FIGS. 12A-12B). These organoids also contained few GCG+ alpha-like cells (FIG. 12A-12B), similar to the observation in mouse islet organoids. Unlike ductal organoids that exhibited ductal marker SOX9 expression (FIG. 12C), the islet organoids did not express SOX9 (FIGS. 12A-12B). In addition, these islet organoids could respond acutely to glucose. The organoid cells rapidly increased cytosolic $Ca^{2+}$ concentrations in response to glucose and subsequently returned to baseline (FIG. 12D). The insulin expression was also confirmed in passaged organoids (FIG. 12E), suggesting that β-cell differentiation can be achieved after long-term culture and expansion.

Figure 13A:
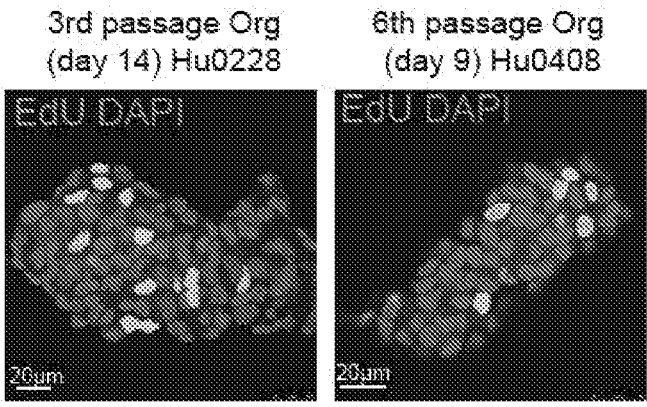
FIGS. 13A-13C demonstrate that $PROCR^+$ cells in organoids are highly proliferative.
Figure 13B:
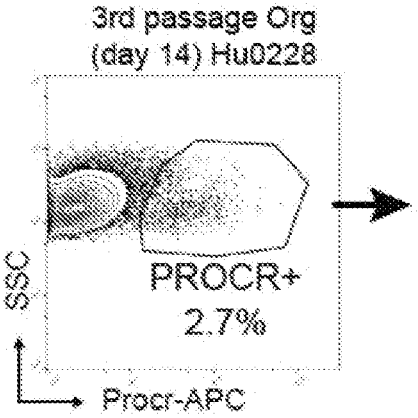
Figure 13C:
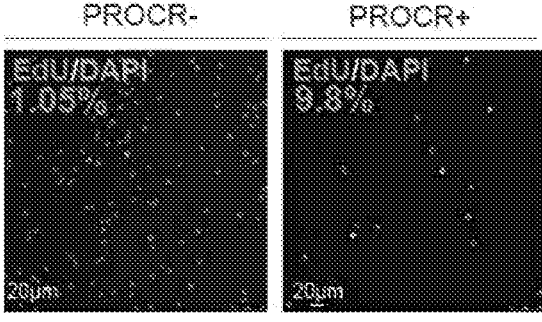

EdU incorporation assay indicated the existence of population of proliferative cells within the organoids (FIG. 13A), suggesting the coexistence of proliferating/undifferentiated cells and differentiated hormone-expressing cells within the organoids. PROCR expression in these organoids was analyzed by FACS. About 2.5% of cells in human islet organoids were Procr$^+$ (FIG. 13B), similar to the Procr+ cell proportion found in mouse islet organoids. Furthermore, Procr$^+$ cells in the organoid exhibited about 10-fold higher EdU incorporation compared to Procr$^-$ cells (FIG. 13C), suggesting that these cells are more proliferative and could be the major contributor of organoid formation.

Together, this data shows that the methods and composition described herein can generate functional human β-like cells in vitro. Isolated human islet cells can grow in clonal density into islet-like organoids, which comprise various endocrine cell types and are capable of glucose-sensing and insulin secretion. These organoids can be exponentially expanded in vitro by serial passage for long-term.

Methods

Patients and Clinical Specimens

All human islets or specimens were obtained from Changzheng Hospital. The use of samples for research was approved by ethical committees and informed consent were obtained from donors.

Statistics

Unpaired, two-tailed Student's t-test was performed, and the p-value was calculated using GraphPad PRISM 6 when two groups of samples were compared. For all experiments with error bars, the standard error of mean (S.E.M) was calculated to indicate the variation within each experiment.

Islets Enrichment and Purification

Human islets enrichment was performed by Changzheng Hospital with standard protocol (perfusion followed by density gradient centrifugation). Islets with high purity were used for clinical transplantation. Islets with lower purity (~5%-20%) were further enriched by hand pick and used in this study. The purity of islets ranged from ~20%-70% based on TSQ staining and FACS analysis.

Preparation of Islets Single Cell Suspension and FACS Analysis

The single cell suspension was obtained by treating purified islets with 2 ml 0.05% trypsin-EDTA at 37° C. for 5 min and 0.1 mg ml$^{-1}$ DNase I for further 5 min, gently pipetting for about 20 times. Then cells were filtered through 70 μm cell strainer.

For FACS analysis of PROCR, antibody incubation was performed on ice for 25 min in HBSS with 5% FBS at a dilution of 1:200. To gate out the exocrine and other cell lineages, dissociated single cells were re-suspended in a solution containing TSQ (0.2 mg ml$^{-1}$). The TSQ-high cells were sorted for culture to ensure the generated organoids were endocrine-derived. All analysis and sorting experiments were performed using FACS Jazz machine (Becton Dickinson). The purity of the sorted population was routinely checked and ensured to be more than 95%.

Establishment of Culture System for Human Islet Organoid Generation and Passage 200 μl basement membrane matrix MATRIGEL™ was coated in one well of 48-well plate and transferred into 37° C. ESCO incubator for solidification. TSQ-high human pancreas cells were F ACS sorted and plated within 500 μl human organoid medium consists of DMEM/Fl2 (with Penicillin-Streptomycin) plus 2% B27, 1% ITS, 50 ng mr1 EGF, 2 μg mr1 heparin, 10 ng mr1 FGF2, 3 μM CHIR99021, 2 μM A83-01, 100 ng mr1 Noggin, 10 μM Y27632. The medium was refreshed every 2-3 days.

Organoids were passaged every 7-21 days. For passage, organoids were released from the basement membrane matrix MATRIGEL™ using dispase (37° C. for 30 min) and dissociated into single cells with 1 ml 0.05% trypsin-EDTA (37° C. for 3-6 min). Then single cells were re-suspended in medium and plated in a split ratio of 1:3-1:8.

Immunofluorescence, Whole Mount Staining and Microscopy

To prepare samples for frozen sections, the dissected pancreas was fixed in 4% PFA at 4° C. for 4 h, washed with PBS for 3 times and then embedded with Optimum Cutting Temperature (OCT). Tissue sections were incubated with primary antibodies at 4° C. overnight, followed by washing in PBST (PBS+0.1% Triton-X 100), incubation with secondary antibodies and DAPI for 2 h at room temperature, then sections were washed and mounted for confocal imaging.

To perform whole-mount staining, human islets or cultured organoids were fixed in 4% PFA at 4° C. for 1 h, followed by 3 times of PBS washing, then blocked with the whole mount blocking buffer at room temperature for 1 h. The blocking buffer contained 10% FBS in PBST. Primary antibodies were diluted in blocking buffer and incubated at 4° C. overnight, after washing with PBST for 3 times, the secondary antibodies and DAPI were incubated at 4° C. overnight. Islets or organoids were then washed and mounted with mounting medium for confocal imaging.

All confocal images were captured by Leica SP8 confocal detection system fitted on a Leica DMI6000 microscope.

Figure 14A:
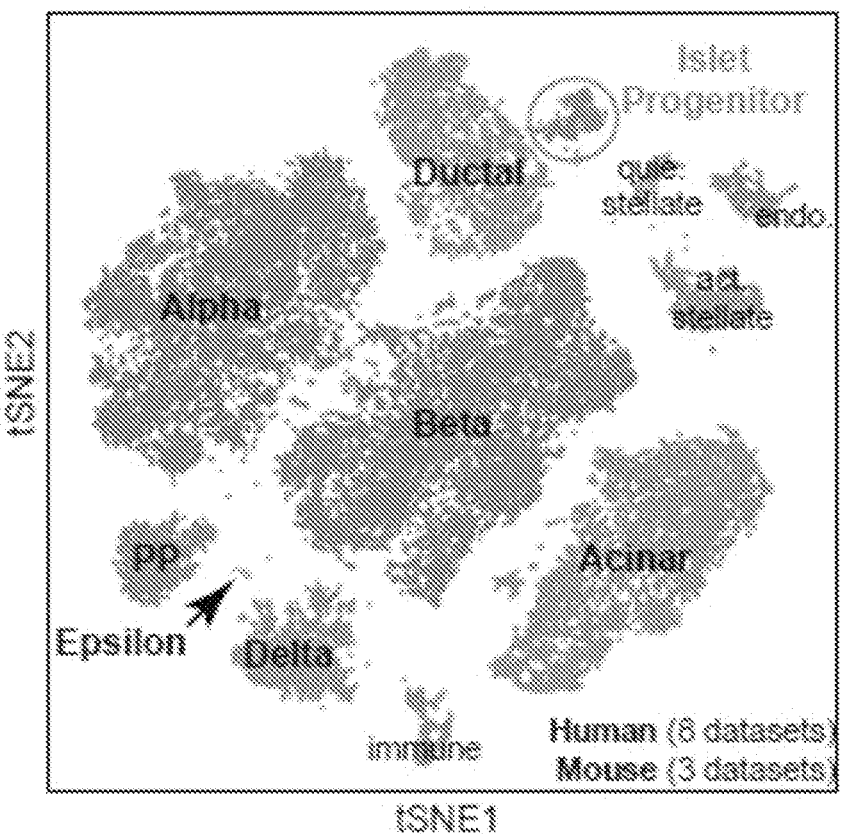
FIGS. 14A-14F. scRNA-seq analysis reveals a potential islet progenitor population in adult human pancreas.
Figure 14B:
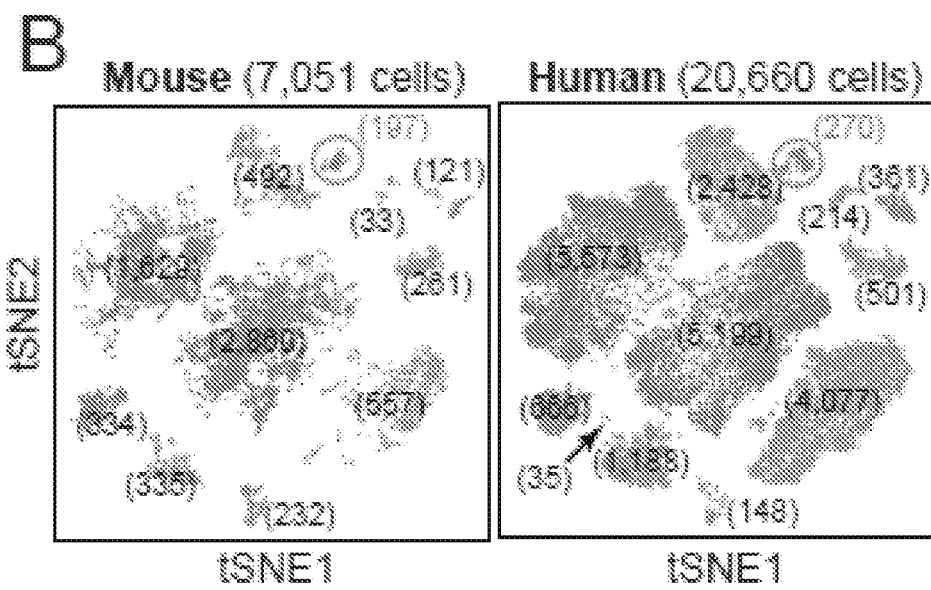
Figure 14C:
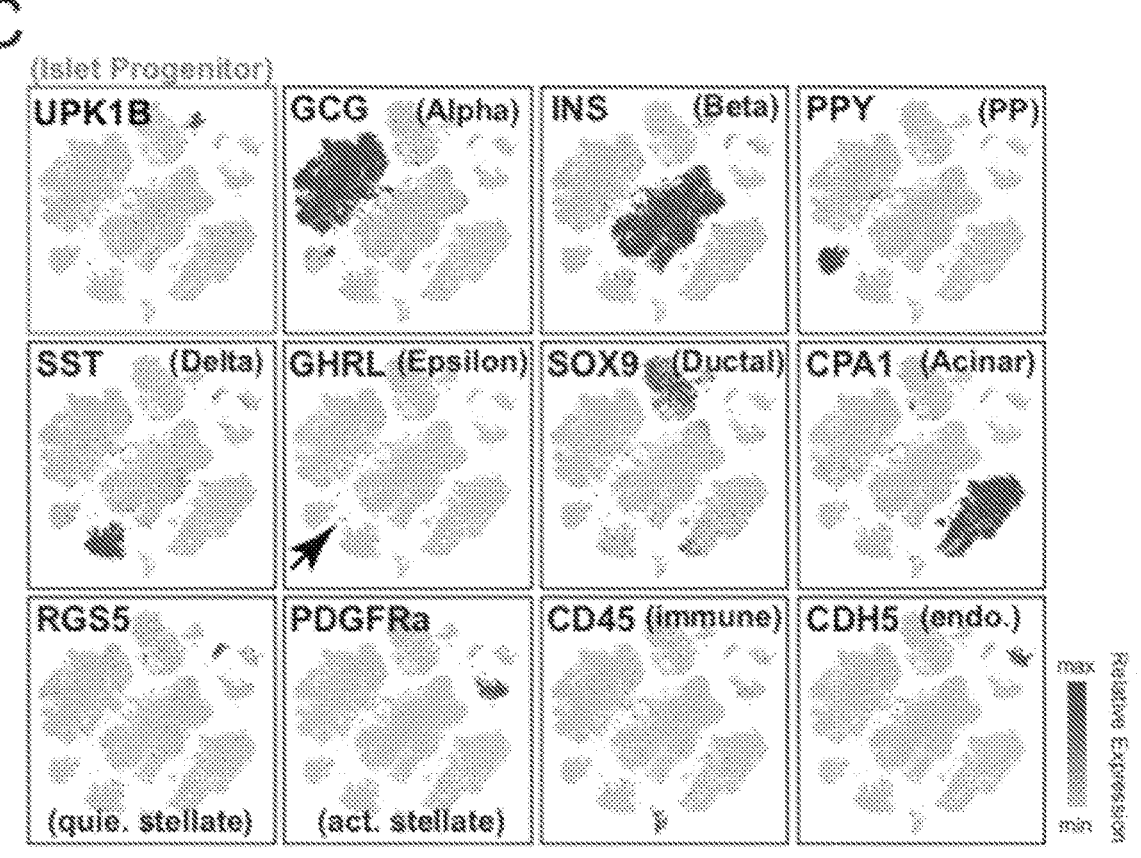
Figure 14D:
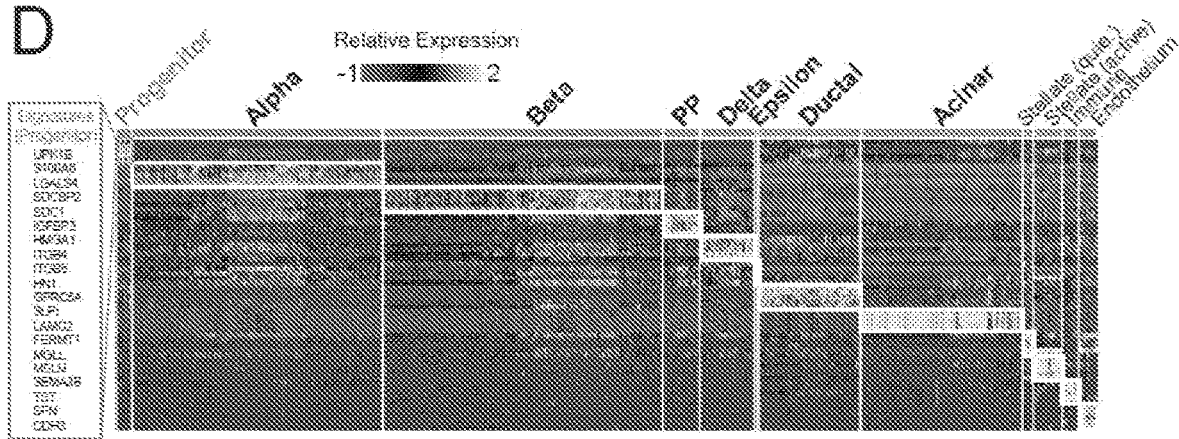
Figure 14E:
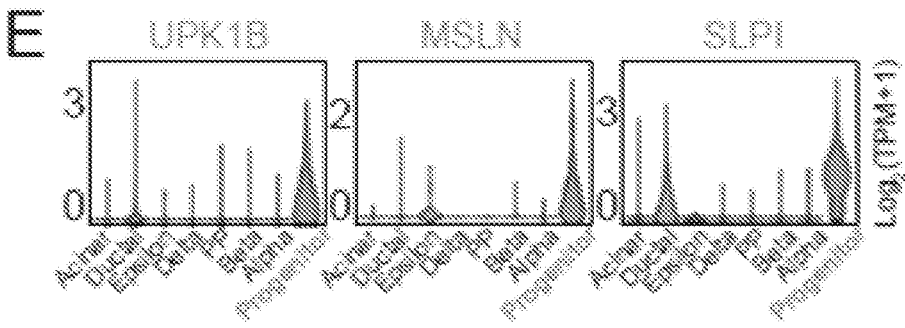
Figure 14F:
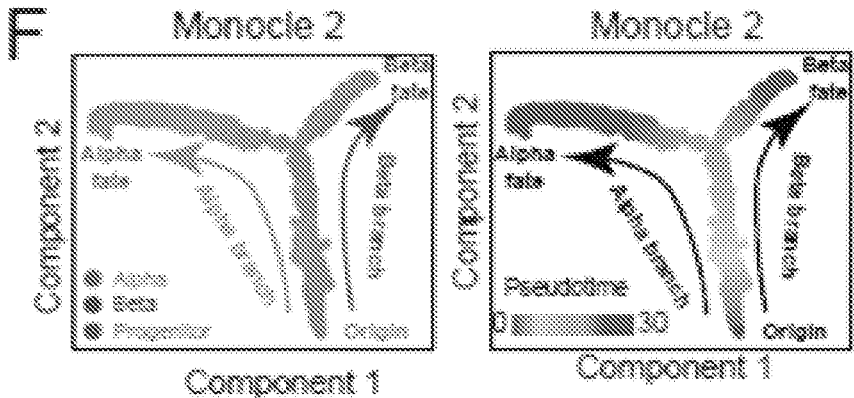

Example 3: Identify Human Adult Pancreatic Endocrine/Islet Progenitors and Culture them into Islet Organoids In Vitro To identify the potential endocrine progenitor population in human, we performed scRNA-seq using dissociated pancreatic cells from 2 donors. They were combined with published human pancreas data sets (Baron et al., 2016; Enge et al., 2017; Grün et al., 2016; Lawlor et al., 2017; Muraro et al., 2016; Segerstolpe et al., 2016), and integrated with published mouse pancreas datasets ((Wang et al., 2020), also in example 1). A total of 20,660 human cells (8 data sets) and 7,051 mouse cells (3 data sets) were analyzed (FIGS. 14A-14B). Each cluster was mapped to known abundant endocrine (α, β, δ, epsilon, and PP cells), abundant exocrine (acinar and duct cells), or rare (endothelial, immune cells, quiet and active stellate) cell types (FIGS. 14A-14C). The integration approach revealed a potential endocrine progenitor cluster in human cells, containing cells that are clustered with mouse Procr+ progenitors (FIGS. 14A-14C). This novel human population displayed unique signature genes, including UPK1B, S100A6, LGALS4, SDCBP2, SDC1, IGFBP3, HMGA1, ITGB4, ITGB6, HN1, GPRC5A, SLPI, LAMC2, FERMT1, MGLL, MSLN, SEMA3B, TST, SFN and CDH3 (FIGS. 14D-14E), but did not express known endocrine or exocrine differentiation markers as shown by t-distributed stochastic neighborhood embedding (t-SNE) analysis (FIG. 14C). Pseudo temporal analysis using monocle 2 predicted two developmental trajectories starting from the endocrine progenitors: one toward the β-cell and one toward the α-cell (FIG. 14F). To our surprise, PROCR was not found in the signature. The existence of PROCR$^+$ cells in human islet has been proven by immunostaining of PROCR in sections of human pancreas (FIG. 8A, in Example 2). In scRNA-seq analysis, the absence of PROCR in the signature identified could be due to the low abundance of the PROCR transcript.

To search for a more abundantly expressed marker that can be used to isolate this potential human endocrine progenitor population, we screened through genes in the signature that encode surface proteins. We identified MSLN. Immunostaining of MSLN in sections of human pancreas validated its expression in a small population of islet cells (FIG. 15A). These MSLN+ cells did not express Insulin (INS) (FIG. 15A). Small numbers of MSLN+ cells could also be detected in exocrine Acinar and ducts (FIG. 15B). By FACS analysis, we found that MSLN+ cells consist of about 3-5% of total islet cells (TSQ-high, TSQ-hi) (FIG. 15C). MSLN+ cells could also be seen in 0.5-1% of exocrine cells (TSQ-mid or TSQ-low) (FIG. 15C). Next, we sorted total TSQ-hi cells, and MSLN+ and MSLN− cells within the TSQ-hi compartment (FIG. 15A), and cultured them in the condition established in previous study (FIG. 10, in example 2). We found that total TSQ-hi and TSQ-hi, MSLN+ cells can form organoids, whereas MSLN− cells could not (FIG. 15D). TSQ-hi, MSLN+ cells exhibited markedly higher (about 7-fold) organoid formation efficiency compared to total TSQ-hi cells (FIG. 15D and FIG. 15E). These data suggest that MSLN+ cells are enriched for human pancreatic endocrine progenitors that are capable of forming organoids in vitro.

Figure 15F:
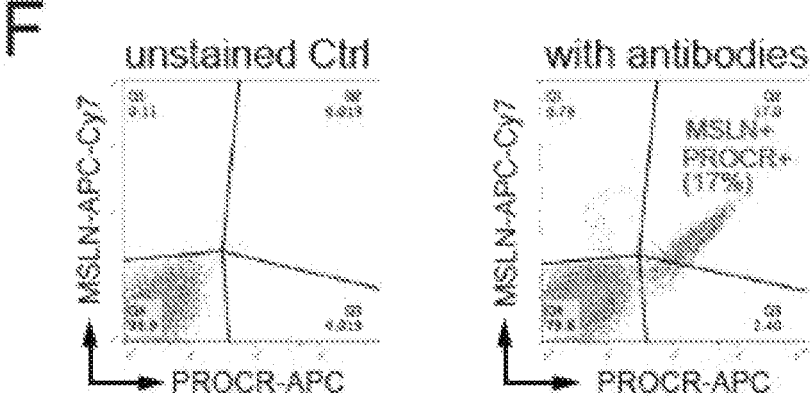

In culture day 14, we analyzed the dissociated organoid cells by FACS. Interestingly, we found that most majority of MSLN+ cells are also PROCR+, and the double positive cells consist of 17% of all organoid cells (FIG. 15F). This suggests that MSLN+ and PROCR+ cells are the same population, reinforcing the notion that the absence of PROCR in scRNA-seq could be due to the low abundance of the PROCR transcript.

In our previous work culturing mouse islet progenitors (in example 1), coculture with endothelial cells (ECs) is essential for organoid formation. Next, we asked whether addition of ECs would benefit human islet organoid formation. ECs were isolated from human pancreas tissues based on CD31 or CD34 expression. Islet cells and ECs were mixed in 5:1 to 1:1 ratio. In these experiments, VEGFa (50 ng/ml) was added to support EC growth. In the solely islet cell group, islet organoids was formed, with sizes ranging from 45-100 μm in culture day 10 (FIG. 16A, and FIG. 16C). The coculture with ECs significantly increased the sizes of the organoids, ranging from 80-180 μm in culture day 10 (FIG. 16B, and FIG. 16C). These results suggest that, although islet organoids can be maintained in defined culture conditions for long term (as shown in example 2), coculture with ECs can promote islet organoid growth, similar to what we found in mouse islet organoid culture.

Together, these data show that the methods and composition described herein can 1) define human pancreatic islet progenitors by the signature stated above, 2) isolate human pancreatic islet progenitors based on surface MSLN expression, and 3) generate functional human β-like cells in vitro. Isolated human islet cells can grow into islet-like organoids in vitro.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

REFERENCE

Al-Hasani, K., Pfeifer, A., Courtney, M., Ben-Othman, N., Gjernes, E., Vieira, A., Druelle, N., Avolio, F., Ravassard, P., Leuckx, G., et al. (2013). Adult duct-lining cells can reprogram into beta-like cells able to counter repeated cycles of toxin-induced diabetes. Dev Cell 26, 86-100.

Balazs, A. B., Fabian, A. J., Esmon, C. T., and Mulligan, R. C. (2006). Endothelial protein C receptor (CD201) explicitly identifies hematopoietic stem cells in murine bone marrow. Blood 107, 2317-2321.

Bonner-Weir, S., Taneja, M., Weir, G. C., Tatarkiewicz, K., Song, K. H., Sharma, A., and O'Neil, J. J. (2000). In vitro cultivation of human islets from expanded ductal tissue. Proc Natl Acad Sci USA 97, 7999-8004.

Butler, A., Hoffman, P., Smibert, P., Papalexi, E., and Satija, R. (2018). Integrating single-cell transcriptomic data across different conditions, technologies, and species. Nat Biotechnol 36, 411-420.

Byrnes, L. E., Wong, D. M., Subramaniam, M., Meyer, N. P., Gilchrist, C. L., Knox, S. M., Tward, A. D., Ye, C. J., and Sneddon, J. B. (2018). Lineage dynamics of murine pancreatic development at single-cell resolution. Nat Commun 9, 3922.

Cheng, X., Ying, L., Lu, L., Galvao, A. M., Mills, J. A., Lin, H. C., Kotton, D. N., Shen, S. S., Nostro, M. C., Choi, J. K., et al. (2012). Self-renewing endodermal progenitor lines generated from human pluripotent stem cells. Cell Stem Cell 10, 371-384.

Criscimanna, A., Speicher, J. A., Houshmand, G., Shiota, C., Prasadan, K., Ji, B., Logsdon, C. D., Gittes, G. K., and Esni, F. (2011). Duct cells contribute to regeneration of endocrine and acinar cells following pancreatic damage in adult mice. Gastroenterology 141, 1451-1462, 1462 e1451-1456.

Fares, I., Chagraoui, J., Lehnertz, B., MacRae, T., Mayotte, N., Tomellini, E., Aubert, L., Roux, P. P., and Sauvageau, G. (2017). EPCR expression marks UM171-expanded CD34+ cord blood stem cells. Blood 129, 3344-3351.

Furuyama, K., Kawaguchi, Y., Akiyama, H., Horiguchi, M., Kodama, S., Kuhara, T., Hosokawa, S., Elbahrawy, A., Soeda, T., Koizumi, M., et al. (2011). Continuous cell supply from a Sox9-expressing progenitor zone in adult liver, exocrine pancreas and intestine. Nat Genet 43, 34-41.

Gao, R., Ustinov, J., Korsgren, O., and Otonkoski, T. (2005). In vitro neogenesis of human islets reflects the plasticity of differentiated human pancreatic cells. Diabetologia 48, 2296-2304.

Gehart, H., van Es, J. H., Hamer, K., Beumer, J., Kretzschmar, K., Dekkers, J. F., Rios, A., and Clevers, H. (2019). Identification of Enteroendocrine Regulators by Real-Time Single-Cell Differentiation Mapping. Cell 176, 1158-1173 e1116.

Gershengorn, M. C., Hardikar, A. A., Wei, C., Geras-Raaka, E., Marcus-Samuels, B., and Raaka, B. M. (2004). Epithelial-to-mesenchymal transition generates proliferative human islet precursor cells. Science 306, 2261-2264.

Greggio, C., De Franceschi, F., Figueiredo-Larsen, M., Gobaa, S., Ranga, A., Semb, H., Lutolf, M., and Grapin-Botton, A. (2013). Artificial three-dimensional niches deconstruct pancreas development in vitro. Development 140, 4452-4462.

Gu, G., Dubauskaite, J., and Melton, D. A. (2002). Direct evidence for the pancreatic lineage: NGN3+ cells are islet progenitors and are distinct from duct progenitors. Development 129, 2447-2457.

Hardikar, A. A. (2016). Pancreatic Islet Biology, 1 edn (Switzerland: Springer International Publishing).

Huch, M., Bonfanti, P., Boj, S. F., Sato, T., Loomans, C. J., van de Wetering, M., Sojoodi, M., Li, V. S., Schuijers, J., Gracanin, A, et al. (2013). Unlimited in vitro expansion of adult bi-potent pancreas progenitors through the Lgr5/R-spondin axis. EMBO J 32, 2708-2721.

Inada, A., Nienaber, C., Katsuta, H., Fujitani, Y., Levine, J., Morita, R., Sharma, A., and Bonner-Weir, S. (2008). Carbonic anhydrase II-positive pancreatic cells are progenitors for both endocrine and exocrine pancreas after birth. Proc Natl Acad Sci USA 105, 19915-19919.

Iwasaki, H., Arai, F., Kubota, Y., Dahl, M., and Suda, T. (2010). Endothelial protein C receptor-expressing hematopoietic stem cells reside in the perisinusoidal niche in fetal liver. Blood 116, 544-553.

Jin, L., Feng, T., Shih, H. P., Zerda, R., Luo, A., Hsu, J., Mandavi, A., Sander, M., Tirrell, D. A., Riggs, A. D., et al. (2013). Colony-forming cells in the adult mouse pancreas are expandable in Matrigel and form endocrine/acinar colonies in laminin hydrogel. Proc Natl Acad Sci USA 110, 3907-3912.

Kopp, J. L., Dubois, C. L., Schaffer, A. E., Hao, E., Shih, H. P., Seymour, P. A., Ma, J., and Sander, M. (2011). Sox9+ ductal cells are multipotent progenitors throughout development but do not produce new endocrine cells in the normal or injured adult pancreas. Development 138, 653-665.

Lammert, E., Cleaver, O., and Melton, D. (2001). Induction of pancreatic differentiation by signals from blood vessels. Science 294, 564-567.

Lysy, P. A., Weir, G. C., and Bonner-Weir, S. (2013). Making beta cells from adult cells within the pancreas. Curr Diab Rep 13, 695-703.

Minami, K., Okuno, M., Miyawaki, K., Okumachi, A., Ishizaki, K., Oyama, K., Kawaguchi, M., Ishizuka, N., Iwanaga, T., and Seino, S. (2005). Lineage tracing and characterization of insulin-secreting cells generated from adult pancreatic acinar cells. Proc Natl Acad Sci USA 102, 15116-15121.

Mohammed, J. S., Wang, Y., Harvat, T. A., Oberholzer, J., and Eddington, D. T. (2009). Microfluidic device for multimodal characterization of pancreatic islets. Lab Chip 9, 97-106.

Ouziel-Yahalom, L., Zalzman, M., Anker-Kitai, L., Knoller, S., Bar, Y., Glandt, M., Herold, K., and Efrat, S. (2006). Expansion and redifferentiation of adult human pancreatic islet cells. Biochem Biophys Res Commun 341, 291-298.

Pagliuca, F. W., Millman, J. R., Gurtler, M., Segel, M., Van Dervort, A., Ryu, J. H., Peterson, Q. P., Greiner, D., and Melton, D. A. (2014). Generation of functional human pancreatic beta cells in vitro. Cell 159, 428-439.

Pan, F. C., Bankaitis, E. D., Boyer, D., Xu, X., Van de Casteele, M., Magnuson, M. A., Heimberg, H., and Wright, C. V. (2013). Spatiotemporal patterns of multi-potentiality in Ptf1a-expressing cells during pancreas organogenesis and injury-induced facultative restoration. Development 140, 751-764.

Pan, F. C., and Wright, C. (2011). Pancreas organogenesis: from bud to plexus to gland. Dev Dyn 240, 530-565.

Qiu, X., Mao, Q., Tang, Y., Wang, L., Chawla, R., Pliner, H. A., and Trapnell, C. (2017). Reversed graph embedding resolves complex single-cell trajectories. Nat Methods 14, 979-982.

Ramiya, V. K., Maraist, M., Arfors, K. E., Schatz, D. A., Peck, A. B., and Cornelius, J. G. (2000). Reversal of insulin-dependent diabetes using islets generated in vitro from pancreatic stem cells. Nat Med 6, 278-282.

Rezania, A., Bruin, J. E., Arora, P., Rubin, A., Batushansky, I., Asadi, A., O'Dwyer, S., Quiskamp, N., Mojibian, M., Albrecht, T., et al. (2014). Reversal of diabetes with insulin-producing cells derived in vitro from human pluripotent stem cells. Nat Biotechnol 32, 1121-1133.

Rovira, M., Scott, S. G., Liss, A. S., Jensen, J., Thayer, S. P., and Leach, S. D. (2010). Isolation and characterization of centroacinar/terminal ductal progenitor cells in adult mouse pancreas. Proc Natl Acad Sci USA 107, 75-80.

Rukstalis, J. M., and Habener, J. F. (2007). Snail2, a mediator of epithelial-mesenchymal transitions, expressed in progenitor cells of the developing endocrine pancreas. Gene Expr Patterns 7, 471-479.

Russ, H. A., Bar, Y., Ravassard, P., and Efrat, S. (2008). In vitro proliferation of cells derived from adult human beta-cells revealed by cell-lineage tracing. Diabetes 57, 1575-1583.

Scavuzzo, M. A., Hill, M. C., Chmielowiec, J., Yang, D., Teaw, J., Sheng, K., Kong, Y., Bettini, M., Zong, C., Martin, J. F., et al. (2018). Endocrine lineage biases arise in temporally distinct endocrine progenitors during pancreatic morphogenesis. Nat Commun 9, 3356.

Seaberg, R. M., Smukler, S. R., Kieffer, T. J., Enikolopov, G., Asghar, Z., Wheeler, M. B., Korbutt, G., and van der Kooy, D. (2004). Clonal identification of multipotent precursors from adult mouse pancreas that generate neural and pancreatic lineages. Nat Biotechnol 22, 1115-1124.

Smukler, S. R., Arntfield, M. E., Razavi, R., Bikopoulos, G., Karpowicz, P., Seaberg, R., Dai, F., Lee, S., Ahrens, R., Fraser, P. E., et al. (2011). The adult mouse and human pancreas contain rare multipotent stem cells that express insulin. Cell Stem Cell 8, 281-293.

Sneddon, J. B., Borowiak, M., and Melton, D. A. (2012). Self-renewal of embryonic-stem-cell-derived progenitors by organ-matched mesenchyme. Nature 491, 765-768.

Sugiyama, T., Benitez, C. M., Ghodasara, A., Liu, L., McLean, G. W., Lee, J., Blauwkamp, T. A., Nusse, R., Wright, C. V., Gu, G., et al. (2013). Reconstituting pancreas development from purified progenitor cells reveals genes essential for islet differentiation. Proc Natl Acad Sci USA 110, 12691-12696.

Van de Casteele, M., Leuckx, G., Baeyens, L., Cai, Y., Yuchi, Y., Coppens, V., De Groef, S., Eriksson, M., Svensson, C., Ahlgren, U., et al. (2013). Neurogenin 3+ cells contribute to beta-cell neogenesis and proliferation in injured adult mouse pancreas. Cell Death Dis 4, e523.

Wang, D., Cai, C., Dong, X., Yu, Q. C., Zhang, X. O., Yang, L., and Zeng, Y. A. (2015). Identification of multipotent mammary stem cells by protein C receptor expression. Nature 517, 81-84.

Xu, X., D'Hoker, J., Stange, G., Bonne, S., De Leu, N., Xiao, X., Van de Casteele, M., Mellitzer, G., Ling, Z., Pipeleers, D., et al. (2008). Beta cells can be generated from endogenous progenitors in injured adult mouse pancreas. Cell 132, 197-207.

Yatoh, S., Dodge, R., Akashi, T., Omer, A., Sharma, A., Weir, G. C., and Bonner-Weir, S. (2007). Differentiation of affinity-purified human pancreatic duct cells to beta-cells. Diabetes 56, 1802-1809.

Yu, Q. C., Song, W., Wang, D., and Zeng, Y. A. (2016). Identification of blood vascular endothelial stem cells by the expression of protein C receptor. Cell Res 26, 1079-1098.

Zhou, F., Li, X., Wang, W., Zhu, P., Zhou, J., He, W., Ding, M., Xiong, F., Zheng, X., Li, Z., et al. (2016). Tracing haematopoietic stem cell formation at single-cell resolution. Nature 533, 487-492.

Baron, M., Veres, A., Wolock, Samuel L., Faust, Aubrey L., Gaujoux, R., Vetere, A., Ryu, Jennifer H., Wagner, Bridget K., Shen-Orr, Shai S., Klein, Allon M., et al. (2016). A Single-Cell Transcriptomic Map of the Human and Mouse Pancreas Reveals Inter- and Intra-cell Population Structure. Cell Systems 3, 346-360.e344.

Enge, M., Arda, H. E., Mignardi, M., Beausang, J., Bottino, R., Kim, S. K., and Quake, S. R. (2017). Single-Cell Analysis of Human Pancreas Reveals Transcriptional Signatures of Aging and Somatic Mutation Patterns. Cell 171, 321-330.e314.

Grün, D., Muraro, Mauro J., Boisset, J.-C., Wiebrands, K., Lyubimova, A., Dharmadhikari, G., van den Born, M., van Es, J., Jansen, E., Clevers, H., et al. (2016). De Novo Prediction of Stem Cell Identity using Single-Cell Transcriptome Data. Cell Stem Cell 19, 266-277.

Lawlor, N., George, J., Bolisetty, M., Kursawe, R., Sun, L., Sivakamasundari, V., Kycia, I., Robson, P., and Stitzel, M. L. (2017). Single-cell transcriptomes identify human islet cell signatures and reveal cell-type-specific expression changes in type 2 diabetes. Genome Research 27, 208-222.

Muraro, Mauro J., Dharmadhikari, G., Grün, D., Groen, N., Dielen, T., Jansen, E., van Gurp, L., Engelse, Marten A., Carlotti, F., de Koning, Eelco J. P., et al. (2016). A Single-Cell Transcriptome Atlas of the Human Pancreas. Cell Systems 3, 385-394.e383.

Segerstolpe, Å., Palasantza, A., Eliasson, P., Andersson, E.-M., Andréasson, A.-C., Sun, X., Picelli, S., Sabirsh, A., Clausen, M., Bjursell, M. K., et al. (2016). Single-Cell Transcriptome Profiling of Human Pancreatic Islets in Health and Type 2 Diabetes. Cell Metabolism 24, 593-607.

Wang, D., Wang, J., Bai, L., Pan, H., Feng, H., Clevers, H., and Zeng, Y. A. (2020). Long-Term Expansion of Pancreatic Islet Organoids from Resident Procr(+) Progenitors. Cell 180, 1198-1211 e1119.

The invention claimed is:

1. A method of producing a pancreatic organoid in vitro, comprising:

providing an endocrine progenitor cell which does not express insulin and is isolated from adult islet cells, or providing an endocrine progenitor cell within a population of adult islet cells, wherein the endocrine progenitor cells are Procr+ and/or MSLN+ endocrine progenitor cells; and 3D culturing in vitro the endocrine progenitor cell in an organoid medium under conditions suitable to produce a pancreatic organoid comprising functional β-cells and/or β-like cells.

2. The method of claim 1, wherein the adult islet cells are from human and the endocrine progenitor cell is MSLN+, wherein optionally the endocrine progenitor cell further expresses one or more of UPK1B, S100A6, LGALS4, SDCBP2, SDC1, IGFBP3, HMGA1, ITGB4, ITGB6, HN1, GPRC5A, SLPI, LAMC2, FERMT1, MGLL, SEMA3B, TST, SFN, CDH3 and PROCR; or the adult islet cells are from mouse and the endocrine progenitor cell is Procr+, wherein the 3D culturing comprises co-culturing with a plurality of endothelial cells, and wherein optionally the endocrine progenitor cell further expresses one or more of Rspo1, Fgf1, Upk3B, Hoxa5 and Msln.

3. The method of claim 1, further comprising contacting, in vitro, dissociated adult human islet cells with an anti-MSLN antibody or antigen-binding fragment thereof, followed by fluorescence assisted cell sorting (FACS), to isolate the endocrine progenitor cell; or contacting, in vitro, dissociated adult mouse islet cells with an anti-Procr antibody or antigen-binding fragment thereof, followed by fluorescence assisted cell sorting (FACS), to isolate the endocrine progenitor cell;

or further comprising enriching the endocrine cells by one or more of the following methods: (1) staining dissociated adult islet cells with TSQ (6-methoxy-8-p-toluenesulfonamido-quilone), followed by FACS; (2) density gradient centrifugation of dissociated adult islet cells; and (3) hand-picking and dissociating islets from adult islet cells.

4. The method of claim 2, wherein the organoid medium for the MSLN+ endocrine progenitor cell comprises a basal medium supplemented with one or more of: 10-200 ng ml$^{-1}$ EGF, 1-50 ng ml$^{-1}$ FGF2, 1-10 μM Wnt agonist or 1-100 ng/ml Wnt surrogate, 0.1-5 μM TGF-beta pathway inhibitors, 10-500 ng ml$^{-1}$ Bmp inhibitor, 1-10 μM Rock inhibitor, and 1-10 μM of p38 inhibitor SB202190, and wherein optionally the basal medium is further supplemented with one or more of 1-5% B27, 0.1-5% ITS, 0.1-5 μg ml$^{-1}$ heparin, and 1-100 ng ml⁻¹ VEGFa; the culture medium for the Procr+ endocrine progenitor cell comprises a basal medium supplemented with one or more of: 10-200 ng ml⁻¹ EGF, 1-50 ng ml⁻¹ FGF2, and 1-20 ng ml⁻¹ VEGFa, and wherein optionally the basal medium is further supplemented with one or more of 1-5% B27, 0.1-5% ITS, and 0.1-5 µg ml⁻¹ heparin.

5. The method of claim 1, wherein the culturing step comprises culturing until the endocrine progenitor cell forms a colony of about 100-300 µm in diameter, and continuously culturing the colony to form a pancreatic organoid of about 150-500 µm in diameter.

6. A method of obtaining endocrine progenitor cells, comprising:
   contacting, in vitro, adult human islet cells with an anti-MSLN antibody or antigen-binding fragment thereof, and
   isolating a MSLN+ endocrine progenitor cell that binds to the anti-MSLN antibody or fragment thereof; or comprising:
   contacting, in vitro, adult mouse islet cells with an anti-Procr antibody or antigen-binding fragment thereof; and
   isolating a Procr+ endocrine progenitor cell that binds to the anti-Procr antibody or fragment thereof.

7. A composition comprising a plurality of endocrine progenitor cells which do not express insulin and are isolated from adult islet cells, a culture medium and optionally a plurality of endothelial cells, wherein the endocrine progenitor cells are Procr+ and/or MSLN+ endocrine progenitor cells.

8. The composition of claim 7, wherein the culture medium comprises a three-dimensional matrix, which is an extracellular matrix.

9. The composition of claim 7, wherein the adult islet cells are from human, and the endocrine progenitor cells express MSLN and optionally one or more of UPK1B, S100A6, LGALS4, SDCBP2, SDC1, IGFBP3, HMGA1, ITGB4, ITGB6, HN1, GPRC5A, SLPI, LAMC2, FERMT1, MGLL, SEMA3B, TST, SFN, CDH3 and PROCR; or the adult islet cells are derived from mouse, and the endocrine progenitor cells express Procr and optionally one or more of Rspo1, Fgf1, Upk3B, Hoxa5 and Msln.

10. The composition of claim 9, wherein the culture medium for the endocrine progenitor cells expressing MSLN comprises a basal medium supplemented with one or more of: 10-200 ng ml⁻¹ EGF, 1-50 ng ml⁻¹ FGF2, 1-10 µM Wnt agonist or 1-100 ng/ml Wnt surrogate, 0.1-5 µM TGF-beta pathway inhibitors, 10-500 ng ml⁻¹ Bmp inhibitor, 1-10 µM Rock inhibitor, and 1-10 µM of p38 inhibitor SB202190; wherein optionally the basal medium is further supplemented with one or more of 1-5% B27, 0.1-5% ITS, 0.1-5 µg ml⁻¹ heparin, and 1-100 ng ml⁻¹ VEGFa; the culture medium for the endocrine progenitor cells expressing Procr comprises a basal medium supplemented with one or more of: 10-200 ng ml⁻¹ EGF, 1-50 ng ml⁻¹ FGF2, and 1-20 ng ml⁻¹ VEGFa, and wherein optionally the basal medium is further supplemented with one or more of 1-5% B27, 0.1-5% ITS, and 0.1-5 µg ml⁻¹ heparin.

11. A pancreatic organoid comprising functional β-cells and/or β-like cells differentiated in vitro from endocrine progenitor cells, wherein the endocrine progenitor cells do not express insulin and are isolated from adult islet cells and the endocrine progenitor cells are Procr+ and/or MSLN+ endocrine progenitor cells.

12. The organoid of claim 11, wherein the pancreatic organoid senses glucose and produces and secretes insulin in response to glucose, and/or the pancreatic organoid is about 50-500 µm in diameter.

13. A method for treating or preventing diabetes comprising administering to a subject in need thereof the pancreatic organoid of claim 11.

14. A method for screening in vitro an agent for treating or preventing diabetes by using the pancreatic organoid of claim 11.

15. The method of claim 1, further comprising expanding the pancreatic organoid through passaging for at least 10 times, at least 20 times, or at least 30 times, and optionally culturing the expanded pancreatic organoids for about 1-12 or 1-4 or 2-12 weeks to generate mature organoids.

16. The method of claim 15, wherein the mature organoid senses glucose and produces and secretes insulin in response to glucose.

17. The method of claim 2, wherein the organoid medium for the MSLN+ endocrine progenitor cell comprises a basal medium DMEM/F12 supplemented with one or more of: 10-200 ng ml⁻¹ EGF, 1-50 ng ml⁻¹ FGF2, 1-10 µM CHIR99021 or 1-100 ng/ml NGS, 0.1-5 µM SB431542 or A83-01, 10-500 ng ml⁻¹ Noggin, 1-10 µM Y27632, and 1-10 UM of p38 inhibitor SB202190, and wherein optionally the basal medium is further supplemented with one or more of 1-5% B27, 0.1-5% ITS, 0.1-5 µg ml⁻¹ heparin, and 1-100 ng ml⁻¹ VEGFa; the culture medium for the Procr+ endocrine progenitor cell comprises a basal medium DMEM/F12 supplemented with one or more of: 10-200 ng ml⁻¹ EGF, 1-50 ng ml⁻¹ FGF2, and 1-20 ng ml⁻¹ VEGFa, and wherein optionally the basal medium is further supplemented with one or more of 1-5% B27, 0.1-5% ITS, and 0.1-5 µg ml⁻¹ heparin.

18. The composition of claim 9, wherein the culture medium for the endocrine progenitor cells expressing MSLN comprises a basal medium DMEM/F12 supplemented with one or more of: 10-200 ng ml⁻¹ EGF, 1-50 ng ml⁻¹ FGF2, 1-10 UM CHIR99021 or 1-100 ng/ml NGS, 0.1-5 µM SB431542 or A83-01, 10-500 ng ml⁻¹ Noggin, 1-10 µM Y27632, and 1-10 µM of p38 inhibitor SB202190; wherein optionally the basal medium is further supplemented with one or more of 1-5% B27, 0.1-5% ITS, 0.1-5 µg ml⁻¹ heparin, and 1-100 ng ml⁻¹ VEGFa; the culture medium for the endocrine progenitor cells expressing Procr comprises a basal medium supplemented with one or more of: 10-200 ng ml⁻¹ EGF, 1-50 ng ml⁻¹ FGF2, and 1-20 ng ml⁻¹ VEGFa, and wherein optionally the basal medium is further supplemented with one or more of 1-5% B27, 0.1-5% ITS, and 0.1-5 µg ml⁻¹ heparin.

19. The method of claim 1, wherein the organoid medium further comprises a three-dimensional matrix which is an extracellular matrix.

20. The method of claim 6, wherein the method comprises using fluorescence assisted cell sorting (FACS) to isolate a MSLN+ endocrine progenitor cell that binds to the anti-MSLN antibody or fragment thereof or to isolate a Procr+ endocrine progenitor cell that binds to the anti-Procr antibody or fragment thereof.

* * * * *

SEQUENCE LISTING

```
<160> NUMBER OF SEQ ID NOS: 20

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
tcagtcaacg ggggacataa a                                              21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
ggggctgtac tgcttaacca g                                              21

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ctctctggga aaactcctga ca                                             22
```

```
<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
cagggagcag ctaacagtga                                               20

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
gcaaccccga catgaacaaa t                                             21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
ggtgctgtta gcggctgtag                                               20

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
cagctcagtg cggaaagtg                                                19

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tgtctgcgag ccgtataaaa g                                             21

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
agacctgatt gcctacgtgc                                               20

<210> SEQ ID NO 10
<211> LENGTH: 23
<212> TYPE: DNA
<213> ORGANISM: Artificial Sequence
<220> FEATURE:
```

```
<223> OTHER INFORMATION: Primer

<400> SEQUENCE: 10
ggtgtcctta gttgagacat gct                                    23

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
ctcattttgc ggtcgctatc c                                      21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
atccatgcca ttgtagccgt a                                      21

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
tggcttcttc tacacaccca ag                                     22

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
acaatgccac gcttctgcc                                         19

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gtcatccgac tgaaacagaa                                        20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
gccaacttct cgtatttctc                                        20
```

-continued

```
<210> SEQ ID NO 17
<211> LENGTH: 21
<212> TYPE: DNA
<213> ORGANISM: Artificial Sequence
<220> FEATURE:
<223> OTHER INFORMATION: Primer

<400> SEQUENCE: 17
aagcctctcc cacaagttct a                                                    21

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
gaggtgcgtt tggttgtcat c                                                    21

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
ccccagttta caagctcgct                                                      20

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
ctcggttcca ttcgggaaag g                                                    21
```